(12) United States Patent
Bamford et al.

(10) Patent No.: US 7,888,347 B2
(45) Date of Patent: Feb. 15, 2011

(54) PYRAZOLO [3,4-D]AZEPINE DERIVATIVES AS HISTAMINE H3 ANTAGONISTS

(75) Inventors: Mark James Bamford, Harlow (GB); David Matthew Wilson, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 483 days.

(21) Appl. No.: 11/994,689

(22) PCT Filed: Jul. 4, 2006

(86) PCT No.: PCT/EP2006/006613

§ 371 (c)(1),
(2), (4) Date: Jan. 4, 2008

(87) PCT Pub. No.: WO2007/025596

PCT Pub. Date: Mar. 8, 2007

(65) Prior Publication Data

US 2008/0176832 A1 Jul. 24, 2008

(30) Foreign Application Priority Data

Jul. 6, 2005 (GB) .................. 0513886.2

(51) Int. Cl.
*A61P 25/28* (2006.01)
*A61K 31/55* (2006.01)
*C07D 487/04* (2006.01)

(52) U.S. Cl. ....................................... 514/215; 540/578
(58) Field of Classification Search ................. 514/215; 540/578

See application file for complete search history.

(56) References Cited

FOREIGN PATENT DOCUMENTS

| | | |
|---|---|---|
| JP | 2001220390 A | 8/2001 |
| WO | 0013508 A1 | 3/2000 |
| WO | 03104235 A1 | 12/2003 |
| WO | 2004008837 A3 | 1/2004 |
| WO | 2004013144 A1 | 2/2004 |
| WO | 2004018432 A1 | 3/2004 |
| WO | 2004035544 A1 | 4/2004 |
| WO | 2004037788 A1 | 5/2004 |
| WO | 2004056369 A1 | 7/2004 |
| WO | 2005058837 A1 | 6/2005 |
| WO | 2005087746 A1 | 9/2005 |
| WO | 2005097778 A1 | 10/2005 |
| WO | 2005123723 A1 | 12/2005 |
| WO | 2006018260 A1 | 2/2006 |
| WO | 2006061193 A1 | 6/2006 |
| WO | 2006097691 A1 | 9/2006 |

*Primary Examiner*—Brenda L Coleman
(74) *Attorney, Agent, or Firm*—Duke M. Fitch; Kathryn L. Sieburth; Lorraine Ling

(57) ABSTRACT

The present invention relates to novel pyrazole derivatives of formula I having pharmacological activity as H3 antagonists processes for their preparation, to compositions containing them and to their use in the treatment of neurological and psychiatric disorders.

11 Claims, No Drawings

PYRAZOLO [3,4-D]AZEPINE DERIVATIVES AS HISTAMINE H3 ANTAGONISTS

CROSS-REFERENCE TO RELATED APPLICATIONS

This application is filed pursuant to 35 U.S.C. §371 as a United States National Phase Application of International Application No. PCT/EP2006/006613 filed 4 Jul. 2006, which claims priority from GB Application No. 0513886.2 filed 6 Jul. 2005.

FIELD OF THE INVENTION

The present invention relates to novel pyrazole derivatives having pharmacological activity, processes for their preparation, to compositions containing them and to their use in the treatment of neurological and psychiatric disorders.

WO 2004/05639 (Glaxo Group Ltd.) describes a series of benzazepine derivatives and their use in the treatment of neurological disorders. WO2004/013144 (Pharmacia Italia S.P.A.) discloses a series of bicycle-pyrazoles, which are claimed to be useful in the treatment of diseases linked to deregulated protein kinases. WO2004008837 and WO200013508 (Ishihara Sangyo Kaisha Ltd.) disclose benzene derivatives claimed to be useful as herbicides. JP2001220390 describes pyrazole derivatives useful as calcium channel and IL-2 production inhibitors.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

The present invention provides, in a first aspect, a compound of formula (I) or a pharmaceutically acceptable salt thereof:

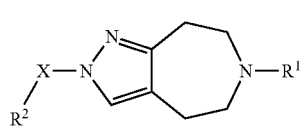

(I)

wherein:

$R^1$ represents —$C_{1-6}$ alkyl, —$C_{3-7}$ cycloalkyl or —$CH_2$—$C_{3-7}$ cycloalkyl, wherein said cycloalkyl groups may be optionally substituted by $C_{1-3}$ alkyl;

X represents bond or —$CH_2$—, $R^2$ represents -aryl, -aryl-aryl, -aryl-heteroaryl, -aryl-heterocyclyl, -heteroaryl, -heteroaryl-aryl, -heteroaryl-heteroaryl, -heteroaryl-heterocyclyl, -heterocyclyl, -heterocyclyl-aryl, -heterocyclyl-heteroaryl or -heterocyclyl-heterocyclyl;

wherein said aryl, heteroaryl and heterocyclyl groups of $R^2$ may be optionally substituted by one or more substituents (e.g. 1, 2 or 3) which may be the same or different, and which are selected from the group consisting of halogen, hydroxy, cyano, nitro, =O, $C_{1-6}$ alkyl, halo$C_{1-6}$ alkyl, —O-halo$C_{1-6}$ alkyl, —O—$C_{1-6}$ alkyl, —$C_{1-6}$ alkyl-O—$C_{1-6}$ alkyl, —$CO_2R^4$, —$COR^4$, —$C_{1-6}$ alkyl-$COR^4$, —$SR^4$, —$SO_2R^4$, —$SOR^4$, —$OSO_2R^4$, —$C_{1-6}$ alkyl-$SO_2R^4$, —$C_{1-6}$ alkyl-$NR^4SO_2R^5$, —$C_{1-6}$ alkyl-$SO_2NR^4R^5$, —$NR^4R^5$, —$C_{1-6}$ alkyl-$NR^4R^5$, —$C_{3-8}$ cycloalkyl-$NR^4R^5$, —$CONR^4R^5$, —$NR^4COR^5$, —$C_{1-6}$ alkyl-$NR^4COR^5$, —$C_{1-6}$ alkyl-$CONR^4R^5$, —$NR^4SO_2R^5$, —$OCONR^4R^5$, —$NR^4CO_2R^5$, —$NR^6CONR^4R^5$ or —$SO_2NR^4R^5$ (wherein $R^4$, $R^5$ and $R^6$ independently represent hydrogen, $C_{1-6}$ alkyl, or wherein —$NR^4R^5$ may represent a nitrogen containing heterocyclyl group); and wherein $R^4$, $R^5$ and $R^6$ may be optionally substituted by one or more substituents (e.g. 1, 2 or 3) which may be the same or different, and which are selected from the group consisting of halogen, hydroxy, cyano, amino, nitro and =O; or solvates thereof.

DETAILED DESCRIPTION

In one aspect, $R^1$ represents —$C_{3-7}$ cycloalkyl, wherein the cycloalkyl group may be optionally substituted by $C_{1-3}$ alkyl.

The term '$C_{x-y}$ alkyl' as used herein as a group or a part of the group refers to a linear or branched saturated hydrocarbon group containing from x to y carbon atoms. Examples of $C_{1-6}$ alkyl groups include methyl, ethyl, n-propyl, isopropyl, n-butyl, isobutyl, sec-butyl, tert butyl, n-pentyl, isopentyl, neopentyl or hexyl and the like.

The term '$C_{x-y}$ cycloalkyl' as used herein refers to a saturated monocyclic hydrocarbon ring of x to y carbon atoms. Examples of $C_{3-7}$ cycloalkyl groups include cyclopropyl, cyclobutyl, cyclopentyl, cyclohexyl and cycloheptyl.

The term 'halogen' as used herein refers to a fluorine, chlorine, bromine or iodine atom.

The term 'halo$C_{x-y}$ alkyl' as used herein refers to a $C_{x-y}$ alkyl group as defined herein wherein at least one hydrogen atom is replaced with halogen. Examples of halo$C_{1-6}$ alkyl groups include fluoroethyl, trifluoromethyl or trifluoroethyl and the like.

The term 'aryl' as used herein refers to a $C_{6-12}$ monocyclic or bicyclic hydrocarbon ring wherein at least one ring is aromatic. Examples of such groups include phenyl, naphthyl or tetrahydronaphthalenyl and the like. In one embodiment, the term 'aryl' refers to a $C_{6-12}$ monocyclic aromatic ring, particularly phenyl.

The term 'heteroaryl' as used herein refers to a 5-6 membered monocyclic aromatic or a fused 8-10 membered bicyclic aromatic ring, which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like. In one embodiment, the term 'heteroaryl' refers to a 5-6 membered monocyclic aromatic ring which contains 1 to 4 heteroatoms selected from oxygen, nitrogen and sulphur. More particularly, the term 'heteroaryl' refers to a 5-6 membered monocyclic aromatic ring which contains at least one nitrogen atom and 1 to 3 other heteroatoms selected from oxygen, nitrogen and sulphur.

The term 'heterocyclyl' refers to a 4-7 membered monocyclic ring or a fused 8-12 membered bicyclic ring which may be saturated or partially unsaturated, which monocyclic or bicyclic ring contains 1 to 4 heteroatoms selected from oxygen, nitrogen or sulphur. Examples of such monocyclic rings include pyrrolidinyl, azetidinyl, pyrazolidinyl, oxazolidinyl, imidazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like. In one embodiment, the term 'heterocyclyl' refers to a 4-7 membered monocyclic ring which may be saturated or partially unsaturated, which monocyclic ring contains 1 to 4 heteroatoms selected from oxygen, nitrogen or sulphur. More particularly, the term 'heterocyclyl' refers a nitrogen containing heterocyclyl group The term 'nitrogen containing heterocyclyl' refers to a 4-7 membered monocyclic ring which may be saturated or partially unsaturated, which monocyclic ring contains at least one nitrogen atom and 1 to 3 other heteroatoms selected from oxygen, nitrogen or sulphur. Examples of nitrogen containing heterocyclyl groups include pyrrolidinyl, azetidinyl, pyrazolidinyl, oxazolidinyl, imidazolidinyl, piperidinyl, piperazinyl, morpholinyl, thiomorpholinyl, thiazolidinyl, hydantoinyl, valerolactamyl, tetrahydropyridinyl, tetrahydropyrimidinyl, diazepanyl, azepanyl and the like.

In one embodiment, $R^1$ represents $—C_{3-7}$ cycloalkyl (e.g. cyclobutyl, cyclopentyl or cyclohexyl) wherein the cycloalkyl group is optionally substituted by $C_{1-3}$ alkyl. In a more particular embodiment, $R^1$ represents unsubstituted $—C_{3-7}$ cycloalkyl (e.g. cyclobutyl, cyclopentyl or cyclohexyl), particularly unsubstituted cyclobutyl.

In an alternative embodiment, $R^1$ represents $—C_{1-6}$alkyl (e.g. ethyl, 1-methylethyl, 2-methylpropyl), particularly 1-methylethyl or 2-methylpropyl.

In another embodiment, $R^1$ represents $—CH_2—C_{3-7}$ cycloalkyl (e.g. cyclopropylmethyl) wherein the cycloalkyl group is optionally substituted by $C_{1-3}$ alkyl. More particularly, $R^1$ represents unsubstituted $—CH_2—C_{3-7}$ cycloalkyl, particularly cyclopropylmethyl.

In another embodiment, X represents a bond or $—CH_2—$. More particularly, X represents a bond.

In one embodiment, $R^2$ represents -aryl, -aryl-heterocyclyl, -aryl-heteroaryl, -heteroaryl-heterocyclyl and -heterocyclyl-heteroaryl.

In a more particular embodiment, the aryl, heteroaryl and heterocyclyl groups of $R^2$ may be optionally substituted by one or more substituents (e.g. 1, 2 or 3) which may be the same or different, and which are selected from the group consisting of halogen, hydroxy, cyano, nitro, $=O$, $C_{1-6}$ alkyl, haloC$_{1-6}$ alkyl, $—O$-haloC$_{1-6}$ alkyl, $—O—C_{1-6}$ alkyl, $—SO_2R^4$, $—CONR^4R^5$, $—NR^4COR^5$, $—NR^4SO_2R^5$ or $—SO_2NR^4R^5$. Even more particularly, the substituents on the aryl, heteroaryl or heterocyclyl groups of $R^2$ are selected from halogen, hydroxy, cyano, nitro, $=O$, $C_{1-6}$ alkyl, $—O—C_{1-6}$ alkyl, haloC$_{1-6}$ alkyl, $—O$-haloC$_{1-6}$ alkyl and $—CONR^4R^5$.

In one embodiment, $R^4$, $R^5$ and $R^6$ are independently selected from hydrogen and $C_{1-6}$ alkyl. In a more particular embodiment, $R^4$, $R^5$ and $R^6$ are independently selected from hydrogen and $C_{1-3}$ alkyl.

In a further embodiment, $R^2$ represents:
- -aryl (e.g. phenyl) optionally substituted by one or more substituents (e.g. 1, 2 or 3) such as $—CONR^4R^5$ (e.g. $—CONH_2$, $—CONHMe$, $—CONMe_2$), $—SO_2R^4$ (e.g. $—SO_2Me$), $—NR^4SO_2R^5$ (e.g. $—NHSO_2Me$), cyano or halogen (e.g. bromo);
- -aryl-heterocyclyl (e.g. phenyl-pyrrolidinyl, phenyl-oxazolidinyl, phenyl-imidazolidinyl, phenyl-morpholinyl, phenyl-piperidinyl) optionally substituted on the heterocyclyl group by one or more (e.g. 1, 2 or 3) substituents such as $=O$ groups and $—C_{1-6}$alkyl (e.g. methyl);
- -aryl-heteroaryl (e.g. phenyl-oxadiazolyl) optionally substituted by one or more substituents (e.g. 1, 2 or 3) such as $—C_{1-6}$alkyl (e.g. methyl);
- -heteroaryl-heterocyclyl (e.g. pyridinyl-pyrrolidinyl) optionally substituted on the heterocyclyl group by one or more substitutents (e.g. 1, 2 or 3) such as $=O$ groups; or
- -heterocyclyl-heteroaryl (e.g. piperidinyl-pyridinyl) optionally substituted by one or more substitutents (e.g. 1, 2 or 3) such as $—C_{1-6}$alkyl (e.g. methyl).

In embodiments in which $R^2$ represents aryl-heterocyclyl or heteroaryl-heterocyclyl and the heterocyclyl group is a nitrogen containing heterocyclyl group, the heterocyclyl group may be linked to the aryl or heteroaryl through a nitrogen atom.

In a more particular embodiment, $R^2$ represents:
- -aryl (e.g. phenyl) optionally substituted by one or more substituents (e.g. 1, 2 or 3) such as $—CONR^4R^5$ (e.g. $—CONH_2$, $—CONHMe$, $—CONMe_2$), $—SO_2R^4$ (e.g. $—SO_2Me$), $—NR^4SO_2R^5$ (e.g. $—NHSO_2Me$), cyano or halogen (e.g. bromo);
- -aryl-heterocyclyl (e.g. -phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as $=O$ groups (e.g. -phenyl-1-pyrrolidin-2-one, -phenyl-3-(1,3-oxazolidin-2-one), -phenyl-3-imidazolidin-2-one, -phenyl-3-imidazolidin-2,4-dione) and $—C_{1-6}$alkyl (e.g. methyl);
- -aryl-heteroaryl (e.g. -phenyl-1,2,4-oxadiazol-5-yl) optionally substituted by one or more substituents (e.g. 1, 2 or 3) such as $—C_{1-6}$alkyl (e.g. methyl);
- -heteroaryl-heterocyclyl (e.g. 2-(pyrrolidin-1-yl)-pyridin-5-yl) optionally substituted on the heterocyclyl group by one or more substituents (e.g. 1, 2 or 3) such as $=O$ groups (e.g. 2-(N-pyrrolidin-2-one)-pyridin-5-yl); or
- -heterocyclyl-heteroaryl (e.g. 1-(pyridin-3-yl)-piperidin-4-yl) optionally substituted by one or more substitutents (e.g. 1, 2 or 3) such as $—C_{1-6}$alkyl (e.g. methyl).

More particularly, $R^2$ represents:
- aryl (e.g. phenyl) optionally substituted by one or more substituents (e.g. 1, 2 or 3) such as —CONR$^4$R$^5$ (e.g. —CONH$_2$, —CONHMe, —CONMe$_2$), —SO$_2$R$^4$ (e.g. —SO$_2$Me), —NR$^4$SO$_2$R$^5$ (e.g. —NHSO$_2$Me), cyano or halogen (e.g. bromo);
- aryl-heterocyclyl (e.g. -phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as =O groups (e.g. -phenyl-1-pyrrolidin-2-one, -phenyl-3-(1,3-oxazolidin-2-one), -phenyl-3-imidazolidin-2-one, -phenyl-3-imidazolidin-2,4-dione) and —C$_{1-6}$alkyl (e.g. methyl); or
- heteroaryl-heterocyclyl (e.g. 2-(pyrrolidin-1-yl)-pyridin-5-yl) optionally substituted on the heterocyclyl group by one or more substituents (e.g. 1, 2 or 3) such as =O groups (e.g. 2-(N-pyrrolidin-2-one)-pyridin-5-yl).

Most particularly, $R^2$ represents:
- aryl-heterocyclyl (e.g. -phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as =O groups (e.g. -phenyl-1-pyrrolidin-2-one, -phenyl-3-(1,3-oxazolidin-2-one), -phenyl-3-imidazolidin-2-one, -phenyl-3-imidazolidin-2,4-dione) and —C$_{1-6}$alkyl (e.g. methyl); or
- heteroaryl-heterocyclyl (e.g. 2-(pyrrolidin-1-yl)-pyridin-5-yl) optionally substituted on the heterocyclyl group by one or more substituents (e.g. 1, 2 or 3) such as =O groups (e.g. 2-(N-pyrrolidin-2-one)-pyridin-5-yl).

In one aspect, the present invention provides a compound of formula (I) or a pharmaceutically acceptable salt or solvate thereof, wherein:

$R^1$ represents —C$_{1-6}$alkyl, —C$_{3-7}$ cycloalkyl or —CH$_2$—C$_{3-7}$cycloalkyl, wherein said cycloalkyl groups may be optionally substituted by C$_{1-3}$ alkyl;

X represents a bond or —CH$_2$—, $R^2$ represents -aryl, -aryl-heterocyclyl, -aryl-heteroaryl, -heteroaryl-heterocyclyl and -heterocyclyl-heteroaryl;

wherein said aryl, heteroaryl and heterocyclyl groups of $R^2$ may be optionally substituted by one or more substituents (e.g. 1, 2 or 3) which may be the same or different, and which are selected from the group consisting of halogen, hydroxy, cyano, nitro, =O, C$_{1-6}$ alkyl, haloC$_{1-6}$ alkyl, —O-haloC$_{1-6}$ alkyl, —O—C$_{1-6}$ alkyl, —SO$_2$R$^4$, —CONR$^4$R$^5$, —NR$^4$COR$^5$, —NR$^4$SO$_2$R$^5$ or —SO$_2$NR$^4$R$^5$; and wherein $R^4$ and $R^5$ are independently selected from hydrogen and C$_{1-6}$ alkyl.

In one embodiment of this aspect, $R^1$ represents unsubstituted —C$_{3-7}$ cycloalkyl (e.g. cyclobutyl, cyclopentyl or cyclohexyl), particularly unsubstituted cyclobutyl.

In an alternative embodiment, $R^1$ represents —C$_{1-6}$alkyl (e.g. ethyl, 1-methylethyl, 2-methylpropyl), particularly 1-methylethyl or 2-methylpropyl.

In another embodiment of this aspect, $R^1$ represents unsubstituted —CH$_2$—C$_{3-7}$ cycloalkyl, particularly cyclopropylmethyl.

In one embodiment of this aspect, the aryl, heteroaryl and heterocyclyl groups of $R^2$ may be optionally substituted by one or more substituents (e.g. 1, 2 or 3) which may be the same or different, and which are selected from the group consisting of halogen, hydroxy, cyano, nitro, =O, C$_{1-6}$ alkyl, —O—C$_{1-6}$ alkyl, haloC$_{1-6}$ alkyl, —O-haloC$_{1-6}$ alkyl and —CONR$^4$R$^5$.

In one embodiment of this aspect, $R^4$, $R^5$ and $R^6$ are independently selected from hydrogen and C$_{1-3}$ alkyl.

In a further embodiment of this aspect, $R^2$ represents:
- aryl (e.g. phenyl) optionally substituted by one or more substituents (e.g. 1, 2 or 3) such as —CONR$^4$R$^5$ (e.g. —CONH$_2$, —CONHMe, —CONMe$_2$), —SO$_2$R$^4$ (e.g. —SO$_2$Me), —NR$^4$SO$_2$R$^5$ (e.g. —NHSO$_2$Me), cyano or halogen (e.g. bromo);
- aryl-heterocyclyl (e.g. phenyl-pyrrolidinyl, phenyl-oxazolidinyl, phenyl-imidazolidinyl, phenyl-morpholinyl, phenyl-piperidinyl) optionally substituted on the heterocyclyl group by one or more (e.g. 1, 2 or 3) substituents such as =O groups and —C$_{1-6}$alkyl (e.g. methyl);
- aryl-heteroaryl (e.g. phenyl-oxadiazolyl) optionally substituted by one or more substituents (e.g. 1, 2 or 3) such as —C$_{1-6}$alkyl (e.g. methyl);
- heteroaryl-heterocyclyl (e.g. pyridinyl-pyrrolidinyl) optionally substituted on the heterocyclyl group by one or more substituents (e.g. 1, 2 or 3) such as =O groups; or -heterocyclyl-heteroaryl (e.g. piperidinyl-pyridinyl) optionally substituted by one or more substituents (e.g. 1, 2 or 3) such as —C$_{1-6}$alkyl (e.g. methyl).

In embodiments in which $R^2$ represents aryl-heterocyclyl or heteroaryl-heterocyclyl and the heterocyclyl group is a nitrogen containing heterocyclyl group, the heterocyclyl group may be linked to the aryl or heteroaryl through a nitrogen atom.

In a more particular embodiment of this aspect, $R^2$ represents:
- aryl (e.g. phenyl) optionally substituted by one or more substituents (e.g. 1, 2 or 3) such as —CONR$^4$R$^5$ (e.g. —CONH$_2$, —CONHMe, —CONMe$_2$), —SO$_2$R$^4$ (e.g. —SO$_2$Me), —NR$^4$SO$_2$R$^5$ (e.g. —NHSO$_2$Me), cyano or halogen (e.g. bromo);
- aryl-heterocyclyl (e.g. -phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as =O groups (e.g. -phenyl-1-pyrrolidin-2-one, -phenyl-3-(1,3-oxazolidin-2-one), -phenyl-3-imidazolidin-2-one, -phenyl-3-imidazolidin-2,4-dione) and —C$_{1-6}$ alkyl (e.g. methyl);
- aryl-heteroaryl (e.g. -phenyl-1,2,4-oxadiazol-5-yl) optionally substituted by one or more substituents (e.g. 1, 2 or 3) such as —C$_{1-6}$alkyl (e.g. methyl);
- heteroaryl-heterocyclyl (e.g. 2-(pyrrolidin-1-yl)-pyridin-5-yl) optionally substituted on the heterocyclyl group by one or more substitutents (e.g. 1, 2 or 3) such as =O groups (e.g. 2-(N-pyrrolidin-2-one)-pyridin-5-yl); or -heterocyclyl-heteroaryl (e.g. –1-(pyridin-3-yl)-piperidin-4-yl) optionally substituted by one or more substitutents (e.g. 1, 2 or 3) such as —C$_{1-6}$alkyl (e.g. methyl).

More particularly, $R^2$ represents:
- aryl (e.g. phenyl) optionally substituted by one or more substituents (e.g. 1, 2 or 3) such as —CONR$^4$R$^5$ (e.g. —CONH$_2$, —CONHMe, —CONMe$_2$), —SO$_2$R$^4$ (e.g. —SO$_2$Me), —NR$^4$SO$_2$R$^5$ (e.g. —NHSO$_2$Me), cyano or halogen (e.g. bromo);
- aryl-heterocyclyl (e.g. -phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as =O groups (e.g. -phenyl-1-pyrrolidin-2-one, -phenyl-3-(1,3-oxazolidin- 2-one), -phenyl-3-imidazolidin-2-one, -phenyl-3-imidazolidin-2,4-dione) and —C$_{1-6}$ alkyl (e.g. methyl); or -heteroaryl-heterocyclyl (e.g. 2-(pyrrolidin-1-yl)-pyridin-5-yl) optionally substituted on the heterocyclyl group by one or more substitutents (e.g. 1, 2 or 3) such as =O groups (e.g. 2-(N-pyrrolidin-2-one)-pyridin-5-yl).

Most particularly, R$^2$ represents:

-aryl-heterocyclyl (e.g. phenyl-pyrrolidin-1-yl, -phenyl-1,3-oxazolidin-3-yl, -phenyl-imidazolidin-3-yl, -phenyl-morpholin-4-yl, phenyl-piperidin-1-yl) optionally substituted on the heterocyclyl group by one or more (e.g. 1, 2 or 3) substituents such as =O groups (e.g. -phenyl-1-pyrrolidin-2-one, -phenyl-3-(1,3-oxazolidin-2-one), -phenyl-3-imidazolidin-2-one, -phenyl-3-imidazolidin-2,4-dione) and —C$_{1-6}$alkyl (e.g. methyl); or -heteroaryl-heterocyclyl (e.g. 2-(pyrrolidin-1-yl)-pyridin-5-yl) optionally substituted on the heterocyclyl group by one or more substitutents (e.g. 1, 2 or 3) such as =O groups (e.g. 2-(N-pyrrolidin-2-one)-pyridin-5-yl).

In a more particular aspect, the present invention provides a compound of formula (I) or a pharmaceutically acceptable salt or solvate thereof, wherein:

R$^1$ represents —C$_{1-6}$ alkyl, —C$_{3-7}$ cycloalkyl or —CH$_2$—C$_{3-7}$ cycloalkyl;

X represents a bond;

R$^2$ represents -aryl, -aryl-heterocyclyl, -aryl-heteroaryl, -heteroaryl-heterocyclyl and -heterocyclyl-heteroaryl;

wherein said aryl, heteroaryl and heterocyclyl groups of R$^2$ may be optionally substituted by one or more substituents (e.g. 1, 2 or 3) which may be the same or different, and which are selected from the group consisting of halogen, hydroxy, cyano, nitro, =O, C$_{1-6}$ alkyl, haloC$_{1-6}$ alkyl, —O-haloC$_{1-6}$ alkyl, —O—C$_{1-6}$ alkyl, —SO$_2$R$^4$, —CONR$^4$R$^5$, —NR$^4$COR$^5$, —NR$^4$SO$_2$R$^5$ or —SO$_2$NR$^4$R$^5$; and wherein R$^4$ and R$^5$ are independently selected from hydrogen and C$_{1-6}$ alkyl.

In another aspect, the present invention provides a compound of formula (I) or a pharmaceutically acceptable salt or solvate thereof, wherein:

R$^1$ represents unsubstituted —C$_{3-7}$ cycloalkyl;

X represents a bond;

R$^2$ represents -aryl, -aryl-aryl, -aryl-heteroaryl, -aryl-heterocyclyl, -heteroaryl, -heteroaryl-aryl, -heteroaryl-heteroaryl, -heteroaryl-heterocyclyl, -heterocyclyl, -heterocyclyl-aryl, -heterocyclyl-heteroaryl or -heterocyclyl-heterocyclyl;

wherein said aryl, heteroaryl and heterocyclyl groups of R$^2$ may be optionally substituted by one or more substituents (e.g. 1, 2 or 3) which may be the same or different, and which are selected from the group consisting of halogen, hydroxy, cyano, nitro, =O, C$_{1-6}$ alkyl, C$_{1-6}$ alkoxy, haloC$_{1-6}$ alkyl, haloC$_{1-6}$ alkoxy and —CONR$^4$R$^5$; and wherein R$^4$ and R$^5$ are independently selected from hydrogen and C$_{1-3}$ alkyl.

In a further aspect, the present invention provides a compound of formula (Ia) or a pharmaceutically acceptable salt or solvate thereof:

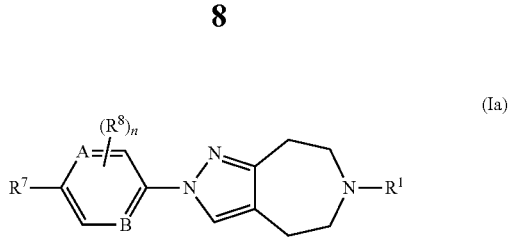

wherein:

R$^1$ represents —C$_{1-6}$ alkyl, —C$_{3-7}$ cycloalkyl or —CH$_2$—C$_{3-7}$ cycloalkyl;

A and B independently represent CH or N;

R$^7$ represents hydrogen, hydroxy, halogen, cyano, nitro, C$_{1-6}$ alkyl, haloC$_{1-6}$ alkyl, —O-haloC$_{1-6}$ alkyl, —O—C$_{1-6}$ alkyl, NR$^{4a}$R$^{5a}$, —CONR$^{4a}$R$^{5a}$, NR$^{4a}$COR$^{5a}$, —SO$_2$R$^{4a}$, —NR$^{4a}$SO$_2$R$^{5a}$ or —SO$_2$NR$^{4a}$R$^{5a}$, wherein R$^{4a}$ and R$^{5a}$ independently represent hydrogen or C$_{1-6}$ alkyl, or wherein NR$^{4a}$R$^{5a}$ may represent a nitrogen containing heterocyclyl group which may optionally be substituted by one or more (e.g. 1, 2 or 3) substituents independently selected from =O and C$_{1-3}$alkyl;

R$^8$ represents hydroxy, halogen, cyano, nitro, C$_{1-6}$ alkyl, haloC$_{1-6}$ alkyl or —O-haloC$_{1-6}$ alkyl, —O—C$_{1-6}$ alkyl; and n represents 0 or 1.

In one embodiment, R$^1$ represents —C$_{3-7}$ cycloalkyl (e.g. cyclobutyl, cyclopentyl or cyclohexyl), particularly unsubstituted cyclobutyl.

In an alternative embodiment, R$^1$ represents —C$_{1-6}$ alkyl (e.g. ethyl, 1-methylethyl, 2-methylpropyl), particularly 1-methylethyl or 2-methylpropyl. More particularly, R$^1$ represents 1-methylethyl.

In an alternative embodiment, R$^1$ represents —CH$_2$—C$_{3-7}$ cycloalkyl, particularly cyclopropylmethyl.

In one embodiment, A represent N and B represents CH. In another embodiment, A and B both represent CH.

In one embodiment, R$^7$ represents hydrogen, halogen, cyano, C$_{1-6}$ alkyl, haloC$_{1-6}$ alkyl, —O-haloC$_{1-6}$ alkyl, —O—C$_{1-6}$ alkyl, —NR$^{4a}$R$^{5a}$CONR$^{4a}$R$^{5a}$, —SO$_2$R$^{4a}$ or —NR$^{4a}$SO$_2$R$^{5a}$ wherein R$^{4a}$ and R$^{5a}$ independently represent hydrogen or C$_{1-6}$ alkyl or wherein NR$^{4a}$R$^{5a}$ represents a nitrogen containing heterocyclyl group which may optionally be substituted by one or more (e.g. 1, 2 or 3) substituents independently selected from =O and C$_{1-3}$ alkyl.

In a more particular embodiment, R$^7$ represents —NR$^{4a}$R$^{5a}$ or —CONR$^{4a}$R$^{5a}$ wherein R$^{4a}$ and R$^{5a}$ independently represent hydrogen or C$_{1-6}$ alkyl or wherein NR$^{4a}$R$^{5a}$ represents a nitrogen containing heterocyclyl group which may optionally be substituted by one or more (e.g. 1, 2 or 3) substituents independently selected from =O and C$_{1-3}$alkyl.

In a more particular embodiment, R$^{4a}$ and R$^{5a}$ independently represent hydrogen or C$_{1-3}$ alkyl.

In another particular embodiment, NR$^{4a}$R$^{5a}$ represents a nitrogen containing heterocyclyl group which may optionally be substituted by one or more (e.g. 1, 2 or 3) substituents independently selected from =O and C$_{1-3}$alkyl.

Even more particularly, R$^7$ represents a nitrogen-containing heterocyclyl group (i.e. NR$^{4a}$R$^{5a}$), for example, a pyrrolidinyl, imidazolidinyl, oxazolidinyl, piperidinyl, morpholinyl group optionally substituted by one or more (e.g. 1, 2 or 3) substituents independently selected from =O and C$_{1-3}$alkyl.

Most particularly, R$^7$ represents pyrrolidinyl, imidazolidinyl or oxazolidinyl optionally substituted by one or more (e.g.

1, 2 or 3) substituents independently selected from =O and C$_{1-3}$alkyl (e.g. —N-pyrrolidin-2-one, —N-oxazolidin-2-one or 3-methyl-imidazolidin-2-one).

In one embodiment, n is 0.

Compounds according to the invention include examples E1-E46 as shown below, or a pharmaceutically acceptable salt or solvate thereof.

More particularly, compounds according to the invention include:
1-[5-(6-Cyclobutyl-5,6,7,8-tetrahydropyrazolo[3,4-d] azepin-2(4H)-yl)-2-pyridinyl]-2-pyrrolidinone;
1-[4-(6-Cyclobutyl-5,6,7,8-tetrahydropyrazolo[3,4-d] azepin-2(4H)-yl)phenyl]-2-pyrrolidinone;
1-{4-[6-(1-Methylethyl)-5,6,7,8-tetrahydropyrazolo[3,4-d] azepin-2(4H)-yl]phenyl}-2-pyrrolidinone;
1-[4-(6-Cyclobutyl-5,6,7,8-tetrahydropyrazolo[3,4-d] azepin-2(4H)-yl)phenyl]-3-methyl-2-imidazolidinone; or
3-[4-(6-Cyclobutyl-5,6,7,8-tetrahydropyrazolo[3,4-d] azepin-2(4H)-yl)phenyl]-1,3-oxazolidin-2-one;

or a pharmaceutically acceptable salt of solvate thereof.

Because of their potential use in medicine, the salts of the compounds of formula (I) are preferably pharmaceutically acceptable.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which may be isolated by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Free base compounds may be converted into the corresponding hydrochloride salts by treatment in methanol or dichloromethane with a solution of hydrogen chloride in diethyl ether followed by evaporation of solvents.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. The different stereoisomeric forms may be separated one from the other by methods known in the art (e.g. separation by chiral HPLC), or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

(a) reacting a compound of formula (II)

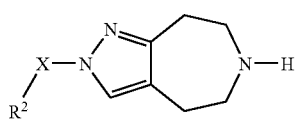

(II)

wherein X and R$^2$ are as defined above, with a compound of formula R$^{1'}$=O, wherein R$^{1'}$ is C$_{1-6}$ alkyl, C$_{3-7}$ cycloalkyl or CH—C$_{3-7}$ cycloalkyl, wherein the cycloalkyl groups may be optionally substituted by C$_{1-3}$ alkyl; or (b) reacting a compound of formula (II)

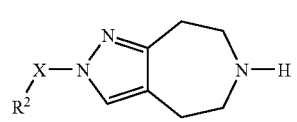

(II)

wherein X and R$^2$ are as defined above, with a compound of formula R$^1$-L$^2$, wherein R$^1$ is as defined above and wherein L$^2$ is a suitable leaving group such as a halogen (e.g. iodine); or (c) reacting a compound of formula (VI)

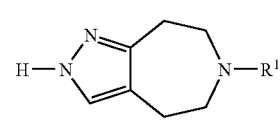

(VI)

wherein R$^1$ is as defined above, with a compound of formula R$^2$—X—B(OH)$_2$ wherein R$^2$ is aryl, aryl-aryl, aryl-heteroaryl, aryl-heterocyclyl, heteroaryl, heteroaryl-aryl, heteroaryl-heteroaryl or heteroaryl-heterocyclyl and X is a bond; or (d) reacting a compound of formula (VI)

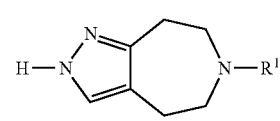

(VI)

wherein R$^1$ is as defined above, with a compound of formula R$^2$—X-L$^1$ wherein R$^2$ is as defined above, wherein X is a bond, and wherein L$^1$ is a suitable leaving group such as a halogen (e.g. bromine); or (e) reacting a compound of formula (VI)

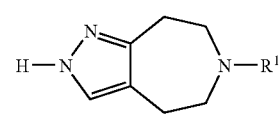

(VI)

wherein R¹ is as defined above, with a compound of formula R²—X-L¹ wherein R² is as defined above, wherein X is —CH₂—, and wherein L¹ is a suitable leaving group such as a halogen (e.g. bromine); or (f) deprotecting a compound of formula (I) which is protected; or (g) interconversion from one compound of formula (I) to another.

Process (a) typically comprises the use of reductive conditions (such as treatment with a borohydride e.g. sodium triacetoxyborohydride), optionally in the presence of an acid, such as acetic acid, in an appropriate solvent such as dichloromethane at a suitable temperature such as room temperature.

Process (b) takes place in a suitable solvent such as ethanol optionally in the presence of a base such as potassium carbonate, at a suitable temperature, such as reflux.

Process (c) typically comprises the use of a copper salt, such as copper (II) acetate in a suitable solvent, such as dichloromethane, at a suitable temperature, for example room temperature, optionally in the presence of molecular sieves and optionally in the presence of a base, for example, pyridine.

When R² is an aryl, aryl-aryl, aryl-heteroaryl, aryl-heterocyclyl, heteroaryl, heteroaryl-aryl, heteroaryl-heteroaryl or heteroaryl-heterocyclyl group, process (d) typically comprises the use of a suitable catalyst system, for example, copper (I) iodide with a diamine ligand such as trans-1,2-diaminocyclohexane, in the presence of a suitable base, for example, potassium phosphate, in a suitable solvent, for example, dioxan at a suitable temperature, for example, heating at reflux. When R² is a heterocyclyl, heterocyclyl-aryl. heterocyclyl-heteroaryl or heterocyclyl-heterocyclyl group, process (d) typically comprises the use of a base, such as, sodium hydride, in a suitable solvent, such as dimethylformamide, at a suitable temperature, for example, heating at 60-70° C.

Process (e) typically comprises the use of a base, such as, sodium hydride, in a suitable solvent, such as dimethylformamide, at a suitable temperature, for example, heating at 60-70° C.

In process (f), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxan or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—COCF₃) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (g) may be performed using conventional interconversion procedures such as epimerisation, oxidation, reduction, alkylation, nucleophilic or electrophilic aromatic substitution, ester and nitrile hydrolysis, amide bond formation or transition metal mediated coupling reactions. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidation reactions between organic electrophiles (such as aryl halides) and nucleophiles such as amides; and Copper mediated coupling reactions between phenols and boronic acids.

Compounds of formula (II) where R² is an aryl, aryl-aryl, aryl-heteroaryl, aryl-heterocyclyl, heteroaryl, heteroaryl-aryl, heteroaryl-heteroaryl or heteroaryl-heterocyclyl group and X is a bond may be prepared in accordance with the following scheme:

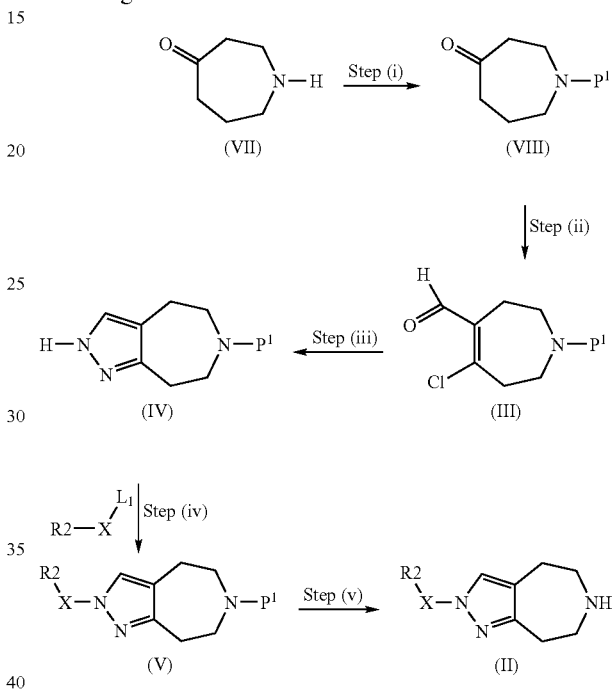

wherein P¹ represents a suitable protecting group such as benzyl, X represents a bond and L₁ represents a suitable leaving group, for example, bromine.

When P¹ represents benzyl, step (i) comprises reacting a compound of formula (VII) with benzaldehyde. The reaction typically comprises the use of reductive conditions (such as treatment with a borohydride e.g. sodium triacetoxyborohydride), optionally in the presence of a base (e.g. triethylamine) in a suitable solvent such as dichloromethane at a suitable temperature such as between 0° C. and room temperature.

Step (ii) typically takes place in the presence of phosphorous oxychloride and dimethylformamide at a suitable temperature such as between 0° C. and room temperature.

Step (iii) typically comprises a cyclisation reaction with hydrazine (e.g. hydrazine hydrate), in a suitable solvent, such as ethanol, at a suitable temperature, for example reflux, with the optional addition of a catalytic amount of acid, such as aqueous hydrochloric acid.

It will be appreciated that prior to the cyclisation reaction, the compound of formula (III) may be reacted to with hydroxylamine hydrochloride in a suitable solvent such as ethanol, and a suitable temperature such as room temperature to form the corresponding oxime.

Step (iv) typically comprises the use of a suitable catalyst system, for example, copper (I) iodide with a diamine ligand such as trans-1,2-diaminocyclohexane, in the presence of a suitable base, for example, potassium phosphate, in a suitable solvent, for example, dioxan at a suitable temperature, for example, heating at reflux as described in process (d).

Step (v) is a deprotection reaction. When $P^1$ represents benzyl, step (v) may be performed using a suitable catalyst, for example, palladium on charcoal, in a suitable solvent such as ethanol, under a pressure of hydrogen, for example, one atmosphere of hydrogen.

When $P^1$ represents 1,1-dimethylethyl carboxylate, compounds of formula (IV) may alternatively be prepared in accordance with the following scheme:

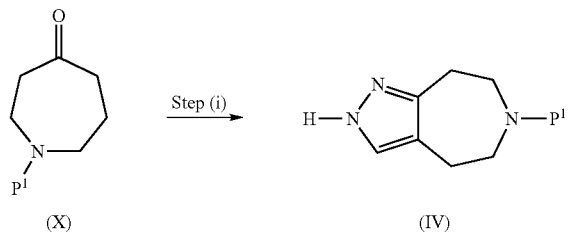

Step (i) typically comprises reaction with lithium diisopropylamide and ethyl formate in a suitable solvent such as tetrahydrofuran, at a suitable temperature such as room temperature, followed by a cyclisation reaction with hydrazine (e.g. hydrazine hydrate) optionally in the presence of acid, in a suitable solvent, such as ethanol, at a suitable temperature, for example reflux.

Compounds of formula (II) may be prepared from compounds of formula (IV) prepared using this protecting group. However, as will be apparent to the skilled reader, when $P^1$ represents 1,1-dimethylethyl carboxylate, the deprotection reaction may be performed by treatment with trifluoroacetic acid in dichloromethane or 4M HCl in dioxan, at a suitable temperature such as room temperature.

Compounds of formula (V) where $R^2$ is an aryl, aryl-aryl, aryl-heteroaryl, aryl-heterocyclyl, heteroaryl, heteroaryl-aryl, heteroaryl-heteroaryl or heteroaryl-heterocyclyl group and X is a bond may alternatively be prepared in accordance with the following scheme:

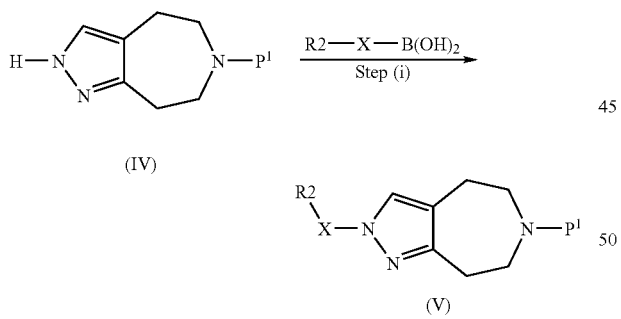

wherein $P^1$ represents a suitable protecting group such as benzyl and the $R_2$—X—$B(OH)_2$ group, is an aryl or heteroaryl boronic acid (i.e. X is a bond).

Step (i) typically comprises the use of a copper salt, such as copper (II) acetate in a suitable solvent, such as dichloromethane, at a suitable temperature, for example room temperature, optionally in the presence of molecular sieves and optionally in the presence of a base, for example pyridine, in the manner described above for process (c).

Compounds of formula (II) wherein $R^2$ is a heterocyclyl, heterocyclyl-aryl, heterocyclyl-heteroaryl or heterocyclyl-heterocyclyl group and X is a bond may be prepared as described above, using compounds of formula (V) where $R^2$ is a heterocyclyl, heterocyclyl-aryl, heterocyclyl-heteroaryl or heterocyclyl-heterocyclyl group and X is a -bond.

Compounds of formula (V) where $R^2$ is a heterocyclyl, heterocyclyl-aryl, heterocyclyl-heteroaryl or heterocyclyl-heterocyclyl and X is a bond may be prepared in accordance with the following scheme:

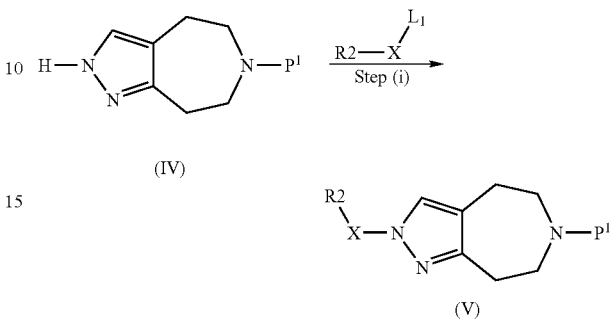

wherein $P^1$ represents a suitable protecting group such as benzyl, X represents a bond and $L_1$ represents a leaving group such as bromine.

Step (i) typically comprises the use of a base, such as, sodium hydride, in a suitable solvent, such as dimethylformamide, at a suitable temperature, for example, heating at 60-70° C. as described in process (d).

Compounds of formula (II) wherein $R^2$ is an aryl, aryl-aryl, aryl-heteroaryl, aryl-heterocyclyl, heteroaryl, heteroaryl-aryl, heteroaryl-heteroaryl or heteroaryl-heterocyclyl group and X is —$CH_2$— may be prepared as described above, using compounds of formula (V) where $R^2$ is an -aryl, -aryl-aryl, -aryl-heteroaryl, -aryl-heterocyclyl, -heteroaryl, -heteroaryl-aryl, -heteroaryl-heteroaryl, -heteroaryl-heterocyclyl, -heterocyclyl, -heterocyclyl-aryl, -heterocyclyl-heteroaryl or -heterocyclyl-heterocyclyl group and X is a —$CH_2$— group.

Compounds of formula (V) where $R^2$ is an -aryl, -aryl-aryl, -aryl-heteroaryl, -aryl-heterocyclyl, -heteroaryl, -heteroaryl-aryl, -heteroaryl-heteroaryl, -heteroaryl-heterocyclyl, -heterocyclyl, -heterocyclyl-aryl, -heterocyclyl-heteroaryl or -heterocyclyl-heterocyclyl group and X is a —$CH_2$— group may be prepared in accordance with the following scheme:

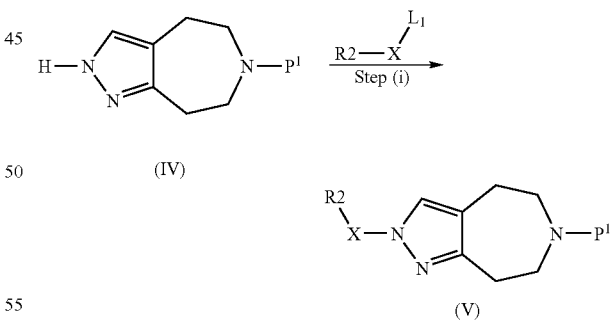

wherein $P^1$ represents a suitable protecting group such as benzyl, X represents —$CH_2$— and $L_1$ represents a leaving group such as bromine.

Step (i) typically comprises the use of a base, such as, sodium hydride, in a suitable solvent, such as dimethylformamide, at a suitable temperature, for example, heating at 60-70° C. as described in process (e).

Compounds of formula (V) wherein $R^2$ and X are as defined above, may alternatively be prepared in accordance with the following scheme:

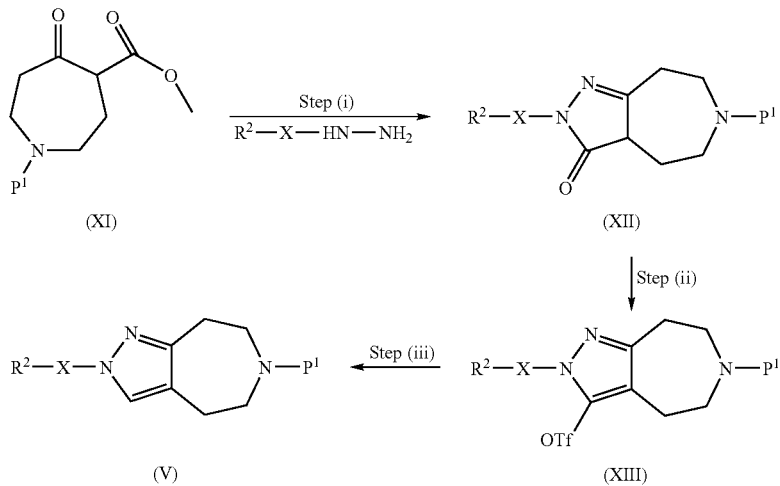

(XI) → (XII) → (XIII) → (V)

wherein P¹ represents a suitable protecting group such as 1,1-dimethylethyl carboxylate, wherein R² and X are as defined above and wherein —OTf represents a triflate group.

Where R²—X—HN—NH₂ is a hydrochloride salt, step (i) typically comprises the use of a base such as triethylamine in a suitable solvent such as tert-butanol, and a suitable temperature, such as reflux.

Step (ii) comprises reaction with diisopropylethylamine and 1,1,1-trifluoro-N-phenyl-N-[(trifluoromethyl)sulfonyl]methanesulfonamide in a suitable solvent, such as dichloromethane, at a suitable temperature such as reflux.

Step (iii) comprises treatment with a base (e.g., triethylamine) in the presence of a suitable catalyst, such as palladium on carbon in a suitable solvent such as a mixture of ethyl acetate and methanol at a suitable temperature such as room temperature under a pressure of hydrogen, for example, one atmosphere of hydrogen.

Compounds of formula (VI) may be prepared in accordance with the following scheme wherein P¹ represents a suitable protecting group such as benzyl:

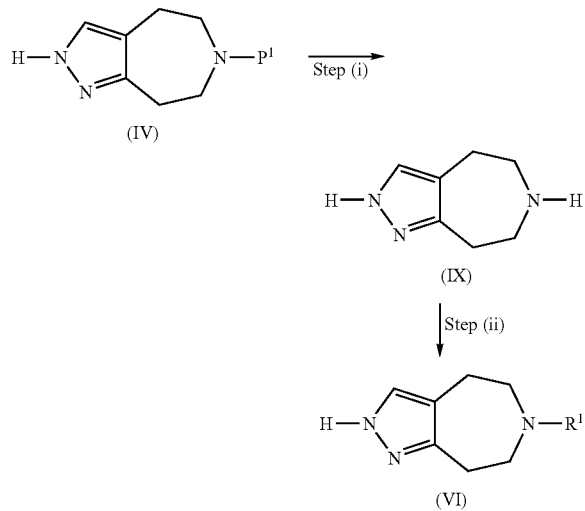

(IV) → (IX) → (VI)

Step (i) is a deprotection reaction. When P¹ is benzyl, step (i) may be performed using a suitable catalyst, for example, palladium on charcoal, in a suitable solvent such as ethanol, under a pressure of hydrogen, for example, one atmosphere of hydrogen.

Step (ii) may be carried out as described above for process (a).

The compounds of formula (VII) and (XI) may be prepared as described in Synthetic Communications (1992), 22(9): 1249-58. Compounds of formula (III) may be prepared according to DE 3105858.

Compounds of formula (X), $R^{1'}$=O, $R^1$-$L^2$, $R^2$—X—B(OH)₂ (wherein X represents a bond), $R^2$—X-$L^1$ (wherein X represents a bond or —CH₂—) and $R^2$—X—HN—NH₂ (wherein X and $R^2$ are as defined above) are either commercially available or may be prepared from commercially available compounds using standard methodology.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia (including Lewy body dementia and vascular dementia), age-related memory dysfunction, mild cognitive impairment, cognitive deficit, epilepsy, pain of neuropathic origin including neuralgias, neuritis and back pain, and inflammatory pain including osteoarthritis, rheumatoid arthritis, acute inflammatory pain and back pain, migraine, Parkinson's disease, multiple sclerosis, stroke and sleep disorders (including narcolepsy and sleep deficits associated with Parkinson's disease); psychiatric disorders including schizophrenia (particularly cognitive deficit of schizophrenia), attention deficit hyperactivity disorder, depression, anxiety and addiction; and other diseases including obesity and gastro-intestinal disorders.

It will also be appreciated that compounds of formula (I) are expected to be selective for the histamine H3 receptor over other histamine receptor subtypes, such as the histamine H1 receptor. Generally, compounds of the invention may be at least 10 fold selective for H3 over H1, such as at least 100 fold selective.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example medicaments claimed to be useful as either disease modifying or symptomatic treatments of Alzheimer's disease. Suitable examples of such other therapeutic agents may be agents known to modify cholinergic transmission such as 5-$HT_6$ antagonists, M1 muscarinic agonists, M2 muscarinic antagonists or acetylcholinesterase inhibitors. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.1 to 200 mg and even more suitably 1.0 to 200 mg. In one aspect, a suitable unit dose would be 0.1-50 mg. Such unit doses may be administered more than once a day, for example two or three a day. Such therapy may extend for a number of weeks or months.

The following Descriptions and Examples illustrate the preparation of compounds of the invention.

Description 1

1-(Phenylmethyl)hexahydro-4H-azepin-4-one hydrochloride (D1)

Method A

Hexahydro-4H-azepin-4-one hydrochloride (10 g, 66.9 mmol); (may be prepared as described in Synthetic Communications (1992), 22(9), 1249-58) was suspended in dichloromethane (100 ml) and triethylamine (9.31 ml, 66.9 mmol) added, followed by benzaldehyde (68 ml, 0.669 mol). The mixture was stirred at room temperature for 30 minutes under argon, then cooled in ice whilst sodium triacetoxyborohydride (17 g, 80 mmol) was added portionwise. The mixture was stirred and allowed to reach room temperature, then stirred for 2 hours. 2M sodium hydroxide solution (80 ml) was added, the layers separated and the aqueous layer extracted with dichloromethane (×2). The combined organic extracts were evaporated to half volume, then extracted with 2M hydrochloric acid (2×100 ml). The aqueous layer was made basic with 50% sodium hydroxide solution and extracted with dichloromethane (×2). The combined organic extracts were dried over magnesium sulphate and evaporated to afford the title compound (D1). $^1$H NMR (DMSO-d6) δ 1.99-2.02 (1H, m), 2.14-2.24 (1H, m), 2.51-2.53 (1H, m) 2.58-2.70 (2H, m) 3.05-3.13 (1H, s) 3.18-3.37 (2H, m), 3.48-3.51 (2H, m), 4.37 (2H, d) 7.46-7.47 (3H, m) 7.65-7.67 (2H, m) 11.35 (1H, bs).

Method B

A suspension of hexahydro-4H-azepin-4-one hydrochloride (5 g, 33.4 mmol) (may be prepared as described in Synthetic Communications (1992), 22(9), 1249-58) in dichloromethane (50 ml) was treated with benzaldehyde (34 ml, 33.4 mmol) and triethylamine (4.66 ml, 33.4 mmol) and allowed to stir at room temperature for approximately 10 minutes. Sodium triacetoxyborohydride (10.6 g, 50.1 mmol) was added and the mixture stirred at room temperature for 4 hours. After this time the reaction was quenched with 2M NaOH solution (~50 ml) and extracted with dichloromethane (2×200 ml), washed with brine, dried over magnesium sulphate, evaporated and purified by column chromatography on silica gel, eluting with a mixture of 2M ammonia in methanol and dichloromethane (0-4%). The HCl salt was formed using 1.1 equivalents of 1 M HCl in diethyl ether affording the title compound (D1). MS (ES+) m/e 204 [M+H]$^+$.

Description 2

1-(Phenylmethyl)hexahydro-4H-azepin-4-one (D2)

Hexahydro-4H-azepin-4-one hydrochloride (10 g, 66.9 mmol); (may be prepared as described in Synthetic Communications (1992), 22(9), 1249-58) was suspended in dichloromethane (100 ml) and triethylamine (9.31 ml, 66.9 mmol) added, followed by benzaldehyde (68 ml, 0.669 mol). The mixture was stirred at room temperature for 30 minutes under argon, then cooled in ice whilst sodium triacetoxyborohydride (17 g, 80 mmol) was added portionwise. The mixture was stirred and allowed to reach room temperature, then stirred for 2 hours. 2M sodium hydroxide solution (80 ml) was added, the layers separated and the aqueous layer extracted with dichloromethane (×2). The combined organic extracts were evaporated to half volume, then extracted with 2M hydrochloric acid (2×100 ml). The aqueous layer was made basic with 50% sodium hydroxide solution and extracted with dichloromethane (×2). The combined organic extracts were dried over magnesium sulphate and evaporated to afford the title compound (D2). $^1$H NMR (CDCl$_3$) δ 1.82-1.88 (2H, m), 2.52-2.55 (2H, m), 2.59-2.62 (2H, m) 2.71-2.76 (4H, m) 3.65 (1H, s) 7.23-7.33 (5H, m).

Description 3

5-Chloro-1-(phenylmethyl)-2,3,6,7-tetrahydro-1H-azepine-4-carbaldehyde (D3)

Method A

Dimethylformamide (6.4 ml, 83.5 mmol) was added to dichloromethane (90 ml) under argon and cooled to 0° C. Phosphorus oxychloride (6.24 ml, 67.05 mmol) was added dropwise and the mixture stirred at 0° C. for 2 hours. 1-(Phenylmethyl)hexahydro-4H-azepin-4-one hydrochloride (may be prepared as described in Description 1) (10 g, 41.72 mmol) was added portionwise to the above mixture at 0° C. over 10 minutes. The mixture was stirred at 0° C. for 45 minutes then allowed to warm to room temperature and stirred overnight. The reaction was poured portionwise into sodium acetate (100 g) in water (800 ml). The resulting mixture was adjusted to pH10 with 2M sodium hydroxide solution then separated. The aqueous layer was extracted with dichloromethane (×2) and the combined organic extracts washed with brine, dried over magnesium sulphate and evaporated to give the title compound which may be used without further purification (D3). MS (ES+) m/e 250, 252 [M+H]$^+$ Method B Dimethylformamide (10.11 ml, 132 mmol) was added to dichloromethane (140 ml) under argon and cooled to 0° C. Phosphorus oxychloride (9.87 ml, 106 mmol) was added dropwise and the mixture stirred at 0° C. for 2 hours. 1-(Phenylmethyl)hexahydro-4H-azepin-4-one (may be prepared as described in Description 2) (13.4 g, 65.95 mmol) was dissolved in dichloromethane (40 ml) and added dropwise over 10 minutes to the above mixture at 0° C. The mixture was stirred at 0° C. for 45 minutes then allowed to warm to room temperature and stirred overnight. The reaction was poured portionwise into sodium acetate (130 g) in water (1 l). The resulting mixture was adjusted to pH10 with 2M sodium hydroxide solution then separated. The aqueous layer was extracted with dichloromethane (×2) and the combined organic extracts washed with brine, dried over magnesium sulphate and evaporated to give the title compound which may be used without further purification (D3). MS (ES+) m/e 250, 252 [M+H]$^+$ Method C To a solution of dimethylformamide (385 μL, 5 mmol) in anhydrous dichloromethane (6 ml) in an ice bath was added very slowly phosphorus oxychloride (374 μl, 4 mmol). The resulting mixture was allowed to stir in an ice bath for 3 hours. After this time, 1-(phenylmethyl)hexahydro-4H-azepin-4-one hydrochloride (may be prepared as described in Description 1) (600 mg, 2.5 mmol) was added portion wise and then the reaction mixture was allowed to stir at room temperature overnight. The next day, the mixture was slowly added to a vigorously stirred mixture of sodium acetate (6 g, 73.2 mol) in ice-water (60 ml). The resulting mixture was adjusted to pH 10 by using 2M NaOH and extracted with dichloromethane (3×60 ml). The organic layer was combined and washed with NaHCO$_3$ and brine, dried over MgSO$_4$ and evaporated. The resulting crude mixture of the title compound may be used without further purification (D3); MS (ES+) m/e 250 [M+H]+.

Description 4

5-Chloro-1-(phenylmethyl)-2,3,6,7-tetrahydro-1H-azepine-4-carbaldehyde oxime (D4)

A solution of 5-chloro-1-(phenylmethyl)-2,3,6,7-tetrahydro-1H-azepine-4-carbaldehyde (may be prepared as described in Description 3) (11.6 g, 46.5 mmol) in ethanol (100 ml) was stirred with hydroxylamine hydrochloride (3.23 g, 46.5 mmol) at room temperature for 72 hours. The ethanol was removed by evaporation and the residue partitioned between ethyl acetate and a saturated solution of sodium bicarbonate. The ethyl acetate was washed with water & brine, then dried and evaporated to afford the title compound (D4); MS (ES+) m/e 265 & 267 [M+H]+.

Description 5

6-(Phenylmethyl)-2,4,5,6,7,8-hexahydropyrazolo[3,4-d]azepine (D5)

Method A

To a solution of 5-chloro-1-(phenylmethyl)-2,3,6,7-tetrahydro-1H-azepine-4-carbaldehyde (may be prepared as described in Description 3) (10.4 g, 41.8 mmol) in ethanol (30 ml) was added a catalytic amount of 2M hydrochloric acid (5 drops), followed by hydrazine hydrate (2.43 ml, 50.2 mmol). The resulting mixture was heated at reflux for 48 hours and concentrated in vacuo. The resulting crude mixture was diluted with water, basified using a saturated solution of sodium bicarbonate and extracted into ethyl acetate. The extracts were combined, washed with brine, dried over magnesium sulphate and concentrated in vacuo. The product was purified by chromatography on silica, eluting with a mixture of 2M ammonia in methanol/dichloromethane (2-4%) to afford the title compound (D5). MS (ES+) m/e 228 [M+H]+.

Method B

5-Chloro-1-(phenylmethyl)-2,3,6,7-tetrahydro-1H-azepine-4-carbaldehyde (may be prepared as described in Description 3) (assumed 41.72 mmol), hydrazine hydrate (2.23 ml, 45.89 mmol) and 2M hydrochloric acid (5 drops) were stirred in ethanol (100 ml) and heated to reflux for 76 hours. The solvent was evaporated and the residue partitioned between ethyl acetate and water and made basic by addition of sodium bicarbonate. The aqueous phase was extracted with ethyl acetate and the combined organic layers washed with brine, dried over magnesium sulphate and evaporated. The residue was purified by flash chromatography, eluting with 2-4% 2M ammonia in methanol/dichloromethane to give the title compound (D5). MS (ES+) m/e 228 [M+H]+

Method C

To a suspension of 5-chloro-1-(phenylmethyl)-2,3,6,7-tetrahydro-1H-azepine-4-carbaldehyde oxime (may be prepared as described in Description 4) (400 mg, 1.51 mmol) in ethanol (8 ml) and hydrochloric acid (4 drops) was added hydrazine hydrate (8 ml). The resulting suspension was heated at reflux over the weekend. The mixture was allowed to cool to room temperature and treated with excess acetone. Extracted with 2×100 ml of ethyl acetate. The aqueous was basified using sodium bicarbonate solution and re-extracted with ethyl acetate. The combined extracts were dried, evaporated, and dissolved in dichloromethane and applied to two 10 g SCX cartridges, eluting with methanol then a 2M solution of ammonia in methanol. The basic fractions were combined, evaporated and purified by column chromatography eluting with a mixture of 2M ammonia in methanol and dichloromethane (0-5%) to afford the product (D5); MS (ES+) m/e 228 [M+H]+.

Method D

To a suspension of 5-chloro-1-(phenylmethyl)-2,3,6,7-tetrahydro-1H-azepine-4-carbaldehyde oxime (may be prepared as described in Description 4) (200 mg, 0.76 mmol) in ethanol (2 ml) and hydrochloric acid (1 drop) was added hydrazine hydrate (2 ml). The resulting suspension was heated to reflux for 15 minutes and then overnight. A further 2 ml of hydrazine hydrate was added and refluxing continued for 1 hour. The reaction mixture was allowed to cool, quenched with acetone, washed with water and re-extracted with ethyl acetate (3×50 ml). The combined extracts were dried over magnesium sulphate and purified by column chromatography eluting with a mixture of 2M ammonia in methanol and dichloromethane (0-3%) to afford the product (D5); $^1$H-NMR (MeOD) δ 2.68-2.70 (2H, m), 2.78 (4H, m), 2.84-2.87 (2H, m), 3.80 (2H, s), 7.23-7.27 (2H, m), 7.31-7.34 (2H, m), 7.38-7.40 (2H, m).

Method E

A solution of 5-chloro-1-(phenylmethyl)-2,3,6,7-tetrahydro-1H-azepine-4-carbaldehyde (may be prepared as described in Description 3) (10.41 g, 41.8 mmol) in ethanol (30 ml) and hydrochloric acid (5 drops) was treated with hydrazine hydrate (2.43 ml, 50.2 mmol) and heated at reflux overnight. The reaction mixture was evaporated to give a viscous oil which was redissolved in ethanol (30 ml) and heated at reflux for 27 hours in total. After cooling to room temperature the mixture was evaporated, dissolved in water and ethyl acetate, basified using sodium bicarbonate and extracted with ethyl acetate (3×150 ml). The combined extracts were washed with brine, dried over magnesium sulphate, evaporated and purified by column chromatography eluting with a mixture of 2M ammonia in methanol and dichloromethane (2-4%) to afford the product (D5); MS (ES+) m/e 228 [M+H]+.

Method F

A solution of 5-chloro-1-(phenylmethyl)-2,3,6,7-tetrahydro-1H-azepine-4-carbaldehyde (may be prepared as described in Description 3) (1.73 g, 6.95 mmol) in ethanol (10 ml) was treated with hydrazine hydrate (0.37 ml, 7.64 mmol) and heated at reflux for 18 hours and then a further 2 days. After cooling to room temperature the mixture was filtered and the filtrate evaporated and dissolved in water. The pH was adjusted to 8 using sodium bicarbonate, followed by extraction with ethyl acetate. The combined extracts were dried over magnesium sulphate, evaporated and purified by column chromatography eluting with a mixture of 2M ammonia in methanol and dichloromethane (2-4%) to afford the product (D5); MS (ES+) m/e 228 [M+H]+.

Method G

To a solution of 5-chloro-1-(phenylmethyl)-2,3,6,7-tetrahydro-1H-azepine-4-carbaldehyde (may be prepared as described in Description 3) (500 mg, 0.2 mmol) in ethanol (5 ml) and 2M HCl (3 drops) was slowly added hydrazine hydrate (106 μl, 2.2 mmol). The resulting mixture was refluxed under argon, overnight. The next day, the mixture was evaporated to dryness, dissolved in 40 ml of water, adjusted to pH 8 using sodium bicarbonate and extracted with 3×50 mL of ethyl acetate. The organic layers were combined then washed with brine and dried over MgSO$_4$ and evaporated. The resulting crude was purified using silica gel chromatography to afford the title product (D5); MS (ES+) m/e 228 [M+H]+ and 7-(phenylmethyl)-2,4,5,6,7,8-hexahydropyrazolo[3,4-c]azepine as a (85:15) mixture.

Description 6

2,4,5,6,7,8-Hexahydropyrazolo[3,4-d]azepine hydrochloride (D6)

6-(Phenylmethyl)-2,4,5,6,7,8-hexahydropyrazolo[3,4-d] azepine (may be prepared as described in Description 5) (5.52 g, 24.29 mmol) was dissolved in ethanol (70 ml) under argon and 2M hydrochloric acid (12.2 ml, 24.4 mmol) added, followed by 50% wet 10% palladium on carbon catalyst (1 g). The mixture was stirred under an atmosphere of hydrogen for 18 hours. The catalyst was filtered and the filtrate evaporated to give the title compound (D6). MS (ES+) m/e [M+H]+

Description 7

2,4,5,6,7,8-Hexahydropyrazolo[3,4-d]azepine (D7)

Method A 6-(Phenylmethyl)-2,4,5,6,7,8-hexahydropyrazolo[3,4-d] azepine (may be prepared as described in Description 5) (390 mg, 1.72 mmol) was dissolved in ethanol (8 ml), treated with palladium (100 mg, 10% on charcoal paste) and the reaction mixture was stirred at room temperature under hydrogen (atmospheric pressure) for 18 hours. The mixture was filtered through celite and the filtrate evaporated under reduced pressure to afford the title compound (D7). MS (ES+) m/e 138 [M+H]+.

Method B 6-(Phenylmethyl)-2,4,5,6,7,8-hexahydropyrazolo[3,4-d] azepine (may be prepared as described in Description 5) (2.8 g, 12.3 mmol) was dissolved in ethanol, treated with palladium on carbon (10% paste) (718 mg, 1.23 mmol) and hydrogenated at atmospheric pressure and room temperature for 42 hours. The mixture was filtered through celite and evaporated under reduced pressure to afford the product (D7); MS (ES+) m/e 138 [M+H]+.

Method C 1,1-Dimethylethyl 4,5,7,8-tetrahydropyrazolo[3,4-d] azepine-6(2H)-carboxylate (may be prepared as described in Description 9) (1.4 g, 5.9 mmol) in dichloromethane (2 ml) was treated with trifluoroacetic acid (2 ml). After 1 hour the mixture was reduced, dissolved in methanol and applied to a SCX ion exchange cartridge and washed with methanol and then 2M solution of ammonia in methanol. The ammonia containing fractions were then combined and reduced and the resulting residue was chromatographed on silica gel eluting with a 1:99 rising to 20:80 mixture of 2M ammonia in methanol and dichloromethane to furnish the title compound (D7); (MS (ES+): [M+H]+ at m/z 138.12

Description 8

1,1-Dimethylethyl 4-formyl-5-oxohexahydro-1H-azepine-1-carboxylate (D8)

1,1-Dimethylethyl 4-oxohexahydro-1H-azepine-1-carboxylate (commercially available from e.g. Magic Chemicals) (2.0 g, 9.4 mmol) in tetrahydrofuran at −78° C. was treated with a 2M solution of lithium diisopropylamide (4.7 ml, 9.4 mmol) in tetrahydrofuran. After 20 minutes neat ethyl formate (0.7 g, 9.4 mmol) was added and the reaction mixture was allowed to warm to room temperature. After 2 hours the reaction was quenched, poured into water and extracted several times with ethyl acetate. The combined organic layers were then dried and reduced in vacuo to furnish the title compound which may be used without further purification (D8).

Description 9

1,1-Dimethylethyl 4,5,7,8-tetrahydropyrazolo[3,4-d] azepine-6(2H)-carboxylate (D9)

Method A 2,4,5,6,7,8-Hexahydropyrazolo[3,4-d]azepine hydrochloride (may be prepared as described in Description 6) (4.1 g, 23.58 mmol) was suspended in 1:1 tetrahydrofuran and dimethylformamide (100 ml) and cooled to 0° C. Triethylamine (6.6 ml, 47.16 ml) was added, followed by di-tert-butyl dicarbonate (5.14 g, 23.58 mmol). The mixture was stirred and allowed to warm to room temperature over 2 hours, then evaporated. The residue was dissolved in diethyl ether and washed with water (×3). The organic layer was dried over magnesium sulphate and evaporated. The residue was purified by flash chromatography, eluting with 2-4% 2M ammonia in methanol/dichloromethane to give the title compound (D9). MS (ES+) m/e 182 [M-tBu]+

Method B 2,4,5,6,7,8-Hexahydropyrazolo[3,4-d]azepine (may be prepared as described in Description 7) (250 mg, 1.82 mmol) was suspended in tetrahydrofuran (5 ml), treated with triethylamine (0.25 ml, 1.82 mmol) and bis(1,1-dimethylethyl)dicarbonate (397 mg, 1.82 mmol) and the resulting mixture was stirred at room temperature under argon for 2 hours. The solvent was removed under reduced pressure and the product purified by chromatography on silica, eluting with a mixture of 2M ammonia in methanol/dichloromethane (2-5%) to afford the title compound (D9). MS (ES+) m/e 182 [M-tBu]+.

Method C

A solution of 2,4,5,6,7,8-hexahydropyrazolo[3,4-d] azepine (may be prepared as described in Description 7) (800 mg, 5.84 mmol) in tetrahydrofuran (10 ml) was treated with triethylamine (815 μl, 5.84 mmol) and bis(1,1-dimethylethyl) dicarbonate (1.27 g, 5.84 mmol), then stirred at room temperature for 2 hours under argon. After the solvent was evaporated in vacuo, the residue was purified by chromatography on silica gel, eluting with a mixture of 2M ammonia in methanol/dichloromethane (0-10%), to afford the title compound (D9). MS (ES+) m/e 238 [M+H]+.

Method D 1,1-Dimethylethyl 4-formyl-5-oxohexahydro-1H-azepine-1-carboxylate (may be prepared as described in Description 8) (crude material, approximately 9.4 mmol) in ethanol (20 ml) was treated with hydrazine hydrate (1.4 g, 30 mmol). The mixture was heated at reflux for 2 hours before being cooled to room temperature and reduced in vacuo. The crude product was then purified on silica gel eluting with a ethyl acetate to furnish the title compound (D9); (MS (ES+): [M+H]⁺ at m/z 238.18

Description 10

1,1-Dimethylethyl 2-(4-cyanophenyl)-4,5,7,8-tetrahydropyrazolo[3,4-d]azepine-6(2H)-carboxylate (D10)

1,1-Dimethylethyl 4,5,7,8-tetrahydropyrazolo[3,4-d]azepine-6(2H)-carboxylate (may be prepared as described in Description 9) (1.80 g, 7.58 mmol), 4-cyanophenyl boronic acid (2.23 g, 15.16 mmol; commercially available from e.g. Aldrich), copper(II) acetate (4.15 g, 22.76 mmol), pyridine (1.21 ml, 15.16 mmol) and powdered 4 Å molecular sieves (5.33 g) were stirred in dichloromethane (80 ml) at room temperature in air for 40 hours. The mixture was filtered through a pad of Kieselguhr and the filtrate evaporated. The residue was dissolved in ethyl acetate and the solution washed with 5% sodium bicarbonate solution (×3), dried over magnesium sulphate and evaporated. The residue was purified by flash chromatography eluting with 10-40% ethyl acetate in n-pentane to give the title compound (D10). MS (ES+) m/e 339 [M+H]⁺

Description 11

4-(5,6,7,8-Tetrahydropyrazolo[3,4-d]azepin-2(4H)-yl)benzonitrile (D11)

1,1-Dimethylethyl 2-(4-cyanophenyl)-4,5,7,8-tetrahydropyrazolo[3,4-d]azepine-6(2H)-carboxylate (may be prepared as described in Description 10) (150 mg, 0.443 mmol) was dissolved in 1,4-dioxan (ml) and 4M hydrogen chloride in 1,4-dioxan (3 ml) added. The mixture was stirred at room temperature for 2 hours. Methanol was added and the mixture purified on 10 g SCX column, eluting initially with methanol, than with 2M ammonia in methanol. Evaporation of the basic fractions gave the title compound (D11). MS (ES+) m/e 239 [M+H]⁺

Description 12

1,1-Dimethylethyl 2-(4-bromophenyl)-4,5,7,8-tetrahydropyrazolo[3,4-d]azepine-6(2H-carboxylate (D12)

Method A 1,1-Dimethylethyl 4,5,7,8-tetrahydropyrazolo[3,4-d]azepine-6(2H)-carboxylate (may be prepared as described in Description 9) (964 mg, 4.06 mmol), 4-bromophenyl boronic acid (1.64 g, 8.12 mmol; commercially available from e.g. Aldrich), copper(II) acetate (2.22 g, 12.18 mmol), pyridine (0.646 ml, 8.12 mmol) and powdered 4 Å molecular sieves (2.85 g) were stirred in dichloromethane (40 ml) at room temperature in air for 64 hours. The mixture was filtered through a pad of Kieselguhr and the filtrate evaporated. The residue was dissolved in ethyl acetate and the solution washed with 5% sodium bicarbonate solution (×2), dried over magnesium sulphate and evaporated. The residue was purified by flash chromatography eluting with 10-30% ethyl acetate in n-pentane to give the title compound (D12). MS (ES+) m/e 392, 394 [M+H]⁺

Method B 1,1-Dimethylethyl 4,5,7,8-tetrahydropyrazolo[3,4-d]azepine-6(2H)-carboxylate (may be prepared as described in Description 9) (254 mg, 1.07 mmol), (4-bromophenyl)boronic acid (431 mg, 2.14 mmol; commercially available from e.g. Aldrich), copper acetate (583 mg, 3.21 mmol), pyridine (0.17 ml, 2.14 mmol) and 4 angstrom molecular sieves (0.75 g) were added together in dichloromethane (10 ml) and the resulting mixture was stirred at room temperature under air for 18 hours. The mixture was heated at 40° C. for 7 hours. The mixture was allowed to cool to room temperature and stirred for 18 hours. The mixture was filtered through celite and the solvent evaporated. The residue was dissolved in ethyl acetate and washed with saturated sodium bicarbonate solution. The ethyl acetate layer was separated, dried under magnesium sulfate and evaporated. The product was purified by column chromatography eluting with a mixture of ethyl acetate/pentane (1:9 to 1:4) to afford the title compound (D12). MS (ES+) m/e 392 & 394 [M+H]⁺.

Method C

A solution of 1,1-dimethylethyl 4,5,7,8-tetrahydropyrazolo[3,4-d]azepine-6(2H)-carboxylate (may be prepared as described in Description 9) (900 mg, 3.8 mmol), 4-bromophenylboronic acid (1.5 g, 7.6 mmol; commercially available from e.g. Aldrich), copper acetate (2.06 g, 11.4 mmol), molecular sieves (4 Å, 3.5 g) and pyridine (614 µl, 7.6 mmol) in dichloromethane (50 ml) was stirred at room temperature open to atmosphere for 60 hours. The mixture was then filtered through a celite pad washing with methanol. The solvent was evaporated in vacuo. Residue taken up into ethyl acetate and washed with 5% aq. sodium hydrogen carbonate (×2) and brine, then dried over magnesium sulphate and evaporated in vacuo. The resulting residue was purified by chromatography on silica gel, eluting with a mixture of 2M ammonia in methanol/dichloromethane (0-5%), followed by further chromatography on silica gel, eluting with a mixture of ethyl acetate in hexane (10-20%) to afford the title compound (D12). MS (ES+) m/e 336 and 338 [M-$^t$Bu]⁺.

Description 13

1-(5-Bromo-2-pyridinyl)-2-pyrrolidinone (D13)

Method A

To a solution of 2-pyrrolidinone (797 µl, 10.4 mmol) in dimethylformamide (10 ml) at 0° C. was added sodium hydride (60% wt. in oil, 416 mg, 10.4 mmol) portionwise. The reaction mixture was allowed to stir at room temperature for 30 mins before adding a solution of 5-bromo-2-chloropyridine (1.00 g, 5.20 mmol) in dimethylformamide (2 ml). The resulting mixture was allowed to warm to room temperature for 18 hours, then heated at 50° C. for 1 hour and then at 80° C. for a further 1.5 hours. Methanol and water were added and the mixture extracted into dichloromethane, dried over magnesium sulphate and concentrated in vacuo. The product was purified by chromatography on silica, eluting with a mixture of ethyl acetate and pentane (0-50%) to afford the title compound. (D13) MS (ES+) m/e 241 & 243 [M+H]⁺.

Method B

To a solution of pyrrolidinone (0.797 ml, 10.4 mmol) in dimethylformamide (10 ml) at 0° C. was added sodium hydride (60% wt in oil, 416 mg, 10.4 mmol) portionwise. The resulting mixture was allowed to stir at 0° C. for 30 minutes. A solution of 5-bromo-2-chloropyridine (1.00 g, 5.20 mmol) in dimethylformamide (2 ml) was added and the resulting mixture allowed to warm to room temperature overnight. The mixture was then heated at 50° C. for 1 hour and 80° C. for 1.5 hours. After cooling to room temperature, the mixture was quenched with methanol and water, extracted with dichloromethane (3×100 ml) and dried over magnesium sulphate. The crude mixture was purified by column chromatography eluting with a mixture of ethyl acetate and pentane (0-50%) to afford the product (D13); MS (ES+) m/e 241 & 243 [M+H]$^+$.

Description 14

2-(4-Bromophenyl)-6-(phenylmethyl)-2,4,5,6,7,8-hexahydropyrazolo[3,4-d]azepine (D14)

Method A

A mixture of 6-(phenylmethyl)-2,4,5,6,7,8-hexahydropyrazolo[3,4-d]azepine (may be prepared as described in Description 5) (500 mg, 2.20 mmol), (4-bromophenyl)boronic acid (885 mg, 4.40 mmol; commercially available from e.g. Aldrich), copper acetate (1.19 g, 6.60 mmol), pyridine (0.36 ml, 4.40 mmol) and molecular sieves (1.5 g) in dichloromethane (20 ml) was allowed to stir at room temperature in a flask open to the atmosphere for 48 hours, then a further 4 days. The reaction mixture was filtered through a pad of celite, washing with dichloromethane and methanol. The filtrate was evaporated, redissolved in methanol and passed down a 10 g SCX cartridge, eluting with methanol, then a 2 M solution of ammonia in methanol. The crude mixture was purified by reverse phase chromatography eluting with a mixture of acetonitrile and water (5-100%) to afford the product (D14); MS (ES+) m/e 382 & 384 [M+H]$^+$.

Method B 6-(Phenylmethyl)-2,4,5,6,7,8-hexahydropyrazolo[3,4-d]azepine, (may be prepared as described in Description 5) (50 mg, 0.22 mmol), 4 bromo-phenyl boronic acid (88 mg, 0.44 mmol; commercially available from e.g. Aldrich), copper (II) acetate (120 mg, 0.66 mmol) and pyridine (35 µl, 0.44 mmol) and 4 Å molecular sieves (150 mg) were stirred at room temperature under air for 72 hours. The resulting crude was then loaded on to a 1 g pre equilibrated ion exchange cartridge (SCX), eluted with methanol and 2M ammonia in methanol. The basic fractions were evaporated and the resulting crude purified by reverse phase chromatography to afford the title compound as a formic salt. This product was loaded on to a 1 g pre equilibrated ion exchange cartridge (SCX) and eluted with methanol and 2M ammonia methanol. The basics fractions were combined and evaporated to afford the title product (D14); MS (ES+) m/e 382/384 [M+H]$^+$ Description 15

2-(6-Bromo-3-pyridinyl)-6-(phenylmethyl)-2,4,5,6,7,8-hexahydropyrazolo[3,4-d]azepine (D15)

A mixture of 6-(phenylmethyl)-2,4,5,6,7,8-hexahydropyrazolo[3,4-d]azepine (may be prepared as described in Description 5) (200 mg, 0.88 mmol), (6-bromo-3-pyridinyl) boronic acid (355 mg, 1.76 mmol), copper acetate (478 mg, 2.64 mmol), pyridine (0.142 ml, 1.76 mmol) and molecular sieves (600 mg) in dichloromethane (10 ml) was allowed to stir at room temperature in a flask open to the atmosphere for 240 hours. The reaction mixture was filtered through a pad of celite, washing with dichloromethane and methanol. The filtrate was evaporated, redissolved in methanol and passed down a 10 g SCX cartridge, eluting with methanol, then a 2 M solution of ammonia in methanol. The basic fractions were combined, evaporated and purified by column chromatography, eluting with a mixture of 2M ammonia in methanol and dichloromethane (0-10%). The impure product was re-purified using reverse phase chromatography, eluting with a mixture of acetonitrile and water (5-100% and 3-60%) to afford the product (D15); MS (ES+) m/e 383 & 385 [M+H]$^+$.

Description 16

1-{5-[6-(Phenylmethyl)-5,6,7,8-tetrahydropyrazolo[3,4-d]azepin-2(4H)-yl]-2-pyridinyl}-2-pyrrolidinone (D16)

Method A

A mixture of 6-(phenylmethyl)-2,4,5,6,7,8-hexahydropyrazolo[3,4-d]azepine (may be prepared as described in Description 5) (40.0 mg, 0.18 mmol), 1-(5-bromo-2-pyridinyl)-2-pyrrolidinone (may be prepared as described in Description 13) (48.0 mg, 0.20 mmol), copper(I) iodide (10.0 mg, 0.05 mmol), trans-1,2-diaminocyclohexane (6 µl, 0.05 mmol), and K$_3$PO$_4$ (137 mg, 0.65 mmol) was suspended in dioxan (3 ml) and heated, under argon, at 140° C. for 18 hours. The crude mixture was diluted with methanol, applied to a SCX cartridge (Varian bond-elute, 5 g) and washed with methanol followed by a mixture of 2M ammonia/methanol. The basic fractions were combined, evaporated and purified further by chromatography on silica, eluting with a mixture of 2M ammonia in methanol/dichloromethane (0-5%) to afford the title compound (D16). MS (ES+) m/e 388 [M+H]$^+$.

Method B

A mixture of 6-(phenylmethyl)-2,4,5,6,7,8-hexahydropyrazolo[3,4-d]azepine (may be prepared as described in Description 5) (40.0 mg, 0.18 mmol), 1-(5-bromo-2-pyridinyl)-2-pyrrolidinone (may be prepared as described in Description 13) (48.0 mg, 0.20 mmol), copper iodide (10.0 mg, 0.05 mmol), (1R,2R)-1,2-cyclohexanediamine (6.00 µl, 0.05 mmol) and potassium phosphate (137 mg, 0.65 mmol) in dioxan (3 ml) was heated at reflux overnight and then allowed to cool over the weekend. The mixture was diluted with methanol and passed down a 5 g SCX cartridge, eluting with methanol then a 2M solution of ammonia in methanol. The basic fractions were combined, evaporated and purified by column chromatography eluting with a mixture of 2M ammonia in methanol and dichloromethane (0-5%) to afford the product (D16); MS (ES+) m/e 388 [M+H]$^+$.

Method C

A mixture of 2-(6-bromo-3-pyridinyl)-6-(phenylmethyl)-2,4,5,6,7,8-hexahydropyrazolo[3,4-d]azepine (may be prepared as described in Description 15) (40 mg, 0.10 mmol), 2-pyrrolidinone (15 µl, 0.20 mmol), potassium carbonate (41 mg, 0.30 mmol), copper (I) iodide (6 mg, 0.03 mmol) and N,N'-dimethyl-1,2-ethanediamine (4 µl, 0.03 mmol) in dioxane (4 ml) was heated to reflux for 24 hours. The same amounts again of 2-pyrrolidinone, copper (I) iodide and N,N'-dimethyl-1,2-ethanediamine were added and the mixture heated to reflux for 2 hours. After the solvent was evaporated in vacuo, the residue was purified by SCX cartridge followed by chromatography on silica gel, eluting with a mixture of 2M ammonia in methanol/dichloromethane (0-10%). Column was repeated eluting with a mixture of 2M ammonia in methanol/dichloromethane (0-7.5%) to afford the title compound (D16). MS (ES+) m/e 388 [M+H]$^+$.

Description 17

1,1-Dimethylethyl 2-(6-bromo-3-pyridinyl)-4,5,7,8-tetrahydropyrazolo[3,4-d]azepine-6(2H)-carboxylate (D17)

A mixture of 1,1-dimethylethyl 4,5,7,8-tetrahydropyrazolo[3,4-d]azepine-6(2H)-carboxylate (may be prepared as described in Description 9) (207 mg, 0.87 mmol), (6-bromo-3-pyridinyl)boronic acid (204 mg, 1.74 mmol), copper acetate (472 mg, 2.61 mmol), pyridine (140 µl, 1.74 mmol) and molecular sieves (4 Å, 750 mg) in dichloromethane (10 ml) was stirred open to the atmosphere for 8 days. Crude mixture was then filtered through a pad of celite and washed with dichloromethane and ammonia. After evaporation in vacuo, the residue was purified by SCX cartridge eluting with methanol first then 2M ammonia in methanol. The methanol fractions containing the product were combined and evaporated in vacuo. The residue was then purified by column chromatography on silica gel eluting with a mixture of hexane in ethyl acetate (10:1 to 1:1) to afford the title compound (D17). MS (ES+) m/e 393 and 395 [M+H]$^+$.

Description 18

1,1-Dimethylethyl 2-[6-(2-oxo-1-pyrrolidinyl)-3-pyridinyl]-4,5,7,8-tetrahydropyrazolo[3,4-d]azepine-6(2M-carboxylate (D18)

A mixture of 1,1-dimethylethyl 2-(6-bromo-3-pyridinyl)-4,5,7,8-tetrahydropyrazolo[3,4-d]azepine-6(2H)-carboxylate (may be prepared as described in Description 17) (73 mg, 0.19 mmol), CuI (11 mg, 0.06 mmol), K$_2$CO$_3$ (92 mg, 0.67 mmol), dioxane (3.7 ml), N,N'-dimethyl-1,2-ethanediamine (0.006 ml, 0.06 mmol) and 2-pyrrolidinone (0.028 ml, 0.37 mmol) were mixed together and heated under Argon to reflux over 10 min and kept at this temperature for 12.5 h. After an additional 1.5 h more CuI (0.3 eq), K$_2$CO$_3$ (3.6 eq), N,N'-dimethyl-1,2-ethanediamine (0.3 eq) and 2-pyrrolidinone (2 eq) were added and the mixture heated at reflux for a further 2.75 h. The mixture was then allowed to cool and allowed to stand at room temperature for 77 h. The mixture was then reduced under vacuum and purified by chromatography on silica gel eluting with hexane:ethyl acetate 10:1→7:1→5:1→3:1→1:1 to give the title compound (D18). MS (ES+) m/e 398 [M+H]$^+$.

Description 19

1-[5-(5,6,7,8-Tetrahydropyrazolo[3,4-d]azepin-2(4H)-yl)-2-pyridinyl]-2-pyrrolidinone (D19)

Method A

1-{5-[6-(Phenylmethyl)-5,6,7,8-tetrahydropyrazolo[3,4-d]azepin-2(4H)-yl]-2-pyridinyl}-2-pyrrolidinone (may be prepared as described in Description 16) (38.0 mg, 0.10 mmol) was dissolved in ethanol (3 ml). Palladium (5.0 mg, 10% on charcoal paste) was added and the reaction mixture was stirred at room temperature under hydrogen (atmospheric pressure) for 12 hours. The mixture was filtered through celite and the filtrate concentrated in vacuo. The product was purified by chromatography on silica, eluting with a mixture of 2M ammonia in methanol/dichloromethane (0-5%) to afford the title compound (D19). MS (ES+) m/e 298 [M+H]$^+$.

Method B

To a solution of 1-{5-[6-(phenylmethyl)-5,6,7,8-tetrahydropyrazolo[3,4-d]azepin-2(4H)-yl]-2-pyridinyl}-2-pyrrolidinone (may be prepared as described in Description 16) (38.0 mg, 0.10 mmol) in ethanol (3 ml) was added palladium on carbon (10% 1:1 paste) (5.00 mg) and the resulting mixture stirred at room temperature overnight under an atmosphere of hydrogen. The mixture was then filtered, evaporated and purified by column chromatography eluting with a mixture of 2M ammonia in methanol and dichloromethane (0-5%) to afford the product (D19); MS (ES+) m/e 298 [M+H]$^+$.

Method C

A solution of 1-{5-[6-(phenylmethyl)-5,6,7,8-tetrahydropyrazolo[3,4-d]azepin-2(4H)-yl]-2-pyridinyl}-2-pyrrolidinone (may be prepared as described in Description 16) (145 mg, 0.37 mmol) and palladium on charcoal (15 mg) in ethanol (5 ml) was stirred at room temperature under an atmosphere of hydrogen for 18 hours. The mixture was then filtered through a celite pad washing with ethanol. The solvent was evaporated in vacuo, the resulting residue purified by SCX cartridge, followed by chromatography on silica gel, eluting with a mixture of 2M ammonia in methanol/dichloromethane (0-5%) to afford the title compound (D19). MS (ES+) m/e 298 [M+H]$^+$.

Method D

A solution of 1,1-dimethylethyl 2-[6-(2-oxo-1-pyrrolidinyl)-3-pyridinyl]-4,5,7,8-tetrahydropyrazolo[3,4-d]azepine-6(2H)-carboxylate (may be prepared as described in Description 18) (51 mg, 0.13 mmol) in dichloromethane (4 ml) was treated with trifluoroacetic acid (2 ml) and stirred at room temperature for 1 h 50 min. The mixture was then diluted with methanol (ca. 5 ml) and purified by SCX eluting with methanol and then methanol/ammonia (2M). The appropriate fractions were combined and then reduced to give the title compound (D19). MS (ES+) m/e 298 [M+H]$^+$.

Description 20

1-{4-[6-(Phenylmethyl)-5,6,7,8-tetrahydropyrazolo[3,4-d]azepin-2(4H)-yl]phenyl}-2-pyrrolidinone (D20)

Method A

A mixture of 6-(phenylmethyl)-2,4,5,6,7,8-hexahydropyrazolo[3,4-d]azepine (may be prepared as described in Description 5) (40.0 mg, 0.18 mmol), 1-(4-bromophenyl)-2-pyrrolidinone (48.0 mg, 0.20 mmol), copper(I) iodide (10.0 mg, 0.05 mmol), trans-1,2-diaminocyclohexane (6 µl, 0.05 mmol), and K$_3$PO$_4$ (137 mg, 0.65 mmol) was suspended in dioxan (3 ml) and heated, under argon, at 140° C. for 18 hours. The crude mixture was diluted with methanol, applied to a SCX cartridge (Varian bond-elute, 10 g) and washed with methanol followed by a mixture of 2M ammonia/methanol.

The basic fractions were combined, evaporated and purified further by chromatography on silica, eluting with a mixture of 2M ammonia in methanol/dichloromethane (0-3%) to afford the title compound (D20). MS (ES+) m/e 387 [M+H]$^+$.

Method B

1-{4-[6-(Phenylmethyl)-5,6,7,8-tetrahydropyrazolo[3,4-d]azepin-2(4H)-yl]phenyl}-2-pyrrolidinone (D20) may be prepared from 6-(phenylmethyl)-2,4,5,6,7,8-hexahydropyrazolo[3,4-d]azepine (40.0 mg, 0.18 mmol) (may be prepared as described in Description 5) using an analogous process to that described in Description 16 substituting 1-(5-bromo-2-pyridinyl)-2-pyrrolidinone for 1-(4-bromophenyl)-2-pyrrolidinone. MS (ES+) m/e 387 [M+H]$^+$.

Method C

A mixture of 2-(4-bromophenyl)-6-(phenylmethyl)-2,4,5,6,7,8-hexahydropyrazolo[3,4-d]azepine (may be prepared as described in Description 14) (140 mg, 0.37 mmol), pyrrolidinone (56.0%, 0.74 mmol), potassium carbonate (184 mg, 1.33 mmol), copper iodide (21.0 mg, 0.11 mmol) and N,N'-dimethyl-1,2-ethanediamine (12.0 µl, 0.11 mmol) in anhydrous dioxan (6 ml) was heated at reflux overnight. A further portion of pyrrolidinone (56.0 µl, 0.74 mmol), potassium carbonate (184 mg, 1.33 mmol), copper iodide (21.0 mg, 0.11 mmol) and N,N'-dimethyl-1,2-ethanediamine (12.0 µl, 0.11 mmol) were added and refluxing continued for 24 hours. After cooling to room temperature the mixture was passed down a 10 g SCX cartridge, eluting with methanol and then a 2M solution of ammonia in methanol. Purification was carried out by column chromatography eluting with a mixture of 2M ammonia in methanol and dichloromethane (0-4%) to afford the product (D20); MS (ES+) m/e 387 [M+H]$^+$.

Description 21

1,1-Dimethylethyl 2-[4-(2-oxo-1-pyrrolidinyl)phenyl]-4,5,7,8-tetrahydropyrazolo[3,4-d]azepine-6(2H)-carboxylate (D21)

Method A

A mixture of 1,1-dimethylethyl 2-(4-bromophenyl)-4,5,7,8-tetrahydropyrazolo[3,4-d]azepine-6(2H)-carboxylate (may be prepared as described in Description 12) (222 mg, 0.57 mmol), 2-pyrrolidinone (96 mg, 0.09 ml, 1.13 mmol), tris(dibenzylideneacetone)dipalladium(0) (26 mg, 0.029 mmol), (9,9-dimethyl-9H-xanthene-4,5-diyl)bis(diphenylphosphane) (49 mg, 0.086 mmol) and cesium carbonate (279 mg, 0.86 mmol) was suspended in dioxan (7 ml) and heated, under argon, at reflux for 18 hours. The reaction was cooled to room temperature, diluted with water and extracted with ethyl acetate (×3). The combined organic layers were washed with water (×2), dried over magnesium sulphate and solvent evaporated in vacuo. The crude product was triturated in hexane and filtered, and then purified further by chromatography on silica gel, eluting with a mixture of methanol in dichloromethane (0-3%) to afford the title compound (D21). MS (ES+) m/e 341 [M-$^t$Bu]$^+$.

Method B

A mixture of 1,1-dimethylethyl 2-(4-bromophenyl)-4,5,7,8-tetrahydropyrazolo[3,4-d]azepine-6(2H)-carboxylate (may be prepared as described in Description 12) (179 mg, 0.46 mmol), K$_2$CO$_3$ (227 mg, 1.64 mmol), CuI (26 mg, 0.14 mmol), N,N'-dimethyl-1,2-ethanediamine (0.015 ml, 0.14 mmol) and 2-pyrrolidinone (0.070 ml, 0.91 mmol) in dioxane (9 ml) was heated to reflux over ~15 min and was then left at this temperature overnight. More K$_2$CO$_3$ (3.6 eq), CuI (0.3 eq), N,N'-dimethyl-1,2-ethanediamine (0.3 eq) and 2-pyrrolidinone (2 eq) were added after an additional 1.5 hours (reaction cooled before reagents added) and the resulting mixture stirred at reflux under Argon for an additional 3.5 h and then for an additional 2.5 hours. More dioxane (5 ml) was added to replace that lost and the mixture left at reflux under Argon for an additional 1 hour. More K$_2$CO$_3$ (3.6 eq), CuI (0.3 eq), 2-pyrrolidinone (2 eq) and N,N'-dimethyl-1,2-ethanediamine (0.3 eq) were added and the mixture left to stir at reflux under Argon overnight. After 16.5 hours, more dioxane (4 ml) was added and the mixture allowed to cool to room temperature. The solvent was then removed, the residue treated with dichloromethane (~25 ml) and the mixture filtered through celite washing with more dichloromethane. The filtrate was then reduced and the residue purified by chromatography on silica gel eluting with dichloromethane→dichloromethane:methanol 50:1→25:1. The partially purified residue was then triturated with hexane: ethyl acetate 10:1 to give the title compound (D21). MS (ES+) m/e 397 [M+H]$^+$.

Description 22

1-[4-(5,6,7,8-Tetrahydropyrazolo[3,4-d]azepin-2(4H)-yl)phenyl]-2-pyrrolidinone (D22)

Method A

1-{4-[6-(Phenylmethyl)-5,6,7,8-tetrahydropyrazolo[3,4-d]azepin-2(4H)-yl]phenyl}-2-pyrrolidinone (may be prepared as described in Description 20) (23.0 mg, 0.06 mmol) was dissolved in ethanol (3 ml). Palladium (5.0 mg, 10% on charcoal paste) was added and the reaction mixture was stirred at room temperature under hydrogen (atmospheric pressure) for 12 hours. The mixture was filtered through celite and the filtrate concentrated in vacuo. The product was purified by chromatography on silica, eluting with a mixture of 2M ammonia in methanol/dichloromethane (0-10%) to afford the title compound (D22). MS (ES+) m/e 297 [M+H]$^+$.

Method B

1-[4-(5,6,7,8-Tetrahydropyrazolo[3,4-d]azepin-2(4H)-yl)phenyl]-2-pyrrolidinone (D22) may be prepared from 1-{4-[6-(phenylmethyl)-5,6,7,8-tetrahydropyrazolo[3,4-d]azepin-2(4H)-yl]phenyl}-2-pyrrolidinone (may be prepared as described in Description 20) (23.0 mg, 0.06 mmol) using an analogous process to that described in Description 19; MS (ES+) m/e 297 [M+H]$^+$.

Method C

A solution/suspension of 1-{4-[6-(phenylmethyl)-5,6,7,8-tetrahydropyrazolo[3,4-d]azepin-2(4H)-yl]phenyl}-2-pyrrolidinone (may be prepared as described in Description 20) (180 mg, 0.47 mmol) in ethanol (20 ml) was stirred at room temperature under an atmosphere of hydrogen for 72 hours. The mixture was then filtered through celite and evaporated to afford the crude product which was purified by column chromatography eluting with a mixture of 2M ammonia in methanol and dichloromethane (0-10%) to afford the product (D22); MS (ES+) m/e 297 [M+H]$^+$.

Method D

To a solution of 1,1-dimethylethyl 2-[4-(2-oxo-1-pyrrolidinyl)phenyl]-4,5,7,8-tetrahydropyrazolo[3,4-d]azepine-6(2H)-carboxylate (may be prepared as described in Description 21) (189 mg, 0.48 mmol) in dichloromethane (12 ml) was added trifluoroacetic acid (6 ml). The resulting mixture was stirred at room temperature for 1 hr and then diluted with methanol. Reaction was purified by SCX, eluting with methanol and then 2M ammonia/methanol. The basic fractions were combined and solvent evaporated in vacuo to afford the title compound (D22). MS (ES+) m/e 297 [M+H]$^+$.

Method E

A solution of 1,1-dimethylethyl 2-[4-(2-oxo-1-pyrrolidinyl)phenyl]-4,5,7,8-tetrahydropyrazolo[3,4-d]azepine-6(2H)-carboxylate (may be prepared as described in Description 21) (132 mg, 0.33 mmol) in DCM (5 ml) was treated with TFA (2.5 ml) and the mixture stirred at room temperature for 1.5 hours. The mixture was then diluted with methanol (~5 ml) and passed through an SCX cartridge eluting with methanol and then MeOH/NH$_3$ (2M) to give the title compound (D22). MS (ES+) m/e 297 [M+H]$^+$.

Description 23

4-[6{[(1,1-Dimethylethyl)oxy]carbonyl}-5,6,7,8-tetrahydropyrazolo[3,4-d]azepin-2(4H)-yl]benzoic acid (D23)

To 1,1-dimethylethyl 2-(4-cyanophenyl)-4,5,7,8-tetrahydropyrazolo[3,4-d]azepine-6(2H)-carboxylate (may be prepared as described in Description 10) (750 mg, 2.22 mmol) in ethanol (7.5 ml) was added 10% sodium hydroxide solution (7.5 ml), and the reaction heated at reflux, under argon, for 5 hours. 10% sodium hydroxide solution (10 ml) was added and stirring continued at reflux, under argon, overnight. The reaction was cooled to room temperature and the solvent partially reduced in vacuo. The resulting crude product was dissolved in water and acidified with 5N hydrochloric acid. Ethyl acetate was added, and the product extracted into ethyl acetate (×3). The combined organic fractions were dried over magnesium sulphate and solvent evaporated in vacuo to afford the title compound (D23). MS (ES−) m/e 356 [M−H]$^−$.

Description 24

1,1-Dimethylethyl 2-{4-[(methylamino)carbonyl]phenyl}-4,5,7,8-tetrahydropyrazolo[3,4-d]azepine-6(2H)-carboxylate (D24)

To a suspension of 4-[6-{[(1,1-dimethylethyl)oxy]carbonyl}-5,6,7,8-tetrahydropyrazolo[3,4-d]azepin-2(4H)-yl]benzoic acid (may be prepared as described in Description 23) (185 mg, 0.52 mmol) in dichloromethane (10 ml) was added 1,1'-(oxomethanediyl)bis-1H-imidazole (168 mg, 1.04 mmol) and the reaction stirred at room temperature, under argon, overnight. Methylamine (64 mg, 2.07 mmol) was added and stirring continued, under argon, at room temperature for 4 hours. The resulting crude mixture was diluted with water, and extracted with dichloromethane (×2). The combined organic fractions were washed with water (×1), dried over magnesium sulphate and solvent evaporated in vacuo to afford the title compound (D24). MS (ES+) m/e 371 [M+H]$^+$.

Description 25

N-Methyl-4-(5,6,7,8-tetrahydropyrazolo[3,4-d]azepin-2(4H)-yl)benzamide (D25)

A solution of 1,1-dimethylethyl 2-{4-[(methylamino)carbonyl]phenyl}-4,5,7,8-tetrahydropyrazolo[3,4-d]azepine-6(2H)-carboxylate (184 mg, 0.50 mmol; may be prepared as described in Description 24) in dichloromethane (2 ml) was treated with trifluoroacetic acid (2 ml). The mixture was stirred at room temperature for 2 hours. The mixture was diluted with methanol and passed down a SCX cartridge eluting with methanol and then a 2M solution of ammonia in methanol. The basic fractions were combined and evaporated to afford the title compound (D25); MS (ES+) m/e 271 [M+H]+.

Description 26

1,1-Dimethylethyl 2-[4-(2-oxo-1,3-oxazolidin-3-yl)phenyl]-4,5,7,8-tetrahydropyrazolo[3,4-d]azepine-6(2H)-carboxylate (D26)

A mixture of 1,1-dimethylethyl 2-(4-bromophenyl)-4,5,7,8-tetrahydropyrazolo[3,4-d]azepine-6(2H)-carboxylate (150 mg, 0.38 mmol) (may be prepared as described in Description 12), 1,3-oxazolidin-2-one (100 mg, 1.15 mmol), tris(dibenzylideneacetone)dipalladium(0) (18.0 mg, 0.02 mmol), 9,9-dimethyl-4,5-bis(diphenylphosphino)xanthene (35.0 mg, 0.06 mmol) and cesium carbonate (195 mg, 0.60 mmol) in dioxan (4 ml) was heated at reflux under argon for 3 hours and then in the microwave for 2 hours at 150° C. The mixture was diluted with ethyl acetate, filtered through celite and washed with 2×20 ml of water. The combined ethyl acetate layers were dried over magnesium sulphate, filtered and evaporated. The crude product was purified by column chromatography eluting with a mixture of ethyl acetate/pentane (50-100%) to afford the product (D26); MS (ES+) m/e 399 [M+H]$^+$.

Method B

A mixture of 1,1-dimethylethyl 2-(4-bromophenyl)-4,5,7,8-tetrahydropyrazolo[3,4-d]azepine-6(2H)-carboxylate (may be prepared as described in Description 12) (160 mg, 0.41 mmol), 2-oxazolidinone (71 mg, 0.82 mmol), potassium carbonate (170 mg, 1.23 mmol), copper (I) iodide (24 mg, 0.12 mmol) and N,N'-dimethyl-1,2-ethanediamine (13 µl, 0.12 mmol) in dioxane (10 ml) was heated at reflux overnight. The same amounts again of 2-oxazolidinone, copper (I) iodide and N,N'-dimethyl-1,2-ethanediamine were added and the mixture heated for 6 hours. The reaction mixture was transferred to a microwave vial, the same amounts again of 2-oxazolidinone, copper (I) iodide and N,N'-dimethyl-1,2-ethanediamine were added and the mixture heated at 100° C. in microwave for 1 hour. The same amounts again of 2-oxazolidinone, copper (I) iodide and N,N'-dimethyl-1,2-ethanediamine were added and the mixture heated at 100° C. in microwave for a further 2 hours. Crude mixture was filtered through a celite pad washing with methanol. The solvent was evaporated in vacuo, the residue was taken up into ethyl acetate, washed with water and brine, then dried over magnesium sulphate. After evaporation of the solvent in vacuo, the residue was purified by column chromatography on silica gel, eluting with a 50% mixture of ethyl acetate in hexane to afford the title compound (D26). MS (ES+) m/e 343 [M-'Bu]+.

Description 27

3-[4-(5,6,7,8-Tetrahydropyrazolo[3,4-d]azepin-2(4H)-yl)phenyl]-1,3-oxazolidin-2-one (D27)

Method A

A solution of 1,1-dimethylethyl 2-[4-(2-oxo-1,3-oxazolidin-3-yl)phenyl]-4,5,7,8-tetrahydropyrazolo[3,4-d]azepine-6(2H)-carboxylate (40.0 mg, 0.10 mmol) (may be prepared as described in Description 26) in dichloromethane (1 ml) was treated with trifluoroacetic acid (1 ml) and stirred at room temperature for 1 hour. The mixture was diluted with methanol and passed down a SCX cartridge, eluting with methanol and then a 2M ammonia in methanol solution. The basic fractions were combined and evaporated to afford the title compound (D27); MS (ES+) m/e 299 [M+H]+.

Method B

To a solution of 1,1-dimethylethyl 2-[4-(2-oxo-1,3-oxazolidin-3-yl)phenyl]-4,5,7,8-tetrahydropyrazolo[3,4-d]azepine-6(2H)-carboxylate (may be prepared as described in Description 26) (104 mg, 0.26 mmol) in dioxan (1 ml) was added 4M hydrochloric acid in dioxan (2 ml). The resulting mixture was stirred at room temperature, under argon, for 20 hours. The reaction mixture was diluted with methanol and then purified by SCX, eluting with methanol and then 2M ammonia/methanol. The basic fractions were combined and solvent evaporated in vacuo to afford the title compound (D27). MS (ES+) m/e 299 [M+H]+.

Description 28

1,1-Dimethylethyl 2-[4-(3-methyl-2-oxo-1-imidazolidinyl)phenyl]-4,5,7,8-tetrahydropyrazolo[3,4-d]azepine-6(2H)-carboxylate (D28)

Method A

A mixture of 1,1-dimethylethyl 2-(4-bromophenyl)-4,5,7,8-tetrahydropyrazolo[3,4-d]azepine-6(2H)-carboxylate (150 mg, 0.38 mmol) (may be prepared as described in Description 12), 1-methyl-2-imidazolidinone (115 mg, 1.15 mmol), tris(dibenzylideneacetone)dipalladium(0) (18.0 mg, 0.02 mmol), 9,9-dimethyl-4,5-bis(diphenylphosphino)xanthene (35.0 mg, 0.06 mmol) and cesium carbonate (195 mg, 0.60 mmol) in dioxan (4 ml) was heated at reflux under argon for 3 hours. The mixture was allowed to cool to room temperature, diluted with ethyl acetate, filtered through celite and washed with 2×20 ml of water. The combined ethyl acetate layers were dried over magnesium sulphate, filtered and evaporated. The crude product was purified by column chromatography eluting with a mixture of ethyl acetate/pentane (50-100%) to afford the product (D28); MS (ES+) m/e 412 [M+H]+.

Method B

A mixture of 1,1-dimethylethyl 2-(4-bromophenyl)-4,5,7,8-tetrahydropyrazolo[3,4-d]azepine-6(2H)-carboxylate (may be prepared as described in Description 12) (80 mg, 0.20 mmol), 1-methyl-2-imidazolidinone (20 mg, 0.40 mmol), tris(dibenzylideneacetone)dipalladium(0) (9 mg, 0.01 mmol), (9,9-dimethyl-9H-xanthene-4,5-diyl)bis(diphenylphosphane) (17 mg, 0.03 mmol) and cesium carbonate (98 mg, 0.3 mmol) was suspended in dioxan (4 ml) and heated, under argon, at reflux for 18 hours. A further 2 eq. of 1-methyl-2-imidazolidinone, 0.05 eq. of tris(dibenzylideneacetone)dipalladium(0), 0.15 eq. of (9,9-dimethyl-9H-xanthene-4,5-diyl)bis(diphenylphosphane) and 1.5 eq. of cesium carbonate were added in dioxan (2 ml) and the reaction left at reflux, under argon, for a further 4 hours. The reaction was cooled to room temperature, diluted with water and extracted with ethyl acetate (×3). The combined organic layers were washed with water (×2), brine (×1), dried over magnesium sulphate and solvent evaporated in vacuo. The crude product was purified by column chromatography on silica gel, eluting with a mixture of ethyl acetate in hexane (0-30%) to afford the title compound (D28). MS (ES+) m/e 412 [M-'Bu]+.

Description 29

1-Methyl-3-[4-(5,6,7,8-tetrahydropyrazolo[3,4-d]azepin-2(4H)-yl)phenyl]-2-imidazolidinone (D29)

Method A

A solution of 1,1-dimethylethyl 2-[4-(3-methyl-2-oxo-1-imidazolidinyl)phenyl]-4,5,7,8-tetrahydropyrazolo[3,4-d]azepine-6(2H)-carboxylate (122 mg, 0.30 mmol) (may be prepared as described in Description 28) in dichloromethane (1 ml) was treated with trifluoroacetic acid (1 ml) and stirred at room temperature for 1 hour. The mixture was diluted with methanol and passed down a SCX cartridge, eluting with methanol and then a 2M ammonia in methanol solution. The basic fractions were combined and evaporated to afford the title compound (D29); MS (ES+) m/e 312 [M+H]+.

Method B

To a solution of 1,1-dimethylethyl 2-[4-(3-methyl-2-oxo-1-imidazolidinyl)phenyl]-4,5,7,8-tetrahydropyrazolo[3,4-d]azepine-6(2H)-carboxylate (may be prepared as described in Description 28) (47 mg, 0.11 mmol) in dioxan (1 ml) was added 4M hydrochloric acid in dioxan (2 ml). The resulting mixture was stirred at room temperature, under argon, for 5 hours. The reaction mixture was diluted with methanol and then purified by SCX, eluting with methanol and then 2M ammonia/methanol. The basic fractions were combined and solvent evaporated in vacuo to afford the title compound (D29). MS (ES+) m/e 312 [M+H]+.

Description 30

(1Z)-N-hydroxyethanimidamide (D30)

A mixture of acetonitrile (1.7 ml, 32.9 mmol) and a 50% aqueous solution of hydroxylamine (2.5 ml, 37.9 mmol) in ethanol (5 ml) was heated at reflux for 4.5 hours. The solvent was evaporated to give a white crystalline solid which was triturated with diethyl ether, filtered and dried in the vacuum oven to afford the product (D30); $^1$H NMR (d$^6$-DMSO) δ 1.62 (3H, s), 5.34 (2H, br s), 8.65 (1H, s).

Description 31

6-Cyclobutyl-2,4,5,6,7,8-hexahydropyrazolo[3,4-d]azepine (D31)

Method A

To a suspension of 2,4,5,6,7,8-hexahydropyrazolo[3,4-d]azepine (may be prepared as described in Description 7) (100 mg, 0.73 mmol) in dichloromethane (5 ml) was added cyclobutanone (55 µl, 0.73 mmol) followed by acetic acid (1 drop) and sodium triacetoxyborohydride (186 mg, 0.88 mmol). The mixture was stirred at room temperature for 2 hours, then it was diluted with methanol and purified by SCX cartridge to afford the title compound (D31). MS (ES+) m/e 192 [M+H]$^+$.

Method B 2,4,5,6,7,8-Hexahydropyrazolo[3,4-d]azepine (may be prepared as described in Description 7) (0.13, 0.95 mmol) in dichloromethane (3 ml) was treated with cyclobutanone (0.08 g, 1.13 mmol) and a catalytic amount of acetic acid. After 10 minutes the reaction was then treated with sodium triacetoxyborohydride (0.42 g, 1.9 mmol) and stirred for 2 hours. The reaction mixture was then diluted with methanol and applied to a SCX ion exchange cartridge and washed with methanol and then 2M solution of ammonia in methanol. The ammonia containing fractions were then combined and reduced and the resulting crude product (D31) may be used without further purification; (MS (ES+): [M+H]$^+$ at m/z 192.16

Description 32

1,1-Dimethylethyl 2-[4-(methylsulfonyl)phenyl]-4,5,7,8-tetrahydropyrazolo[3,4-d]azepine-6(2H)-carboxylate (D32)

A solution of 1,1-dimethylethyl 4,5,7,8-tetrahydropyrazolo[3,4-d]azepine-6(2H)-carboxylate (may be prepared as described in Description 9) (75 mg, 0.32 mmol), [4-(methylsulfonyl)phenyl]boronic acid (128 mg, 0.64 mmol), copper acetate (116 mg, 0.64 mmol), molecular sieves (4 Å, 0.2 g) and pyridine (52 µl, 0.64 mmol) in dichloromethane (2.5 ml) was stirred at room temperature open to atmosphere for 60 hours. The mixture was then diluted with methanol and filtered through a celite pad washing with methanol. The solvent was evaporated in vacuo. Residue was taken up into ethyl acetate and washed with water and 5% aq. sodium hydrogen carbonate, then dried over magnesium sulphate and evaporated in vacuo. The resulting residue was purified by MDAP to afford the title compound (D32). MS (ES+) m/e 392 [M+H]$^+$.

Description 33

1,1-Dimethylethyl 2-[4-(1-piperidinyl)phenyl]-4,5,7,8-tetrahydropyrazolo[3,4-d]azepine-6(2H)-carboxylate (D33)

A solution of 1,1-dimethylethyl 2-(4-bromophenyl)-4,5,7,8-tetrahydropyrazolo[3,4-d]azepine-6(2H)-carboxylate (may be prepared as described in Description 12) (150 mg, 0.38 mmol), piperidine (76 µl, 0.76 mmol), [2'-(dicyclohexylphosphanyl)-2-biphenylyl]dimethylamine (24 mg, 0.06 mmol), tris(dibenzylideneacetone)dipalladium(0) (174 mg, 0.20 mmol), and sodium tert-butoxide (73 mg, 0.76 mmol) in dioxan (4.5 ml) was heated at 120° C. in the microwave (normal absorption) for 30 min. The reaction mixture was diluted with methanol and then purified by SCX, eluting with methanol and then 2M ammonia/methanol. The basic fractions were combined and solvent evaporated in vacuo. The crude product was purified by column chromatography on silica gel, eluting with a mixture of ethyl acetate in hexane (0-50%) to afford the title compound. MS (ES+) m/e 397 [M+H]$^+$.

Description 34

1,1-Dimethylethyl 2-[4-(3-methyl-1,2,4-oxadiazol-5-yl)phenyl]-4,5,7,8-tetrahydropyrazolo[3,4-d]azepine-6(2H)-carboxylate (D34)

To a suspension of 4-[6-{[(1,1-dimethylethyl)oxy]carbonyl}-5,6,7,8-tetrahydropyrazolo[3,4-d]azepin-2(4H)-yl]benzoic acid (may be prepared as described in Description 23) (185 mg, 0.52 mmol) in dichloromethane (10 ml) was added 1,1'-(oxomethanediyl)bis-1H-imidazole (168 mg, 1.04 mmol) and the reaction stirred at room temperature, under argon, overnight. The solvent was evaporated in vacuo. Toluene (5 ml) and then (1Z)-N-hydroxyethanimidamide (may be prepared as described in Description 30) (116 mg, 1.56 mmol) were added and the reaction mixture heated, under argon, at reflux overnight. A further 2 eq. of 1,1'-(oxomethanediyl)bis-1H-imidazole was added and stirring continued for a further 40 minutes. A further 3 eq. of (1Z)-N-hydroxyethanimidamide was added and stirring continued for a further 3 hours. The reaction was cooled to room temperature and the solvent evaporated in vacuo. The resulting crude mixture was diluted with dichloromethane and water, and extracted into dichloromethane (×2). The combined organic fractions were washed with water (×1), dried over magnesium sulphate and solvent evaporated in vacuo to afford the title compound (D34). MS (ES+) m/e 340 [M-$^t$Bu]$^+$.

Description 35

2-[4-(3-Methyl-1,2,4-oxadiazol-5-yl)phenyl]-2,4,5,6,7,8-hexahydropyrazolo[3,4-d]azepine (D35)

To a solution of 1,1-dimethylethyl 2-[4-(3-methyl-1,2,4-oxadiazol-5-yl)phenyl]-4,5,7,8-tetrahydropyrazolo[3,4-d]azepine-6(2H)-carboxylate (may be prepared as described in Description 34) (159 mg, 0.40 mmol) in dichloromethane (12 ml) was added trifluoroacetic acid (6 ml). The resulting mixture was stirred at room temperature for 30 minutes and then diluted with methanol. Reaction was purified by SCX, eluting with methanol and then 2M ammonia/methanol. The basic fractions were combined and the solvent evaporated in vacuo to afford the title compound (D35). MS (ES+) m/e 296 [M+H]$^+$.

Description 36

1,1-Dimethylethyl 2-[4-(aminocarbonyl)phenyl]-4,5,7,8-tetrahydropyrazolo[3,4-d]azepine-6(2H)-carboxylate (D36)

To a suspension of 4-[6-{[(1,1-dimethylethyl)oxy]carbonyl}-5,6,7,8-tetrahydropyrazolo[3,4-d]azepin-2(4H)-yl]benzoic acid (may be prepared as described in Description 23) (185 mg, 0.52 mmol) in dichloromethane (10 ml) was added 1,1'-(oxomethanediyl)bis-1H-imidazole (168 mg, 1.04 mmol) and the reaction stirred at room temperature, under argon, overnight. Ammonia (0.88M, 35 mg, 2.07 mmol) was added and stirring continued, under argon, at room temperature for 4 hours. The resulting crude mixture was diluted with water, and extracted with dichloromethane (×2). The combined organic fractions were washed with water (×1), dried over magnesium sulphate and solvent evaporated in vacuo to afford the title compound (D36). MS (ES+) m/e 301 [M-$^t$Bu]$^+$.

Description 37

4-(5,6,7,8-Tetrahydropyrazolo[3,4-d]azepin-2(4H)-yl)benzamide (D37)

To a solution of 1,1-dimethylethyl 2-[4-(aminocarbonyl)phenyl]-4,5,7,8-tetrahydropyrazolo[3,4-d]azepine-6(2H)-carboxylate (may be prepared as described in Description 36) (167 mg, 0.47 mmol) in dichloromethane (14 ml) was added trifluoroacetic acid (7 ml). The resulting mixture was stirred at room temperature, under argon, for 2 hours and then diluted with methanol. Reaction was purified by SCX, eluting with methanol and then 2M ammonia/methanol. The basic fractions were combined and solvent evaporated in vacuo to afford the title compound (D37). MS (ES+) m/e 257 [M+H]$^+$.

Description 38

2-[4-(Methylsulfonyl)phenyl]-2,4,5,6,7,8-hexahydro-pyrazolo[3,4-d]azepine (D38)

To a solution of 1,1-dimethylethyl 2-[4-(methylsulfonyl)phenyl]-4,5,7,8-tetrahydropyrazolo[3,4-d]azepine-6(2H)-carboxylate (may be prepared as described in Description 32) (10 mg, 0.03 mmol) in dioxan (1 ml) was added 4M hydrochloric acid in dioxan (2 ml). The resulting mixture was stirred at room temperature, under argon, overnight. The reaction mixture was diluted with methanol and then purified by SCX, eluting with methanol and then 2M ammonia/methanol. The basic fractions were combined and solvent evaporated in vacuo to afford the title compound (D38). MS (ES+) m/e 292 [M+H]$^+$.

Description 39

1,1-Dimethylethyl 2-{4-[(methylsulfonyl)amino]phenyl}-4,5,7,8-tetrahydropyrazolo[3,4-d]azepine-6(2H)-carboxylate (D39)

To {4-[(methylsulfonyl)amino]phenyl}boronic acid (commercially available from e.g. Combi-Blocks) (127 mg, 0.29 mmol) in dichloromethane (3 ml) was added copper(II) acetate (107 mg, 0.59 mmol) and 4 Å molecular sieves (190 mg), and the reaction stirred at room temperature, open to air, for 10 minutes. 1,1-Dimethylethyl 4,5,7,8-tetrahydropyrazolo[3,4-d]azepine-6(2H)-carboxylate (may be prepared as described in Description 9) (70 mg, 0.29 mmol) was added and the reaction stirred at room temperature, open to air, overnight. The reaction mixture was diluted with methanol and filtered through a celite pad, washing with methanol. Solvent was evaporated in vacuo. Ethyl acetate and water were added, and the product was extracted into ethyl acetate (×3), washed with water (×1), then saturated sodium bicarbonate solution (×1), and then dried over magnesium sulfate. Solvent was evaporated in vacuo. The resulting crude product was purified by column chromatography on silica gel, eluting with a mixture of ethyl acetate in hexane (0-50%). Relevant fractions were combined and solvent evaporated in vacuo. The resulting crude product was purified further by Mass Directed Autopreparation to afford the title compound (D39). MS (ES+) m/e 407 [M+H]$^+$.

Description 40

N-[4-(5,6,7,8-Tetrahydropyrazolo[3,4-d]azepin-2(4H)-yl)phenyl]methanesulfonamide (D40)

To a solution of 1,1-dimethylethyl 2-{4-[(methylsulfonyl)amino]phenyl}-4,5,7,8-tetrahydropyrazolo[3,4-d]azepine-6(2H)-carboxylate (may be prepared as described in Description 39) (16 mg, 0.039 mmol) in dioxan (1 ml) was added 4M hydrochloric acid in dioxan (2 ml). The resulting mixture was stirred at room temperature, under argon, overnight. The reaction mixture was diluted with methanol and then purified by SCX, eluting with methanol and then 2M ammonia/methanol. The basic fractions were combined and solvent evaporated in vacuo to afford the title compound (D40). MS (ES+) m/e 307 [M+H]$^+$.

Description 41

1,1-Dimethylethyl 2-{4-[(dimethylamino)carbonyl]phenyl}-4,5,7,8-tetrahydropyrazolo[3,4-d]azepine-6(2H)-carboxylate (D41)

To a suspension of 4-[6-{[(1,1-dimethylethyl)oxy]carbonyl}-5,6,7,8-tetrahydropyrazolo[3,4-d]azepin-2(4H)-yl]benzoic acid (may be prepared as described in Description 23) (185 mg, 0.52 mmol) in dichloromethane (10 ml) was added 1,1'-(oxomethanediyl)bis-1H-imidazole (168 mg, 1.04 mmol) and the reaction stirred at room temperature, under argon, overnight. Dimethylamine (93 mg, 2.07 mmol) was added and stirring continued, under argon, at room temperature for 4 hours. The resulting crude mixture was diluted with water, and extracted with dichloromethane (×2). The combined organic fractions were washed with water (×1), dried over magnesium sulphate and solvent evaporated in vacuo to afford the title compound (D41). MS (ES+) m/e 385 [M+H]$^+$.

Description 42

N,N-Dimethyl-4-(5,6,7,8-tetrahydropyrazolo[3,4-d]azepin-2(4H)-yl)benzamide (D42)

To a solution of 1,1-dimethylethyl 2-{4-[(dimethylamino)carbonyl]phenyl}-4,5,7,8-tetrahydropyrazolo[3,4-d]azepine-6(2H)-carboxylate (may be prepared as described in Description 41) (194 mg, 0.50 mmol) in dichloromethane (14 ml) was added trifluoroacetic acid (7 ml). The resulting mixture was stirred at room temperature, under argon, for 2 hours and then diluted with methanol. Reaction was purified by SCX, eluting with methanol and then 2M ammonia/methanol. The basic fractions were combined and solvent evaporated in vacuo. Resulting crude product was purified further by column chromatography on silica gel, eluting with a mixture of 2M ammonia in methanol/dichloromethane (0-3%) to afford the title compound (D42). MS (ES+) m/e 285 [M+H]$^+$.

Description 43

2-[4-(1-Piperidinyl)phenyl]-2,4,5,6,7,8-hexahydropyrazolo[3,4-d]azepine (D43)

To a solution of 1,1-dimethylethyl 2-[4-(1-piperidinyl)phenyl]-4,5,7,8-tetrahydropyrazolo[3,4-d]azepine-6(2H)-carboxylate (may be prepared as described in Description 33) (70 mg, 0.18 mmol) in dioxan (1 ml) was added 4M hydrochloric acid in dioxan (2 ml). The resulting mixture was stirred at room temperature, under argon, overnight. The reaction mixture was diluted with methanol and then purified by SCX, eluting with methanol and then 2M ammonia/methanol. The basic fractions were combined and solvent evaporated in vacuo to afford the title compound (D43). MS (ES+) m/e 297 [M+H]$^+$.

Description 44

1,1-Dimethylethyl 2-[4-(1-pyrrolidinyl)phenyl]-4,5,7,8-tetrahydropyrazolo[3,4-d]azepine-6(2M-carboxylate (D44)

A mixture of 1,1-dimethylethyl 2-(4-bromophenyl)-4,5,7,8-tetrahydropyrazolo[3,4-d]azepine-6(2H)-carboxylate (may be prepared as described in Description 12) (200 mg, 0.51 mmol), pyrrolidine (73 mg, 1.02 mmol), tris(dibenzylideneacetone)dipalladium(0) (234 mg, 0.26 mmol), [2'-(dicyclohexylphosphanyl)-2-biphenylyl]dimethylamine (30 mg, 0.08 mmol) and sodium tert-butoxide (98 mg, 1.02 mmol) in dioxan (4 ml) was heated at 120° C. in the microwave (normal absorption) for 30 minutes. The reaction mixture was diluted with methanol and then purified by SCX, eluting with methanol and then 2M ammonia/methanol. The basic fractions were combined and solvent evaporated in vacuo. The crude product was purified by column chromatography on silica gel, eluting with a mixture of ethyl acetate in hexane (0-40%) to afford the title compound (D44). MS (ES+) m/e 383 [M+H]$^+$.

Description 45

2-[4-(1-Pyrrolidinyl)phenyl]-2,4,5,6,7,8-hexahydropyrazolo[3,4-d]azepine (D45)

To a solution of 1,1-dimethylethyl 2-[4-(1-pyrrolidinyl)phenyl]-4,5,7,8-tetrahydropyrazolo[3,4-d]azepine-6(2H)-carboxylate (may be prepared as described in Description 44) (79 mg, 0.21 mmol) in dioxan (3 ml) was added 4M hydrochloric acid in dioxan (2 ml). The resulting mixture was stirred at room temperature, under argon, overnight. The reaction mixture was diluted with methanol and then purified by SCX, eluting with methanol and then 2M ammonia/methanol. The basic fractions were combined and solvent evaporated in vacuo to afford the title compound (D45). MS (ES+) m/e 283 [M+H]$^+$.

Description 46

2-Phenyl-2,4,5,6,7,8-hexahydropyrazolo[3,4-d]azepine (D46)

A solution of 2-(4-bromophenyl)-6-(phenylmethyl)-2,4,5,6,7,8-hexahydropyrazolo[3,4-d]azepine (may be prepared as described in Description 14) (49 mg, 0.13 mmol) in ethanol (5 ml) with palladium (10% Pd/C Paste) as a catalyst (10 mg) was stirred under an atmosphere of hydrogen overnight. The next day, the resulting mixture was filtered through celite and to afford the title compound which may be used without further purification (D46). MS (ES+) m/e 214 [M+H]$^+$

Description 47

1,1-Dimethylethyl 3-oxo-2-[1-(phenylmethyl)-4-piperidinyl]-3,3a,4,5,7,8-hexahydropyrazolo[3,4-d]azepine-6(2H)-carboxylate (D47)

A mixture of 4-hydrazino-1-(phenylmethyl)piperidine dihydrochloride (commercially available from e.g. Aurora Screening Library) (2.68 g, 9.63 mmol) and tert-butanol (60 ml) was added to 1-(1,1-dimethylethyl) 4-ethyl 5-oxohexahydro-1H-azepine-1,4-dicarboxylate (may be prepared as described in Synthetic Communications (1992), 22(9), 1249-58) (2.50 g, 8.76 mmol) followed by triethylamine (7.33 ml, 52.59 mmol) and the resulting suspension warmed to reflux over ~10 min under Argon. The resulting clear yellow solution was then kept at this temperature for 65 h. The mixture was then allowed to cool to room temperature over ~2 h and the mixture reduced under vacuum to give a cream coloured solid residue. Purification by chromatography on silica gel eluting with dichloromethane:methanol 50:1→25:1→10:1 afforded a product which as partitioned between water and dichloromethane (100 ml each) the layers separated and the organic layer washed with more water (100 ml), followed by brine (100 ml) and then dried (Na$_2$SO$_4$), filtered and reduced to give the title compound (D47). MS (ES+) m/e 427 [M+H]$^+$.

Description 48

1,1-Dimethylethyl 2-[1-(phenylmethyl)-4-piperidinyl]-3-{[(trifluoromethyl)sulfonyl]oxy}-3,3a,4,5,7,8-hexahydropyrazolo[3,4-d]azepine-6(2H-carboxylate (D48)

A solution of 1,1-dimethylethyl 3-oxo-2-[1-(phenylmethyl)-4-piperidinyl]-3,3a,4,5,7,8-hexahydropyrazolo[3,4-d]azepine-6(2H)-carboxylate (may be prepared as described in Description 47) (278 mg, 0.65 mmol) in dichloromethane (8 ml) was treated with diisopropylethylamine (0.36 ml, 2.07 mmol) followed by 1,1,1-trifluoro-N-phenyl-N-[(trifluoromethyl)sulfonyl]methanesulfonamide (373 mg, 1.04 mmol) and the resulting solution heated to reflux over 5 min and then kept at this temperature under Argon, for 22.5 h. The mixture was then allowed to cool over 3.5 h and then reduced under vacuum. Purification by chromatography on silica gel eluting with hexane:ethyl acetate 10:1→7:1→5:1→3:1→1:1 afforded the title compound (D48). MS (ES+) m/e 559 [M+H]$^+$.

Description 49

1,1-Dimethylethyl 2-(4-piperidinyl)-4,5,7,8-tetrahydropyrazolo[3,4-d]azepine-6(2H)-carboxylate (D49)

A mixture of 1,1-dimethylethyl 2-[1-(phenylmethyl)-4-piperidinyl]-3-{[(trifluoromethyl)sulfonyl]oxy}-3,3a,4,5,7,8-hexahydropyrazolo[3,4-d]azepine-6(2H)-carboxylate (may be prepared as described in Description 48) (355 mg, 0.64 mmol) in ethyl acetate (9 ml) and methanol (3 ml) was treated with triethylamine (0.443 ml, 3.18 mmol) and then Pd(OH)$_2$/C (20% w/w, 70 mg) and the resulting mixture stirred under an atmosphere of H$_2$ for 18.5 h. The mixture was then filtered through kieselguhr and reduced under vacuum. Purification by Mass Directed Autopreparation afforded the title compound (D49). MS (ES+) m/e 321 [M+H]$^+$.

Description 50

1,1-Dimethylethyl 2-[1-(6-methyl-3-pyridinyl)-4-piperidinyl]-4,5,7,8-tetrahydropyrazolo[3,4-d]azepine-6(2H)-carboxylate (D50)

1,1-Dimethylethyl 2-(4-piperidinyl)-4,5,7,8-tetrahydropyrazolo[3,4-d]azepine-6(2H)-carboxylate (may be prepared as described in Description 49) (65 mg, 0.21 mmol), 5-bromo-2-methylpyridine (52 mg, 0.30 mmol), palladium acetate (5 mg, 0.02 mmol), (+/−) BINAP (25 mg, 0.04 mmol), sodium tert-butoxide (39 mg, 0.041 mmol) and dioxane (2 ml) were mixed and heated to reflux under Argon and kept at this temperature for 14 h. After an additional 1.5 h, more 5-bromo-2-methylpyridine (1.5 eq), palladium acetate (0.1 eq), (+/−) BINAP (0.2 eq) and sodium tert-butoxide (2 eq) were added and the mixture stirred at reflux under Argon for an additional 7 h. the mixture was then allowed to cool over 45 mins and was then diluted with methanol and purified by SCX eluting with methanol, then 2M methanol/NH₃. Purified further by SPE(Si) eluting with dichloromethane:methanol 50:1→25:1→10:1. Further purification by Mass Directed Autopreparation afforded the title compound (D50). MS (ES+) m/e 412 $[M+H]^+$.

EXAMPLE 1

N,N-Dimethyl-4-[6-(2-methylpropyl)-5,6,7,8-tetrahydropyrazolo[3,4-d]azepin-2(4H)-yl]benzamide (E1)

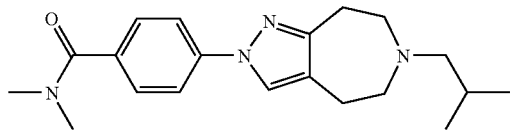

A solution of N,N-dimethyl-4-(5,6,7,8-tetrahydropyrazolo[3,4-d]azepin-2(4H)-yl)benzamide (24.0 mg, 0.085 mmol) (may be prepared as described in Description 42) in dichloromethane (2 ml) was treated with 2-methylpropanal (16.0 μl, 0.17 mmol) and acetic acid (1 drop) and stirred at room temperature. Sodium triacetoxyborohydride (36.0 mg, 0.17 mmol) was added and the mixture was stirred at room temperature for approximately 50 hours. The mixture was diluted with methanol and passed down a SCX cartridge eluting with methanol and then a 2M solution of ammonia in methanol. The basic fractions were combined and evaporated to afford the title compound (E1); MS (ES+) m/e 357 $[M+NH_3]^+$.

EXAMPLE 2

N,N-Dimethyl-4-[6-(1-methylethyl)-5,6,7,8-tetrahydropyrazolo[3,4-d]azepin-2(4)-yl]benzamide (E2)

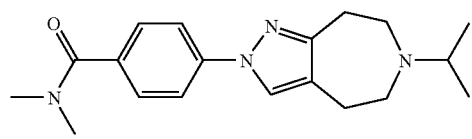

N,N-Dimethyl-4-[6-(1-methylethyl)-5,6,7,8-tetrahydropyrazolo[3,4-d]azepin-2(4H)-yl]benzamide (E2) may be prepared from N,N-dimethyl-4-(5,6,7,8-tetrahydropyrazolo[3,4-d]azepin-2(4H)-yl)benzamide (may be prepared as described in Description 42) (24.0 mg, 0.085 mmol) using an analogous process to that described in Example 1 substituting 2-methylpropanal for acetone. MS (ES+) m/e 327 $[M+H]^+$.

EXAMPLE 3

4-(6-Cyclobutyl-5,6,7,8-tetrahydropyrazolo[3,4-d]azepin-2(4H)-yl)-N,N-dimethylbenzamide (E3)

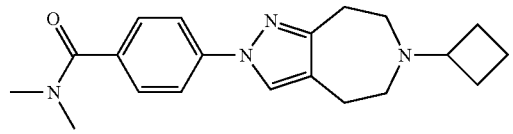

4-(6-Cyclobutyl-5,6,7,8-tetrahydropyrazolo[3,4-d]azepin-2(4H)-yl)-N,N-dimethylbenzamide (E3) may be prepared from N,N-dimethyl-4-(5,6,7,8-tetrahydropyrazolo[3,4-d]azepin-2(4H)-yl)benzamide (may be prepared as described in Description 42) (24.0 mg, 0.085 mmol) using an analogous process to that described in Example 1 substituting 2-methylpropanal for cyclobutanone. MS (ES+) m/e 339 $[M+H]^+$.

EXAMPLE 4

4-(6-Cyclopentyl-5,6,7,8-tetrahydropyrazolo[3,4-d]azepin-2(4H)-yl)-N,N-dimethylbenzamide (E4)

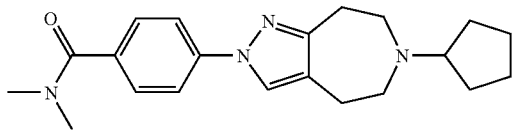

4-(6-Cyclopentyl-5,6,7,8-tetrahydropyrazolo[3,4-d]azepin-2(4H)-yl)-N,N-dimethylbenzamide (E4) may be prepared from N,N-dimethyl-4-(5,6,7,8-tetrahydropyrazolo[3,4-d]azepin-2(4H)-yl)benzamide (may be prepared as described in Description 42) (24.0 mg, 0.085 mmol) using an analogous process to that described in Example 1 substituting 2-methylpropanal for cyclopentanone. MS (ES+) m/e 353 $[M+H]^+$.

EXAMPLE 5

N-Methyl-4-[6-(2-methylpropyl)-5,6,7,8-tetrahydropyrazolo[3,4-d]azepin-2(4H)-yl]benzamide (E5)

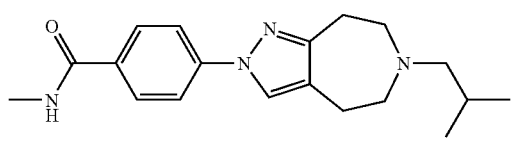

A solution of N-methyl-4-(5,6,7,8-tetrahydropyrazolo[3,4-d]azepin-2(4H)-yl)benzamide (may be prepared as described in Description 25) (30.0 mg, 0.11 mmol) in dichloromethane (3 ml) was treated with 2-methylpropanal (20.0 μl, 0.22 mmol) and acetic acid (1 drop) and stirred at room temperature. Sodium triacetoxyborohydride (47.0 mg, 0.22 mmol) was added and the mixture was stirred at room temperature overnight. The mixture was diluted with methanol and passed down a SCX cartridge eluting with methanol and then a 2M solution of ammonia in methanol. The basic fractions were combined and evaporated to afford the title compound (E5); MS (ES+) m/e 327 [M+NH$_3$]$^+$.

EXAMPLE 6

N-Methyl-4-[6-(1-methylethyl)-5,6,7,8-tetrahydropyrazolo[3,4-d]azepin-2(4H)-yl]benzamide (E6)

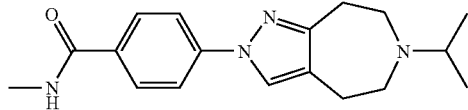

N-Methyl-4-[6-(1-methylethyl)-5,6,7,8-tetrahydropyrazolo[3,4-d]azepin-2(4H)-yl]benzamide (E6) may be prepared from N-methyl-4-(5,6,7,8-tetrahydropyrazolo[3,4-d]azepin-2(4H)-yl)benzamide (may be prepared as described in Description 25) (30.0 mg, 0.11 mmol) using an analogous process to that described in Example 5 substituting 2-methylpropanal for acetone. MS (ES+) m/e 313 [M+H]$^+$.

EXAMPLE 7

4-(6-Cyclobutyl-5,6,7,8-tetrahydropyrazolo[3,4-d]azepin-2(4H)-yl)-N-methylbenzamide (E7)

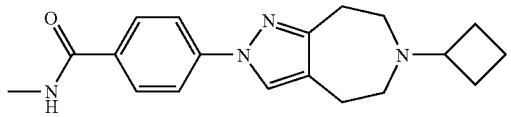

4-(6-Cyclobutyl-5,6,7,8-tetrahydropyrazolo[3,4-d]azepin-2(4H)-yl)-N-methylbenzamide (E7) may be prepared from N-methyl-4-(5,6,7,8-tetrahydropyrazolo[3,4-d]azepin-2(4H)-yl)benzamide (may be prepared as described in Description 25) (30.0 mg, 0.11 mmol) using an analogous process to that described in Example 5 substituting 2-methylpropanal for cyclobutanone. MS (ES+) m/e 325 [M+H]$^+$.

EXAMPLE 8

4-(6-Cyclopentyl-5,6,7,8-tetrahydropyrazolo[3,4-d]azepin-2(4H)-yl)-N-methylbenzamide (E8)

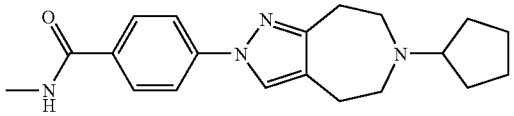

4-(6-Cyclopentyl-5,6,7,8-tetrahydropyrazolo[3,4-d]azepin-2(4H)-yl)-N-methylbenzamide (E8) may be prepared from N-methyl-4-(5,6,7,8-tetrahydropyrazolo[3,4-d]azepin-2(4H)-yl)benzamide (may be prepared as described in Description 25) (30.0 mg, 0.11 mmol) using an analogous process to that described in Example 5 substituting 2-methylpropanal for cyclopentanone. MS (ES+) m/e 339 [M+H]$^+$.

EXAMPLE 9

3-{4-[6-(1-Methylethyl)-5,6,7,8-tetrahydropyrazolo[3,4-d]azepin-2(4H)-yl]phenyl}-1,3-oxazolidin-2-one (E9)

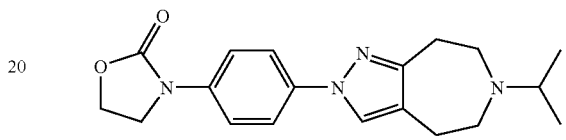

A solution of 3-[4-(5,6,7,8-tetrahydropyrazolo[3,4-d]azepin-2(4H)-yl)phenyl]-1,3-oxazolidin-2-one (25.0 mg, 0.08 mmol) (may be prepared as described in Description 27) in dichloromethane (3 ml) was treated with acetone (25.0 μl, 0.34 mmol) and acetic acid (1 drop) and stirred at room temperature. Sodium triacetoxyborohydride (72.0 mg, 0.34 mmol) was added and the mixture stirred for 3 hours and then overnight. The mixture was diluted with methanol and passed down a SCX cartridge eluting with methanol and then a 2M solution of ammonia in methanol. The basic fractions were combined and evaporated to afford the title compound (E9); MS (ES+) m/e 341 [M+H]$^+$.

EXAMPLE 10

1-Methyl-3-{4-[6-(1-methylethyl)-5,6,7,8-tetrahydropyrazolo[3,4-d]azepin-2(4H)-yl]phenyl}-2-imidazolidinone (E10)

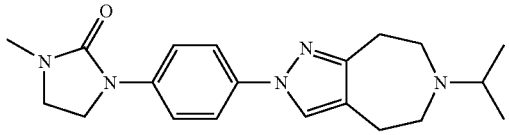

A solution of 1-methyl-3-[4-(5,6,7,8-tetrahydropyrazolo[3,4-d]azepin-2(4H)-yl)phenyl]-2-imidazolidinone (may be prepared as described in Description 29) (44.0 mg, 0.14 mmol) in dichloromethane (3 ml) was treated with acetone (41 μl, 0.56 mmol) and acetic acid (1 drop) and stirred at room temperature. Sodium triacetoxyborohydride (60.0 mg, 0.28 mmol) was added and the mixture stirred for 3 hours and then overnight with a further portion of acetone and sodium triacetoxyborohydride added. The mixture was diluted with methanol and passed down a SCX cartridge eluting with methanol and then a 2M solution of ammonia in methanol. The basic fractions were combined and evaporated to afford the title compound (E10); MS (ES+) m/e 354 [M+H]$^+$.

EXAMPLE 11

1-Methyl-3-{4-[6-(2-methylpropyl)-5,6,7,8-tetrahydropyrazolo[3,4-d]azepin-2(4H)-yl]phenyl}-2-imidazolidinone (E11)

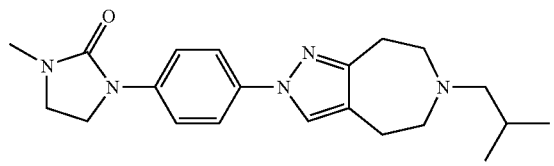

1-Methyl-3-{4-[6-(2-methylpropyl)-5,6,7,8-tetrahydropyrazolo[3,4-d]azepin-2(4H)-yl]phenyl}-2-imidazolidinone (E11) may be prepared from 1-methyl-3-[4-(5,6,7,8-tetrahydropyrazolo[3,4-d]azepin-2(4H)-yl)phenyl]-2-imidazolidinone (may be prepared as described in Description 29) (44.0 mg, 0.14 mmol) using an analogous process to that described in Example 10 substituting acetone for 2-methylpropanal. MS (ES+) m/e 368 [M+H]⁺.

EXAMPLE 12

1-[5-(6-Cyclobutyl-5,6,7,8-tetrahydropyrazolo[3,4-d]azepin-2(4H)-y)-2-pyridinyl]-2-pyrrolidinone (E12)

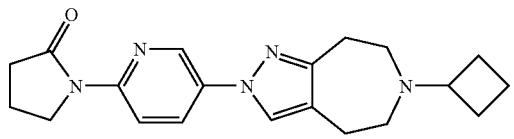

Method A

To a solution of 1-[5-(5,6,7,8-tetrahydropyrazolo[3,4-d]azepin-2(4H)-yl)-2-pyridinyl]-2-pyrrolidinone (may be prepared as described in Description 19) (12.0 mg, 0.04 mmol) in dichloromethane (2 ml) and acetic acid (2 drops) was added cyclobutanone (5.0 μl, 0.06 mmol). The resulting mixture was allowed to stir at RT for 10 mins. Sodium triacetoxyborohydride (13.0 mg, 0.06 mmol) was then added and stirring continued for 1 hour. The reaction mixture was diluted with methanol and applied to a SCX cartridge (Varian bond-elute, 5 g) and washed with methanol followed by a mixture of 2M ammonia/methanol. The basic fractions were combined, evaporated and purified further by chromatography on silica, eluting with a mixture of 2M ammonia in methanol/dichloromethane (0-3%) to afford the title compound (E12). MS (ES+) m/e 352 [M+H]⁺.

Method B

To a solution of 1-[5-(5,6,7,8-tetrahydropyrazolo[3,4-d]azepin-2(4H)-yl)-2-pyridinyl]-2-pyrrolidinone (may be prepared as described in Description 19) (12.0 mg, 0.04 mmol) in dichloromethane (2 ml) and acetic acid (2 drops) was added cyclobutanone (5.00 μl, 0.06 mmol), followed by sodium triacetoxyborohydride (13.0 mg, 0.06 mmol). The resulting mixture was allowed to stir at room temperature for 1 hour, diluted with methanol and passed down a 5 g SCX cartridge, eluting with methanol then a 2M ammonia in methanol solution. The basic fraction were combined, evaporated and purified by column chromatography eluting with a mixture of 2M ammonia in methanol and dichloromethane (0-3%) to afford the product (E12); MS (ES+) m/e 352 [M+H]⁺.

Method C

To a solution of 1-[5-(5,6,7,8-tetrahydropyrazolo[3,4-d]azepin-2(4H)-yl)-2-pyridinyl]-2-pyrrolidinone (may be prepared as described in Description 19) (11 mg, 0.04 mmol) in dichloromethane (3 ml) was added cyclobutanone (6 μl, 0.08 mmol) followed by acetic acid (2 drops) and sodium triacetoxyborohydride (17 mg, 0.08 mmol). The mixture was stirred at room temperature for 2 hours, then it was diluted with methanol and purified by SCX cartridge to afford the title compound (E12). MS (ES+) m/e 352 [M+H]⁺.

EXAMPLE 13

1-[4-(6-Cyclobutyl-5,6,7,8-tetrahydropyrazolo[3,4-d]azepin-2(4-yl)phenyl]-2-pyrrolidinone (E13)

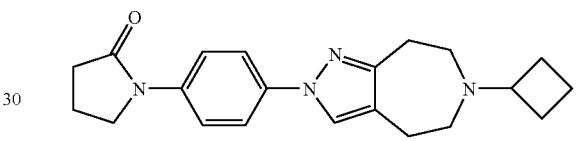

Method A

To a solution of 1-[4-(5,6,7,8-tetrahydropyrazolo[3,4-d]azepin-2(4H)-yl)phenyl]-2-pyrrolidinone (may be prepared as described in Description 22) (10.0 mg, 0.03 mmol) in dichloromethane (2 ml) and acetic acid (2 drops) was added cyclobutanone (4.0 μl, 0.05 mmol). The resulting mixture was allowed to stir at room temperature for 10 mins. Sodium triacetoxyborohydride (11.0 mg, 0.05 mmol) was then added and stirring continued for 1 hour. The reaction mixture was diluted with methanol and applied to a SCX cartridge (Varian bond-elute, 5 g) and washed with methanol followed by a mixture of 2M ammonia/methanol. The basic fractions were combined, evaporated and purified further by chromatography on silica, eluting with a mixture of 2M ammonia in methanol/dichloromethane (0-3%) to afford the title compound (E13). MS (ES+) m/e 351 [M+H]⁺.

Method B

To a solution of 1-[4-(5,6,7,8-tetrahydropyrazolo[3,4-d]azepin-2(4H)-yl)phenyl]-2-pyrrolidinone (may be prepared as described in Description 22) (32.0 mg, 0.11 mmol) in dichloromethane (2 ml) and acetic acid (2 drops) was added cyclobutanone (12.0 μl, 0.16 mmol), followed by sodium triacetoxyborohydride (34.0 mg, 0.16 mmol) after approximately 10 minutes. The mixture was allowed to stir at room temperature for 30 minutes before a further portion of cyclobutanone (12.0 μl, 0.16 mmol) and sodium triacetoxyborohydride (34.0 mg, 0.16 mmol) were added. After stirring at room temperature for 30 minutes the reaction was quenched with methanol and passed down a 2 g SCX cartridge, eluting with methanol then a 2M ammonia in methanol solution. The basic fraction were combined and evaporated to afford the product (E13); MS (ES+) m/e 351 [M+H]⁺.

Method C

A mixture of 1-[4-(5,6,7,8-tetrahydropyrazolo[3,4-d]azepin-2(4H)-yl)phenyl]-2-pyrrolidinone (may be prepared as described in Description 22) (65 mg, 0.22 mmol) in dichloromethane (4 ml) was treated with cyclobutanone (0.033 ml, 0.44 mmol) followed by sodium triacetoxyborohydride (93 mg, 0.44 mmol). The resulting mixture was then stirred under Argon for 14.25 hours. The mixture was then diluted with methanol (5 ml) and purified by SCX eluting with methanol and then ammonia/methanol (2M). The appropriate fractions were combined, reduced and triturated with diethyl ether to afford the product (E13).

EXAMPLE 14

1-{4-[6-(1-Methylethyl)-5,6,7,8-tetrahydropyrazolo[3,4-d]azepin-2(4H)-yl]phenyl}-2-pyrrolidinone (E14)

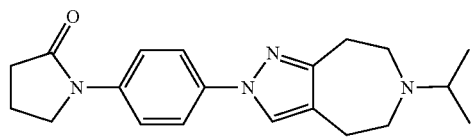

To a solution of 1-[4-(5,6,7,8-tetrahydropyrazolo[3,4-d]azepin-2(4H)-yl)phenyl]-2-pyrrolidinone (may be prepared as described in Description 22) (45 mg, 0.15 mmol) in dichloromethane (3 ml) was added acetone (17 mg, 0.30 mmol) and acetic acid (2 drops). The resulting mixture was stirred at room temperature, under argon, for 20 minutes. Sodium triacetoxyborohydride (64 mg, 0.30 mmol) was added and stirring continued for 22 hours. A further 2 eq. of acetone (17 mg, 0.30 mmol) was added, and after a further 20 minutes a further 2 eq. of sodium triacetoxyborohydride (64 mg, 0.30 mmol) was added and stirring continued for 3 hours. The resulting crude mixture was diluted with methanol and then purified by SCX, eluting with methanol and then with 2M ammonia/methanol. The basic fractions were combined and solvent evaporated in vacuo. Crude product was triturated with ether, filtered then triturated with ethyl acetate to afford the title compound (E14). MS (ES+) m/e 339 [M+H]⁺.

EXAMPLE 15

6-(1-Methylethyl)-2-[4-(3-methyl-1,2,4-oxadiazol-5-yl)phenyl]-2,4,5,6,7,8-hexahydropyrazolo[3,4-d]azepine (E15)

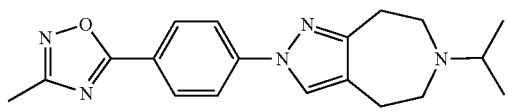

To a solution of 2-[4-(3-methyl-1,2,4-oxadiazol-5-yl)phenyl]-2,4,5,6,7,8-hexahydropyrazolo[3,4-d]azepine (may be prepared as described in Description 35) (31 mg, 0.10 mmol) in dichloromethane (4 ml) was added acetone (24 mg, 0.42 mmol) and acetic acid (3 drops). The resulting mixture was stirred at room temperature, under argon, for 20 minutes. Sodium triacetoxyborohydride (89 mg, 0.42 mmol) was added and stirring continued overnight. The resulting crude mixture was diluted with methanol and then purified by SCX, eluting with methanol and then with 2M ammonia/methanol. The basic fractions were combined and solvent evaporated in vacuo. Crude product was purified further by column chromatography on silica gel, eluting with a mixture of 2M ammonia in methanol/dichloromethane (0-1%). Resulting crude product was purified further by column chromatography on silica gel, eluting with a mixture of 2M ammonia in methanol/dichloromethane (0-1%) to afford the title compound (E15). MS (ES+) m/e 338 [M+H]⁺.

EXAMPLE 16

4-[6-(2-Methylpropyl)-5,6,7,8-tetrahydropyrazolo[3,4-d]azepin-2(4H)-yl]benzamide (E16)

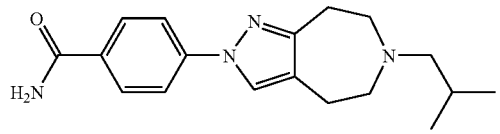

To a solution of 4-(5,6,7,8-tetrahydropyrazolo[3,4-d]azepin-2(4H)-yl)benzamide (may be prepared as described in Description 37) (31 mg, 0.12 mmol) in dichloromethane (3 ml) was added 2-methylpropanal (17 mg, 0.24 mmol) and acetic acid (2 drops). The resulting mixture was stirred at room temperature, under argon, for 20 minutes. Sodium triacetoxyborohydride (51 mg, 0.24 mmol) was added and stirring continued for 2 hours. The resulting crude mixture was diluted with methanol and then purified by SCX, eluting with methanol and then with 2M ammonia/methanol. The basic fractions were combined and solvent evaporated in vacuo to afford the title compound (E16). MS (ES+) m/e 313 [M+H]⁺.

EXAMPLE 17

4-[6-(1-Methylethyl)-5,6,7,8-tetrahydropyrazolo[3,4-d]azepin-2(4H)-yl]benzamide (E17)

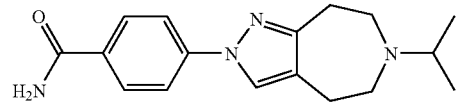

To a solution of 4-(5,6,7,8-tetrahydropyrazolo[3,4-d]azepin-2(4H)-yl)benzamide (may be prepared as described in Description 37) (31 mg, 0.12 mmol) in dichloromethane (3 ml) was added acetone (14 mg, 0.24 mmol) and acetic acid (2 drops). The resulting mixture was stirred at room temperature, under argon, for 20 minutes. Sodium triacetoxyborohydride (51 mg, 0.24 mmol) was added and stirring continued for 2 hours. A further 6 eq. of acetone was added and stirring continued over the weekend. Methanol was added and the crude mixture was purified by SCX, eluting with methanol and then with 2M ammonia/methanol. The basic fractions were combined and solvent evaporated in vacuo. The crude product was triturated with ether and filtered to afford the title compound (E17). MS (ES+) m/e 299 [M+H]⁺.

EXAMPLE 18

1-[4-(6-Ethyl-5,6,7,8-tetrahydropyrazolo[3,4-d]azepin-2(4H)-yl)phenyl]-2-pyrrolidinone (E18)

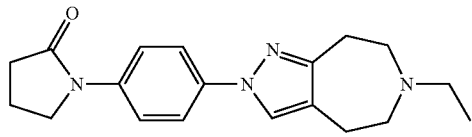

To a solution of 1-[4-(5,6,7,8-tetrahydropyrazolo[3,4-d]azepin-2(4H)-yl)phenyl]-2-pyrrolidinone (may be prepared as described in Description 22) (50 mg, 0.17 mmol) in ethanol (5 ml) was added potassium carbonate (70 mg, 0.51 mmol) and iodoethane (53 mg, 0.34 mmol). The resulting mixture was heated at reflux, under argon, for 18 hours. A further 3 eq. of potassium carbonate in ethanol (2 ml) was added, and stirring continued over the weekend. Reaction was removed from heat and ethanol (~20 ml) was added. Reaction was purified by SCX, eluting with methanol and then with 2M ammonia/methanol. The basic fractions were combined and solvent evaporated in vacuo. The resulting crude product was purified further by column chromatography on silica gel eluting with a mixture of methanol in dichloromethane (100:1-10:1) to afford the title compound (E18). MS (ES+) m/e 325 [M+H]$^+$.

EXAMPLE 19

1-{4-[6-(Cyclopropylmethyl)-5,6,7,8-tetrahydropyrazolo[3,4-d]azepin-2(4H)-yl]phenyl}-2-pyrrolidinone (E19)

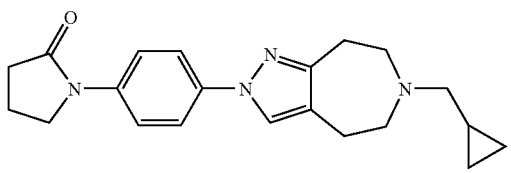

To a solution of 1-[4-(5,6,7,8-tetrahydropyrazolo[3,4-d]azepin-2(4H)-yl)phenyl]-2-pyrrolidinone (may be prepared as described in Description 22) (55 mg, 0.10 mmol) in dichloromethane (5 ml) was added cyclopropylacetaldehyde (26 mg, 0.30 mmol) and acetic acid (3 drops). The resulting mixture was stirred at room temperature, under argon, for 20 minutes. Sodium triacetoxyborohydride (64 mg, 0.30 mmol) was added and stirring continued for 18 hours. The resulting crude mixture was diluted with methanol and then purified by SCX, eluting with methanol and then with 2M ammonia/methanol. The basic fractions were collected and solvent evaporated in vacuo. Crude product was triturated with ethyl acetate to afford the title compound (E19). MS (ES+) m/e 351 [M+H]$^+$.

EXAMPLE 20

1-{4-[6-(2-Methylpropyl)-5,6,7,8-tetrahydropyrazolo[3,4-d]azepin-2(4'-yl]phenyl}-2-pyrrolidinone (E20)

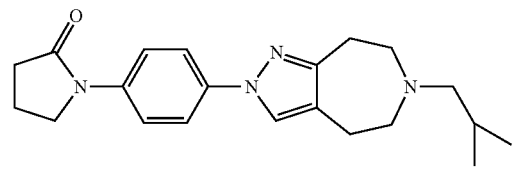

To a solution of 1-[4-(5,6,7,8-tetrahydropyrazolo[3,4-d]azepin-2(4H)-yl)phenyl]-2-pyrrolidinone (may be prepared as described in Description 22) (55 mg, 0.10 mmol) in dichloromethane (5 ml) was added 2-methylpropanal (27 mg, 0.30 mmol) and acetic acid (3 drops). The resulting mixture was stirred at room temperature, under argon, for 20 minutes. Sodium triacetoxyborohydride (64 mg, 0.30 mmol) was added and stirring continued for 18 hours. The resulting crude mixture was diluted with methanol and then purified by SCX, eluting with methanol and then with 2M ammonia/methanol. The basic fractions were combined and solvent evaporated in vacuo. Crude product was triturated with ethyl acetate to afford the title compound (E20). MS (ES+) m/e 353 [M+H]$^+$.

EXAMPLE 21

2-[4-(3-Methyl-1,2,4-oxadiazol-5-yl)phenyl]-6-(2-methylpropyl)-2,4,5,6,7,8-hexahydropyrazolo[3,4-d]azepine (E21)

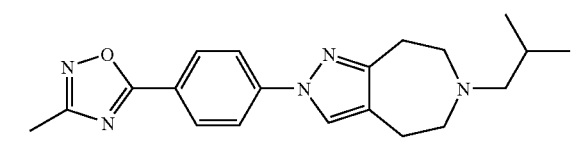

To a solution of 2-[4-(3-methyl-1,2,4-oxadiazol-5-yl)phenyl]-2,4,5,6,7,8-hexahydropyrazolo[3,4-d]azepine (may be prepared as described in Description 35) (31 mg, 0.10 mmol) in dichloromethane (4 ml) was added 2-methylpropanal (30 mg, 0.42 mmol) and acetic acid (3 drops). The resulting mixture was stirred at room temperature, under argon, for 20 minutes. Sodium triacetoxyborohydride (89 mg, 0.42 mmol) was added and stirring continued overnight. The resulting crude mixture was diluted with methanol and then purified by SCX, eluting with methanol and then with 2M ammonia/methanol. The basic fractions were combined and solvent evaporated in vacuo. Crude product was purified further by column chromatography on silica gel, eluting with a mixture of 2M ammonia in methanol in dichloromethane (0-1%) to afford the title compound (E21). MS (ES+) m/e 352 [M+H]$^+$.

EXAMPLE 22

1-[4-(6-Cyclohexyl-5,6,7,8-tetrahydropyrazolo[3,4-d]azepin-2(4H)-yl)phenyl]-2-pyrrolidinone (E22)

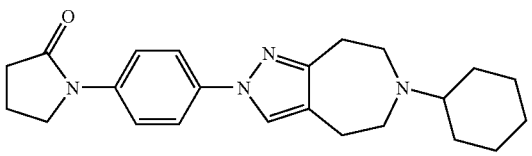

To a solution of 1-[4-(5,6,7,8-tetrahydropyrazolo[3,4-d]azepin-2(4H)-yl)phenyl]-2-pyrrolidinone (may be prepared as described in Description 22) (45 mg, 0.15 mmol) in dichloromethane (3 ml) was added cyclohexanone (29 mg, 0.30 mmol) and acetic acid (2 drops). The resulting mixture was stirred at room temperature, under argon, for 20 minutes. Sodium triacetoxyborohydride (64 mg, 0.30 mmol) was added and stirring continued for 22 hours. A further 2 eq. of cyclohexanone (29 mg, 0.30 mmol) was added, and after a further 20 minutes a further 2 eq. of sodium triacetoxyborohydride (64 mg, 0.30 mmol) was added and stirring continued for 3 hours. The resulting crude mixture was diluted with methanol and then purified by SCX, eluting with methanol and then with 2M ammonia/methanol. The basic fractions were combined and solvent evaporated in vacuo to afford the title compound (E22). MS (ES+) m/e 379 [M+H]+.

EXAMPLE 23

4-(6-Cyclopentyl-5,6,7,8-tetrahydropyrazolo[3,4-d]azepin-2(4H)-yl)benzamide (E23)

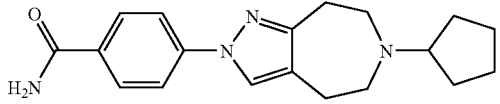

To a solution of 4-(5,6,7,8-tetrahydropyrazolo[3,4-d]azepin-2(4H)-yl)benzamide (may be prepared as described in Description 37) (31 mg, 0.12 mmol) in dichloromethane (3 ml) was added cyclopentanone (20 mg, 0.24 mmol) and acetic acid (2 drops). The resulting mixture was stirred at room temperature, under argon, for 20 minutes. Sodium triacetoxyborohydride (51 mg, 0.24 mmol) was added and stirring continued for 2 hours. A further 6 eq. of cyclopentanone was added and stirring continued over the weekend. Methanol was added and the crude mixture was purified by SCX, eluting with methanol and then with 2M ammonia/methanol. The basic fractions were combined and solvent evaporated in vacuo to afford the title compound (E23). MS (ES+) m/e 325 [M+H]+.

EXAMPLE 24

1-[4-(6-Cyclopentyl-5,6,7,8-tetrahydropyrazolo[3,4-d]azepin-2(4H)-yl)phenyl]-2-pyrrolidinone (E24)

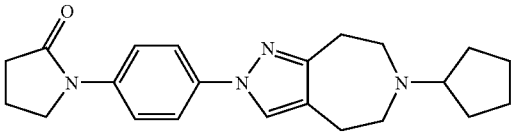

To a solution of 1-[4-(5,6,7,8-tetrahydropyrazolo[3,4-d]azepin-2(4H)-yl)phenyl]-2-pyrrolidinone (may be prepared as described in Description 22) (45 mg, 0.15 mmol) in dichloromethane (3 ml) was added cyclopentanone (26 mg, 0.30 mmol) and acetic acid (2 drops). The resulting mixture was stirred at room temperature, under argon, for 20 minutes. Sodium triacetoxyborohydride (64 mg, 0.30 mmol) was added and stirring continued for 1.5 hours. The resulting crude mixture was diluted with methanol and then purified by SCX, eluting with methanol and then with 2M ammonia/methanol. The basic fractions were combined and solvent evaporated in vacuo. Crude product was triturated with ether to afford the title compound (E24). MS (ES+) m/e 365 [M+H]+.

EXAMPLE 25

6-Cyclobutyl-2-[4-(3-methyl-1,2,4-oxadiazol-5-yl)phenyl]-2,4,5,6,7,8-hexahydropyrazolo[3,4-d]azepine (E25)

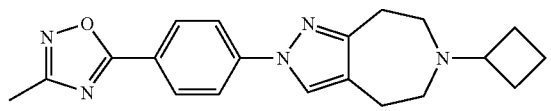

To a solution of 2-[4-(3-methyl-1,2,4-oxadiazol-5-yl)phenyl]-2,4,5,6,7,8-hexahydropyrazolo[3,4-d]azepine (prepared as described in Description 35) (31 mg, 0.10 mmol) in dichloromethane (4 ml) was added cyclobutanone (30 mg, 0.42 mmol) and acetic acid (3 drops). The resulting mixture was stirred at room temperature, under argon, for 20 minutes. Sodium triacetoxyborohydride (89 mg, 0.42 mmol) was added and stirring continued overnight. The resulting crude mixture was diluted with methanol and then purified by SCX, eluting with methanol and then with 2M ammonia/methanol. The basic fractions were combined and solvent evaporated in vacuo to afford the title compound (E25). MS (ES+) m/e 350 [M+H]+.

EXAMPLE 26

4-(6-Cyclobutyl-5,6,7,8-tetrahydropyrazolo[3,4-d]azepin-2(4H)-yl)benzamide (E26)

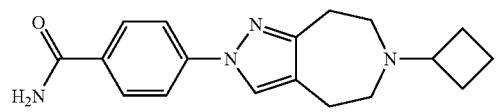

To a solution of 4-(5,6,7,8-tetrahydropyrazolo[3,4-d]azepin-2(4H)-yl)benzamide (may be prepared as described in Description 37) (31 mg, 0.12 mmol) in dichloromethane (3 ml) was added cyclobutanone (17 mg, 0.24 mmol) and acetic acid (2 drops). The resulting mixture was stirred at room temperature, under argon, for 20 minutes. Sodium triacetoxyborohydride (51 mg, 0.24 mmol) was added and stirring continued for 2 hours. Methanol was added and the crude mixture was purified by SCX, eluting with methanol and then with 2M ammonia/methanol. The basic fractions were combined and solvent evaporated in vacuo to afford the title compound (E26). MS (ES+) m/e 311 [M+H]+.

EXAMPLE 27

6-Cyclopentyl-2-[4-(3-methyl-1,2,4-oxadiazol-5-yl)phenyl]-2,4,5,6,7,8-hexahydropyrazolo[3,4-d]azepine (E27)

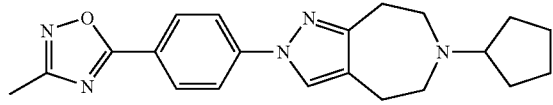

To a solution of 2-[4-(3-methyl-1,2,4-oxadiazol-5-yl)phenyl]-2,4,5,6,7,8-hexahydropyrazolo[3,4-d]azepine (may be prepared as described in Description 35) (31 mg, 0.10 mmol) in dichloromethane (4 ml) was added cyclopentanone (35 mg, 0.42 mmol) and acetic acid (3 drops). The resulting mixture was stirred at room temperature, under argon, for 20 minutes. Sodium triacetoxyborohydride (89 mg, 0.42 mmol) was added and stirring continued overnight. The resulting crude mixture was diluted with methanol and then purified by SCX, eluting with methanol and then with 2M ammonia/methanol. The basic fractions were combined and solvent evaporated in vacuo to afford the title compound (E27). MS (ES+) m/e 364 [M+H]+.

EXAMPLE 28

6-Cyclobutyl-2-[4-(methylsulfonyl)phenyl]-2,4,5,6,7,8-hexahydropyrazolo[3,4-d]azepine (E28)

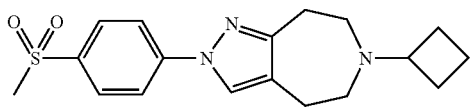

To a solution of 2-[4-(methylsulfonyl)phenyl]-2,4,5,6,7,8-hexahydropyrazolo[3,4-d]azepine (may be prepared as described in Description 38) (4 mg, 0.014 mmol) in dichloromethane (2 ml) was added cyclobutanone (7 mg, 0.096 mmol) and acetic acid (1 drop). The resulting mixture was stirred at room temperature, under argon, for 20 minutes. Sodium triacetoxyborohydride (20 mg, 0.096 mmol) was added and stirring continued overnight. The resulting reaction mixture was diluted with methanol and purified by SCX, eluting with methanol and then with 2M ammonia/methanol. The basic fractions were combined and solvent evaporated in vacuo to afford the title compound (E28). MS (ES+) m/e 346 [M+H]+.

EXAMPLE 29

N-[4-(6-Cyclobutyl-5,6,7,8-tetrahydropyrazolo[3,4-d]azepin-2(4H)-yl)phenyl]methanesulfonamide (E29)

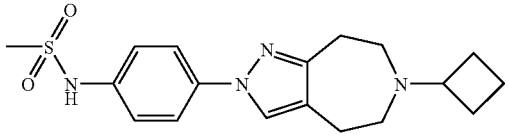

To a solution of N-[4-(5,6,7,8-tetrahydropyrazolo[3,4-d]azepin-2(4H)-yl)phenyl]methanesulfonamide (may be prepared as described in Description 40) (12 mg, 0.04 mmol) in dichloromethane (2 ml) was added cyclobutanone (14 mg, 0.20 mmol) and acetic acid (1 drop). The resulting mixture was stirred at room temperature, under argon, for 30 minutes. Sodium triacetoxyborohydride (42 mg, 0.20 mmol) was added and stirring continued for 1 hour. The resulting reaction mixture was diluted with methanol and purified by SCX, eluting with methanol and then with 2M ammonia/methanol. The basic fractions were combined and solvent evaporated in vacuo to afford the title compound (E29). MS (ES+) m/e 361 [M+H]+.

EXAMPLE 30

3-[4-(6-Cyclopentyl-5,6,7,8-tetrahydropyrazolo[3,4-d]azepin-2(4'-yl)phenyl]-1,3-oxazolidin-2-one (E30)

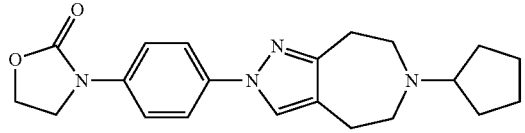

To a solution of 3-[4-(5,6,7,8-tetrahydropyrazolo[3,4-d]azepin-2(4H)-yl)phenyl]-1,3-oxazolidin-2-one (may be prepared as described in Description 27) (35 mg, 0.12 mmol) in dichloromethane (4 ml) was added cyclopentanone (40 mg, 0.47 mmol) and acetic acid (3 drops). The resulting mixture was stirred at room temperature, under argon, for 20 minutes. Sodium triacetoxyborohydride (42 mg, 0.20 mmol) was added and stirring continued overnight. The reaction was diluted with methanol and then purified by SCX, eluting with methanol and then with 2M ammonia/methanol. The basic fractions were combined and solvent evaporated in vacuo to afford the title compound (E30). MS (ES+) m/e 367 [M+H]+.

EXAMPLE 31

1-[4-(6-Cyclopentyl-5,6,7,8-tetrahydropyrazolo[3,4-d]azepin-2(4-yl)phenyl]-3-methyl-2-imidazolidinone (E31)

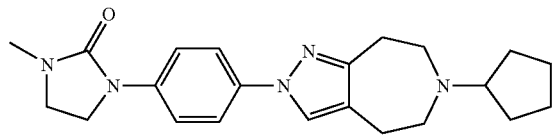

To a solution of 1-methyl-3-[4-(5,6,7,8-tetrahydropyrazolo[3,4-d]azepin-2(4H)-yl)phenyl]-2-imidazolidinone (may be prepared as described in Description 29) (21 mg, 0.07 mmol) in dichloromethane (3 ml) was added cyclopentanone (23 mg, 0.27 mmol) and acetic acid (2 drops). The resulting mixture was stirred at room temperature, under argon, for 40 minutes. Sodium triacetoxyborohydride (42 mg, 0.20 mmol) was added and stirring continued for 4 hours. A further 4 eq. of cyclopentanone was added, and after a further 20 minutes a further 4 eq. of sodium triacetoxyborohydride was added and stirring continued overnight. The reaction was diluted with methanol and then purified by SCX, eluting with methanol and then with 2M ammonia/methanol. The basic fractions were combined and solvent evaporated in vacuo. The resulting crude product was purified further by column chromatography on silica gel, eluting with a mixture of 2M ammonia in methanol/dichloromethane (0-4%) to afford the title compound (E31). MS (ES+) m/e 380 [M+H]$^+$.

EXAMPLE 32

4-(6-Cyclobutyl-5,6,7,8-tetrahydropyrazolo[3,4-d]azepin-2(4H)-yl)benzonitrile (E32)

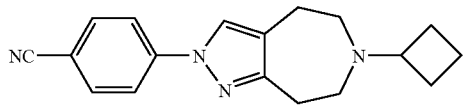

4-(5,6,7,8-Tetrahydropyrazolo[3,4-d]azepin-2(4H)-yl)benzonitrile (may be prepared as described in Description 11) (assumed 0.148 mmol) was dissolved in dichloromethane (2 ml) and acetic acid (2 drops). Cyclobutanone (17 μl, 0.22 mmol) and sodium triacetoxyborohydride (47 mg, 0.22 mmol) were added and the mixture stirred at room temperature for 1 hour. Methanol was added and the solution poured onto a 2 g SCX column which was eluted with methanol then 2M ammonia in methanol. The basic fractions were evaporated and the residue purified by flash chromatography eluting with 0-5% 2M ammonia in methanol/dichloromethane to give the title compound (E32).

EXAMPLE 33

4-[6-(2-Methylpropyl)-5,6,7,8-tetrahydropyrazolo[3,4-d]azepin-2(4H)-yl]benzonitrile (E33)

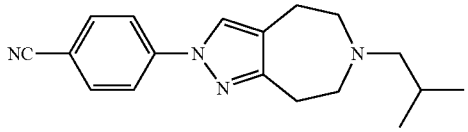

The title compound was prepared using an analogous process to that described in Example 32. MS (ES+) m/e 295 [M+H]$^+$

EXAMPLE 34

4-[6-(1-Methylethyl)-5,6,7,8-tetrahydropyrazolo[3,4-d]azepin-2(4H)-yl]benzonitrile (E34)

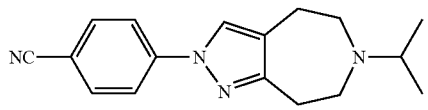

4-(5,6,7,8-Tetrahydropyrazolo[3,4-d]azepin-2(4H)-yl)benzonitrile (may be prepared as described in Description 11) (assumed 0.148 mmol) was dissolved in dichloromethane (2 ml) and acetic acid (2 drops). Acetone (16 μl, 0.22 mmol) and sodium triacetoxyborohydride (47 mg, 0.22 mmol) were added and the mixture stirred at room temperature for 2 hours. Further aliquots of acetone (32 μl, 0.44 mmol) and sodium triacetoxyborohydride (47 mg, 0.22 mmol) were added and stirring continued for a further 70 hours. Methanol was added and the solution poured onto a 2 g SCX column which was eluted with methanol then 2M ammonia in methanol. The basic fractions were evaporated and the residue purified by flash chromatography eluting with 0-5% 2M ammonia in methanol/dichloromethane to afford the title compound (E34).

EXAMPLE 35

2-(4-Bromophenyl)-6-cyclobutyl-2,4,5,6,7,8-hexahydropyrazolo[3,4-d]azepine (E35)

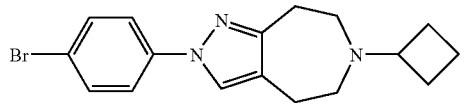

Method A

A mixture of 6-cyclobutyl-2,4,5,6,7,8-hexahydropyrazolo[3,4-d]azepine (may be prepared as described in Description 31) (110 mg, 0.58 mmol), 4-bromophenylboronic acid (233 mg, 1.16 mmol; commercially available from e.g. Aldrich), copper acetate (315 mg, 1.74 mmol), pyridine (94 μl, 1.16 mmol) and molecular sieves (4 Å, 400 mg) in dichloromethane (5 ml) was stirred open to the atmosphere for 60 hours. Crude mixture was then filtered through a pad of celite and washed with methanol. After evaporation in vacuo the residue was purified by SCX cartridge followed by column chromatography on silica gel eluting with a mixture of 2M ammonia in methanol/dichloromethane (0-5%) to afford the title compound (E35). MS (ES+) m/e 346 and 348 [M+H]$^+$. The column also afforded a mixture of the title compound and its regioisomer 1-(4-bromophenyl)-6-cyclobutyl-1,4,5,6,7,8-hexahydropyrazolo[3,4-d]azepine in a 3:1 mixture.

Method B

A mixture of 6-cyclobutyl-2,4,5,6,7,8-hexahydropyrazolo[3,4-d]azepine (may be prepared as described in Description 31) (640 mg, 3.35 mmol), 4-bromophenylboronic acid (1.35 g, 6.7 mmol), copper acetate (1.82 g, 10 mmol), pyridine (540

µl, 6.7 mmol) and molecular sieves (4 Å, 2.4 g) in dichloromethane (30 ml) was stirred open to the atmosphere for 60 hours. Crude mixture was then filtered through a pad of celite and washed with methanol. After evaporation in vacuo the residue was purified by SCX cartridge followed by column chromatography on silica gel eluting with a mixture of 2M ammonia in methanol/dichloromethane (0-5%). Product was further purified by chromatography on reverse phase silica gel eluting with a mixture of acetonitrile in water (5-100%). MS (ES+) m/e 346 and 348 [M+H]$^+$.

EXAMPLE 36

1-[4-(6-Cyclobutyl-5,6,7,8-tetrahydropyrazolo[3,4-d]azepin-2(4-yl)phenyl]-3-methyl-2-imidazolidinone (E36)

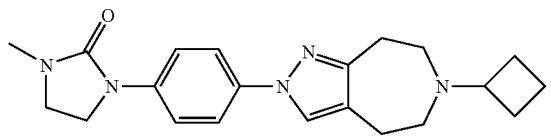

A 3:1 mixture of 2-(4-bromophenyl)-6-cyclobutyl-2,4,5,6,7,8-hexahydropyrazolo[3,4-d]azepine and 1-(4-bromophenyl)-6-cyclobutyl-1,4,5,6,7,8-hexahydropyrazolo[3,4-d]azepine (may be prepared as described in Example 35, method A) (53 mg, 0.15 mmol) in dioxane (5 ml) was treated with 1-methyl-2-imidazolidinone (30 mg, 0.30 mmol), potassium carbonate (62 mg, 0.45 mmol), copper (I) iodide (9.5 mg, 0.05 mmol) and N,N'-dimethyl-1,2-ethanediamine (6 µl, 0.05 mmol). The mixture was heated to reflux for 15 hours. The same amounts again of 1-methyl-2-imidazolidinone, potassium carbonate, copper (I) iodide and N,N'-dimethyl-1,2-ethanediamine were added and the mixture heated to reflux for 20 hours. The same amounts again of 1-methyl-2-imidazolidinone, potassium carbonate, copper (I) iodide and N,N'-dimethyl-1,2-ethanediamine were added and the mixture heated to reflux for 60 hours. The crude mixture was then transferred to a microwave vial, the same amounts of 1-methyl-2-imidazolidinone, potassium carbonate, copper (I) iodide and N,N'-dimethyl-1,2-ethanediamine were added and the mixture heated in the microwave at 150° C. for 4 hours. Mixture was purified by SCX cartridge, followed by Mass Directed Autopreparation and chromatography on silica gel, eluting with a mixture of 2M ammonia in methanol/dichloromethane (0-5%) to afford the title compound (E36). MS (ES+) m/e 366 [M+H]$^+$.

EXAMPLE 37

3-[4-(6-Cyclobutyl-5,6,7,8-tetrahydropyrazolo[3,4-d]azepin-2(4H)-yl)phenyl]-1,3-oxazolidin-2-one (E37)

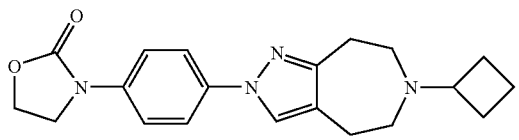

A mixture of 2-(4-bromophenyl)-6-cyclobutyl-2,4,5,6,7,8-hexahydropyrazolo[3,4-d]azepine (may be prepared as described in Example 35) (42 mg, 0.12 mmol), 2-oxazolidinone (21 mg, 0.24 mmol), potassium carbonate (50 mg, 0.36 mmol), copper (I) iodide (8.0 mg, 0.04 mmol) and N,N'-dimethyl-1,2-ethanediamine (5 µl, 0.04 mmol) in dioxane (1.5 ml) was heated in the microwave (high absorption) at 100° C. for 30 minutes. The same amounts again of 2-oxazolidinone, potassium carbonate, copper (I) iodide and N,N'-dimethyl-1,2-ethanediamine were added and the mixture heated in the microwave at 150° C. for 4 hours. The reaction mixture was evaporated in vacuo, then purified by SCX cartridge, followed by Mass Directed Autopreparation to afford the title compound (E37). MS (ES+) m/e 353 [M+H]$^+$.

EXAMPLE 38

3-[4-(6-Cyclobutyl-5,6,7,8-tetrahydropyrazolo[3,4-d]azepin-2(4H)-yl)phenyl]-1-methyl-2,4-imidazolidinedione (E38)

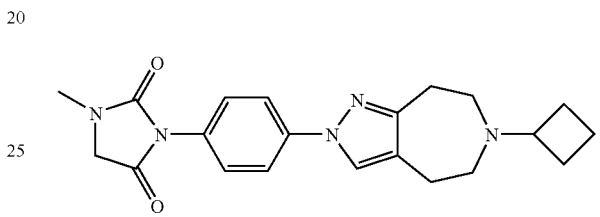

A mixture of 2-(4-bromophenyl)-6-cyclobutyl-2,4,5,6,7,8-hexahydropyrazolo[3,4-d]azepine (may be prepared as described in Example 35) (80 mg, 0.23 mmol), 1-methylhydantoin (52 mg, 0.46 mmol), potassium carbonate (95 mg, 0.7 mmol), copper (I) iodide (13 mg, 0.07 mmol) and N,N'-dimethyl-1,2-ethanediamine (8 µl, 0.07 mmol) in dioxane (2 ml) was heated in the microwave (normal absorption) at 150° C. for 2 hours. The reaction mixture was purified by SCX cartridge, followed by Mass Directed Autopreparation and column chromatography on silica gel, eluting with a mixture of 2M ammonia in methanol/dichloromethane (0-5%) to afford the title compound (E38). MS (ES+) m/e 380 [M+H]$^+$.

EXAMPLE 39

6-Cyclobutyl-2-[4-(4-morpholinyl)phenyl]-2,4,5,6,7,8-hexahydropyrazolo[3,4-d]azepine (E39)

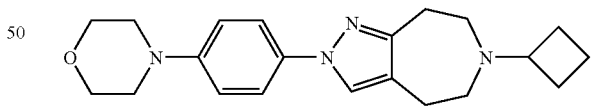

A mixture of 2-(4-bromophenyl)-6-cyclobutyl-2,4,5,6,7,8-hexahydropyrazolo[3,4-d]azepine (may be prepared as described in Example 35) (80 mg, 0.23 mmol), morpholine (40 µl, 0.46 mmol), cesium carbonate (115 mg, 0.35 mmol), tris(dibenzylideneacetone)dipalladium(0) (10 mg, 0.01 mmol) and (9,9-dimethyl-9H-xanthene-4,5-diyl)bis(diphenylphosphane) (20 mg, 0.035 mmol) in dioxane (2 ml) was heated in the microwave (normal absorption) at 100° C. for 2 hours. The same amounts again of morpholine, cesium carbonate, tris(dibenzylideneacetone)dipalladium(0) and (9,9-dimethyl-9H-xanthene-4,5-diyl)bis(diphenylphosphane) were added and the mixture heated in the microwave at 150° C. for 2 hours. The reaction mixture was purified by SCX cartridge, followed by Mass Directed Autopreparation and column chromatography on silica gel, eluting with a mixture of 2M ammonia in methanol/dichloromethane (0-5%) to afford the title compound (E39). MS (ES+) m/e 353 [M+H]⁺.

EXAMPLE 40

6-Cyclobutyl-2-[4-(1-piperidinyl)phenyl]-2,4,5,6,7,8-hexahydropyrazolo[3,4-d]azepine (E40)

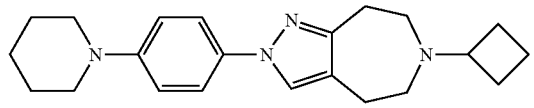

To a solution of 2-[4-(1-piperidinyl)phenyl]-2,4,5,6,7,8-hexahydropyrazolo[3,4-d]azepine (may be prepared as described in Description 43) (42 mg, 0.14 mmol) in dichloromethane (4 ml) was added cyclobutanone (30 μl, 0.42 mmol) followed by acetic acid (3 drops). The mixture was stirred at room temperature for 50 min, then treated with sodium triacetoxyborohydride (89 mg, 0.42 mmol). The mixture was stirred at room temperature for 2.5 hours, then it was diluted with methanol and purified by SCX cartridge to afford the title compound (E40). MS (ES+) m/e 351 [M+H]⁺.

EXAMPLE 41

6-Cyclobutyl-2-[4-(1-pyrrolidinyl)phenyl]-2,4,5,6,7,8-hexahydropyrazolo[3,4-d]azepine (E41)

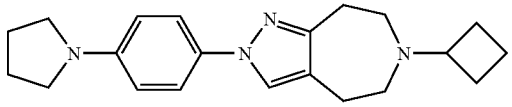

To a solution of 2-[4-(1-pyrrolidinyl)phenyl]-2,4,5,6,7,8-hexahydropyrazolo[3,4-d]azepine (may be prepared as described in Description 45) (25 mg, 0.09 mmol) in dichloromethane (4 ml) was added cyclobutanone (30 μl, 0.45 mmol) followed by acetic acid (3 drops). The mixture was stirred at room temperature for 30 min, then treated with sodium triacetoxyborohydride (95 mg, 0.45 mmol). The mixture was stirred at room temperature for 4 hours, then it was diluted with methanol and purified by SCX cartridge to afford the title compound (E41). MS (ES+) m/e 337 [M+H]⁺.

EXAMPLE 42

3-{(4-[6-(2-Methylpropyl)-5,6,7,8-tetrahydropyrazolo[3,4-d]azepin-2(4-yl]phenyl}-1,3-oxazolidin-2-one (E42)

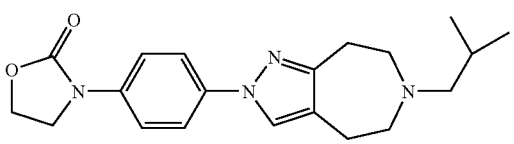

To a solution of 3-[4-(5,6,7,8-tetrahydropyrazolo[3,4-d]azepin-2(4H)-yl)phenyl]-1,3-oxazolidin-2-one (may be prepared as described in Description 27) (35 mg, 0.12 mmol) in dichloromethane (4 ml) was added 2-methylpropanal (35 mg, 0.48 mmol) followed by acetic acid (3 drops). The mixture was stirred at room temperature for 20 min, then treated with sodium triacetoxyborohydride (102 mg, 0.48 mmol). The mixture was stirred at room temperature for 20 hours, then it was diluted with methanol and purified by SCX cartridge to afford the title compound (E42). MS (ES+) m/e 355 [M+H]⁺.

EXAMPLE 43

1-{5-[6-(1-Methylethyl)-5,6,7,8-tetrahydropyrazolo[3,4-d]azepin-2(4H)-yl]-2-pyridinyl}-2-pyrrolidinone (E43)

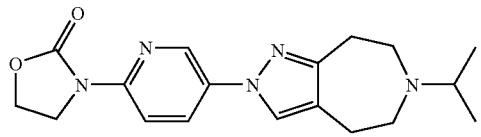

A solution of 1-[5-(5,6,7,8-tetrahydropyrazolo[3,4-d]azepin-2(4H)-yl)-2-pyridinyl]-2-pyrrolidinone (may be prepared as described in Description 19) (37 mg, 0.12 mmol) in dichloromethane (2.5 ml) was treated with acetone (0.018 ml, 0.25 mmol) and then stirred under Argon for 20 min and then treated with sodium triacetoxyborohydride (53 mg, 0.25 mmol) and the resulting mixture stirred under Argon at room temperature for 16.5 hours. 2 hours later, more acetone (2 eq) was then added, followed 5 min later by more sodium triacetoxyborohydride (2 eq) and the mixture stirred under Argon at room temperature for 5 hours. The mixture was then diluted with methanol and then purified by SCX eluting with methanol and then 2M ammonia in methanol to give a 73:27 (by LCMS DAD) 88:12 (by LCMS ELSD) mixture of 1-{5-[6-(1-methylethyl)-5,6,7,8-tetrahydropyrazolo[3,4-d]azepin-2(4H)-yl]-2-pyridinyl}-2-pyrrolidinone hydrochloride (E43) and 1-[5-(5,6,7,8-tetrahydropyrazolo[3,4-d]azepin-2(4H)-yl)-2-pyridinyl]-2-pyrrolidinone (D19) (33 mg). A solution of this mixture in dichloromethane (2.5 ml) was treated with acetone (0.018 ml, 0.25 mmol) under Argon and the mixture stirred for 2-3 min at room temperature. Sodium triacetoxyborohydride (53 mg, 0.25 mmol) was then added and the mixture stirred under Argon at room temperature for 15.75 hours. After an additional 1 hour, more acetone (5 eq) was added followed 5 min later by more sodium triacetoxyborohydride and the mixture stirred at room temperature under Argon for an additional 7.75 h. The mixture was then diluted with methanol and purified by SCX eluting with methanol then methanol/NH₃ (2M). Purified further by SPE (Si) eluting with dichloromethane:methanol 50:1→25:1→10:1→5:1→2:1. Purified further by Mass Directed Autopreparation followed by SCX eluting with methanol then methanol/NH₃ (2M) to afford the title product (E43).

EXAMPLE 44

6-Cyclobutyl-2-[1-(6-methyl-3-pyridinyl)-4-piperidinyl]-2,4,5,6,7,8-hexahydropyrazolo[3,4-d]azepine (E44)

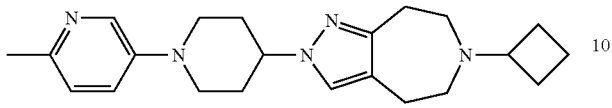

1,1-Dimethylethyl 2-[1-(6-methyl-3-pyridinyl)-4-piperidinyl]-4,5,7,8-tetrahydropyrazolo[3,4-d]azepine-6(2H)-carboxylate (may be prepared as described in Description 50) (27 mg, 0.065 mmol) was stirred in trifluoroacetic acid (0.5 ml)/dichloromethane (1 ml) for 2 hours. Mixture was then diluted with methanol and passed through an SCX cartridge. A mixture of the product in dichloromethane (1.3 ml) was treated with cyclobutanone (0.010 ml, 0.13 mmol) followed by sodium triacetoxyborohydride (28 mg, 0.13 mmol) (about 5 min later). The resulting mixture was then stirred under Argon for 17.25 h. After an additional 1.25 hours, more dichloromethane (2.5 ml), cyclobutanone (0.030 ml) and then sodium triacetoxyborohydride (28 mg) were added and the mixture stirred for an additional 3.75 hours and then for an additional 2.5 hours. After a further 1 hour, more cyclobutanone (0.030 ml) followed by sodium triacetoxyborohydride (2 eq) were added and the resulting mixture left at room temperature under Ar for 16.75 hours. Then dichloromethane (2 ml) was added. Methanol was then added and the mixture purified by SCX eluting with methanol and then methanol/ammonia (2M). This material was purified by Mass Directed Autopreparation to give a product which was purified further by SCX eluting with methanol and then methanol/2M NH$_3$ in methanol to afford the title compound (E44).

EXAMPLE 45

6-Cyclobutyl-2-phenyl-2,4,5,6,7,8-hexahydropyrazolo[3,4-d]azepine (E45)

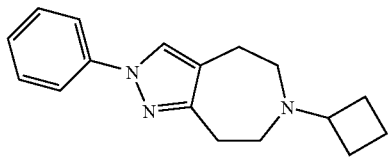

To a suspension of 2-phenyl-2,4,5,6,7,8-hexahydropyrazolo[3,4-d]azepine (may be prepared as described in Description 46) (39 mg, 0.18 mmol) in dichloromethane (4 ml) was added 3 drops of acetic acid, cyclobutanone (28 µl, 0.36 mmol) and sodium triacetoxyborohydride (77 mg, 0.36 mmol). The resulting mixture was allowed to stir at room temperature for 1 hour. The resulting reaction mixture was acidified with 2M hydrochloric acid and applied to an pre equilibrated ion exchange cartridge (SCX), washed with methanol and then a 2M ammonia in methanol solution. The basic fractions were then evaporated in vacuo to afford the title product (E45); MS (ES+) m/e 268 [M+H]$^+$ as a 95:5 mixture of the title compound and 7-cyclobutyl-2-phenyl-2,4,5,6,7,8-hexahydropyrazolo[3,4-c]azepine.

EXAMPLE 46

4-[(6-Cyclobutyl-5,6,7,8-tetrahydropyrazolo[3,4-d]azepin-2(4H)-yl)methyl]benzonitrile (E46)

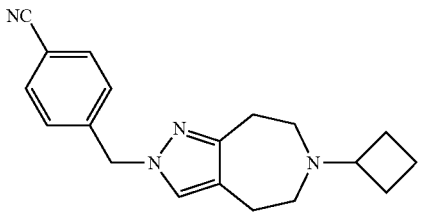

6-Cyclobutyl-2,4,5,6,7,8-hexahydropyrazolo[3,4-d]azepine (may be prepared as described in Description 31) (0.03, 0.16 mmol) in dimethylformamide (2 ml) was treated with sodium hydride (60% dispersion in oil) (0.007 g, 0.172 mmol). After 20 minutes 4-(bromomethyl)benzonitrile (0.037 g, 0.172 mmol) was added and the mixture was then heated at 70° C. for 18 hours. The reaction was then cooled to room temperature, diluted with methanol and applied to a SCX ion exchange cartridge and washed with methanol and then 2M solution of ammonia in methanol. The ammonia containing fractions were then combined and reduced and the resulting crude residue was chromatographed on silica gel eluting with a 2:98 mixture of 2M ammonia in methanol and dichloromethane to furnish the title compound (E46); (MS (ES+): [M+H]$^+$ at m/z 307.1

All publications, including but not limited to patents and patent applications, cited in this specification are herein incorporated by reference as if each individual publication were specifically and individually indicated to be incorporated by reference herein as though fully set forth.

Abbreviations

SCX strong cation exchange

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pCDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 µg ml$^{-1}$. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 μg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 μg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 μm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 μg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of homogenisation buffer (50 mM N-2-hydroxyethylpiperazine-N'-2-ethanesulfonic acid (HEPES), 1 mM ethylenediamine tetra-acetic acid (EDTA), pH 7.4 with KOH), supplemented with 10e-4M leupeptin (acetyl-leucyl-leucyl-arginal; Sigma L2884), 25 μg/ml bacitracin (Sigma B0125), 1 mM phenylmethylsulfonyl fluoride (PMSF) and 2×10e-6M pepstatin A (Sigma). The cells are then homogenised by 2×15 second bursts in a 1 litre glass Waring blender, followed by centrifugation at 500 g for 20 minutes. The supernatant is then spun at 48,000 g for 30 minutes. The pellet is resuspended in homogenisation buffer (4× the volume of the original cell pellet), supplemented with 10e-4M leupeptin (acetyl-leucyl-leucyl-arginal; Sigma L2884) and 25 μg/ml bacitracin (Sigma B0125), either by vortexing for 5 seconds, followed by homogenisation in a Dounce homogeniser (10-15 strokes) or by forcing it through a 10 or 20 ml syringe with no needle against the tube bottom, then through a 0.6 mm needle using a 20 or 50 ml syringe. At this point the preparation is aliquoted into polypropylene tubes and stored at −80° C.

(iii) Generation of Histamine H1 Cell Line

The human H1 receptor was cloned using known procedures described in the literature [Biochem. Biophys. Res. Commun. 1994, 201(2), 894]. Chinese hamster ovary cells stably expressing the human H1 receptor were generated according to known procedures described in the literature [Br. J. Pharmacol. 1996, 117(6), 1071].

Compounds of the invention may be tested for in vitro biological activity in accordance with the following assays:

(I) Histamine H3 Functional Antagonist Assay

For each compound being assayed, in a solid white 384 well plate, is added:—

(a) 0.5 μl of test compound diluted to the required concentration in DMSO (or 0.5 μl DMSO as a control);

(b) 30 μl bead/membrane/GDP mix prepared by mixing Wheat Germ Agglutinin Polystyrene LeadSeeker® (WGA PS LS) scintillation proximity assay (SPA) beads with membrane (prepared in accordance with the methodology described above) and guanosine 5' diphosphate (GDP) (Sigma) in assay buffer (20 mM N-2-Hydroxyethylpiperazine-N'-2-ethanesulfonic acid (HEPES)+100 mM NaCl+10 mM MgCl$_2$, pH7.4 NaOH) to give a final volume of 30 μl which contains 5 μg protein and 0.25 mg bead per well and a 10 μM final concentration of GDP, and incubating at room temperature for 60 minutes on a roller;

(c) 15 μl 0.38 nM [$^{35}$S]-GTPγS (Amersham; Radioactivity concentration=37 MBq/ml; Specific activity=1160 Ci/mmol), histamine (at a concentration that results in the final assay concentration of histamine being EC$_{80}$).

After 2-6 hours, the plate is counted on a Viewlux counter using a 613/55 filter for 5 min/plate. Prior to reading the plate, this is centrifuged for 5 min at 1500 rpm. Data is analysed using a 4-parameter logistical equation. Basal activity used as minimum i.e. histamine not added to well.

(II) Histamine H1 Functional Antagonist Assay

The histamine H1 cell line was seeded into non-coated black-walled clear bottom 384-well tissue culture plates in alpha minimum essential medium (Gibco/Invitrogen, cat no. 22561-021), supplemented with 10% dialysed foetal calf serum (Gibco/Invitrogen cat no. 12480-021) and 2 mM L-glutamine (Gibco/Invitrogen cat no 25030-024) and maintained overnight at 5% CO$_2$, 37° C.

Excess medium was removed from each well to leave 10 μl. 30 μl loading dye (250 μM Brilliant Black, 2 μM Fluo-4 diluted in Tyrodes buffer+probenecid (145 mM NaCl, 2.5 mM KCl, 10 mM HEPES, 10 mM D-glucose, 1.2 mM MgCl$_2$, 1.5 mM CaCl$_2$, 2.5 mM probenecid, pH adjusted to 7.40 with NaOH 1.0 M)) was added to each well and the plates were incubated for 60 minutes at 5% CO$_2$, 37° C.

10 μl of test compound, diluted to the required concentration in Tyrodes buffer+probenecid (or 10 g Tyrodes buffer+probenecid as a control) was added to each well and the plate incubated for 30 min at 37° C., 5% CO$_2$. The plates were then placed into a FLIPR™ (Molecular Devices, UK) to monitor cell fluorescence ($\lambda_{ex}$=488 nm, $\lambda_{EM}$=540 nm) in the manner described in Sullivan et al. (In: Lambert D G (ed.), Calcium Signaling Protocols, New Jersey: Humana Press, 1999, 125-136) before and after the addition of 10 μl histamine at a concentration that results in the final assay concentration of histamine being EC$_{80}$.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

Results

The hydrochloride salts of the compounds of Examples E1-E34 and E336-E46 were tested in the histamine H3 functional antagonism assay. The results are expressed as functional pK$_i$ (fpK$_i$) values. A functional pKi is the negative logarithm of the antagonist equilibrium dissociation constant as determined in the H3 functional antagonist assay using membrane prepared from cultured H3 cells. The results given are averages of a number of experiments. All of the hydrochloride salts tested exhibited antagonism>6.5 fpK$_i$, more particularly the hydrochloride salts of Examples E9-E10, E12-E15, E18, E20, E24-E25, E27, E30-E31, E36-E37, E39, E42 and E44 exhibited antagonism>9.0 fpK$_i$. Most particularly, the hydrochloride salts of Examples E13, E18 and E36-E37 exhibited antagonism>9.5 fpK$_i$.

The hydrochloride salts of the compounds of Examples E1-E34 and E336-E46 were tested in the histamine H1 functional antagonist assay. Again, the results are expressed as functional pK$_i$ (fpK$_i$) values and are averages of a number of experiments. All compounds tested exhibited antagonism<6.0 fpK$_i$.

What is claimed is:

1. A compound of formula (I) or a pharmaceutically acceptable salt thereof:

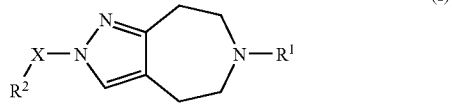

wherein:
R$^1$ represents —C$_{1-6}$ alkyl, —C$_{3-7}$ cycloalkyl or —CH$_2$—C$_{3-7}$ cycloalkyl, wherein said cycloalkyl groups may be optionally substituted by C$_{1-3}$ alkyl;
X represents a bond or —CH$_2$—,
R$^2$ represents -aryl, -aryl-aryl, -aryl-heteroaryl, -aryl-heterocyclyl, -heteroaryl, -heteroaryl-aryl, -heteroaryl-heteroaryl, -heteroaryl-heterocyclyl, -heterocyclyl, -heterocyclyl-aryl, -heterocyclyl-heteroaryl or -heterocyclyl-heterocyclyl;
wherein said aryl, heteroaryl and heterocyclyl groups of R$^2$ may be optionally substituted by one or more substituents which may be the same or different, and which are selected from the group consisting of halogen, hydroxy, cyano, nitro, =O, C$_{1-6}$ alkyl, haloC$_{1-6}$ alkyl, —O-haloC$_{1-6}$ alkyl, —O—C$_{1-6}$ alkyl, —C$_{1-6}$ alkyl-O—C$_{1-6}$ alkyl, —CO$_2$R$^4$, —COR$^4$, —C$_{1-6}$ alkyl-COR$^4$, —SR$^4$, —SO$_2$R$^4$, —SOR$^4$, —OSO$_2$R$^4$, —C$_{1-6}$ alkyl-SO$_2$R$^4$, —C$_{1-6}$ alkyl-NR$^4$SO$_2$R$^5$, —C$_{1-6}$ alkyl-SO$_2$NR$^4$R$^5$, —NR$^4$R$^5$, —C$_{1-6}$ alkyl-NR$^4$R$^5$, —C$_{3-8}$ cycloalkyl-NR$^4$R$^5$, —CONR$^4$R$^5$, —NR$^4$COR$^5$, —C$_{1-6}$ alkyl-NR$^4$COR$^5$, —C$_{1-6}$ alkyl-CONR$^4$R$^5$, —NR$^4$SO$_2$R$^5$, —OCONR$^4$R$^5$, —NR$^4$CO$_2$R$^5$, —NR$^6$CONR$^4$R$^5$ and —SO$_2$NR$^4$R$^5$, wherein R$^4$, R$^5$ and R$^6$ independently represent hydrogen, C$_{1-6}$ alkyl, or wherein —NR$^4$R$^5$ may represent a nitrogen containing heterocyclyl group; and
wherein R$^4$, R$^5$ and R$^6$ may be optionally substituted by one or more substituents which may be the same or different, and which are selected from the group consisting of halogen, hydroxy, cyano, amino, nitro and =O.

2. The compound or salt according to claim 1, wherein X represents a bond.

3. The compound or salt according to claim 1, wherein R$^2$ represents -aryl, -aryl-heterocyclyl, -aryl-heteroaryl, -heteroaryl-heterocyclyl or -heterocyclyl-heteroaryl.

4. The compound or salt according to claim 3, wherein R$^2$ represents -aryl-heterocyclyl or -heterocyclyl-heteroaryl.

5. The compound or salt according to claim 1, wherein the substituents on the aryl, heteroaryl or heterocyclyl groups of R$^2$ are selected from halogen, hydroxy, cyano, nitro, =O, C$_{1-6}$ alkyl, haloC$_{1-6}$ alkyl, —O-haloC$_{1-6}$ alkyl, —O—C$_{1-6}$ alkyl, —SO$_2$R$^4$, —CONR$^4$R$^5$, —NR$^4$COR$^5$, —NR$^4$SO$_2$R$^5$ and —SO$_2$NR$^4$R$^5$.

6. The compound or salt according to claim 1, wherein R$^4$, R$^5$ and R$^6$ are independently selected from hydrogen and C$_{1-3}$ alkyl.

7. A compound which is:
N,N-Dimethyl-4-[6-(2-methylpropyl)-5,6,7,8-tetrahydropyrazolo[3,4-d]azepin-2(4H)-yl]benzamide;
N,N-Dimethyl-4-[6-(1-methylethyl)-5,6,7,8-tetrahydropyrazolo[3,4-d]azepin-2(4H)-yl]benzamide;
4-(6-Cyclobutyl-5,6,7,8-tetrahydropyrazolo[3,4-d]azepin-2(4H)-yl)-N,N-dimethylbenzamide;
4-(6-Cyclopentyl-5,6,7,8-tetrahydropyrazolo[3,4-d]azepin-2(4H)-yl)-N,N-dimethylbenzamide;
N-Methyl-4-[6-(2-methylpropyl)-5,6,7,8-tetrahydropyrazolo[3,4-d]azepin-2(4H)-yl]benzamide;
N-Methyl -4-[6-(1-methylethyl)-5,6,7,8-tetrahydropyrazolo[3,4-d]azepin-2(4H)-yl]benzamide;
4-(6-Cyclobutyl-5,6,7,8-tetrahydropyrazolo[3,4-d]azepin-2(4H)-yl)-N-methylbenzamide;
4-(6-Cyclopentyl-5,6,7,8-tetrahydropyrazolo[3,4-d]azepin-2(4H)-yl)-N-methylbenzamide;
3-{4-[6-(1-Methylethyl)-5,6,7,8-tetrahydropyrazolo[3,4-d]azepin-2(4H)-yl]phenyl}-1,3-oxazolidin-2-one;
1-Methyl-3-{4-[6-(1-methylethyl)-5,6,7,8-tetrahydropyrazolo[3,4-d]azepin-2(4H)-yl]phenyl}-2-imidazolidinone;
1-Methyl-3-{4-[6-(2-methylpropyl)-5,6,7,8-tetrahydropyrazolo[3,4-d]azepin-2(4H)-yl]phenyl}-2-imidazolidinone;
1-[5-(6-Cyclobutyl-5,6,7,8-tetrahydropyrazolo[3,4-d]azepin-2(4H)-yl)-2-pyridinyl]-2-pyrrolidinone;
1-[4-(6-Cyclobutyl-5,6,7,8-tetrahydropyrazolo[3,4-d]azepin-2(4H)-yl) phenyl]-2-pyrrolidinone;
1-{4-[6-(1-Methylethyl)-5,6,7,8-tetrahydropyrazolo[3,4-d]azepin-2(4H)-yl]phenyl}-2-pyrrolidinone;
6-(1-Methylethyl)-2-[4-(3-methyl-1,2,4-oxadiazol-5-yl)phenyl]-2,4,5,6,7,8-hexahydropyrazolo[3,4-d]azepine;
4-[6-(2-Methylpropyl)-5,6,7,8-tetrahydropyrazolo[3,4-d]azepin-2(4H)-yl]benzamide;
4-[6-(1-Methylethyl)-5,6,7,8-tetrahydropyrazolo[3,4-d]azepin-2(4H)-yl]benzamide;
1-[4-(6-Ethyl-5,6,7,8-tetrahydropyrazolo[3,4-d]azepin-2(4H)-yl)phenyl]-2-pyrrolidinone;
1-{4-[6-(Cyclopropylmethyl)-5,6,7,8-tetrahydropyrazolo[3,4-d]azepin-2(4H)-yl]phenyl}-2-pyrrolidinone;
1-{4-[6-(2-Methylpropyl)-5,6,7,8-tetrahydropyrazolo[3,4-d]azepin-2(4H)-yl]phenyl}-2-pyrrolidinone;
2-[4-(3-Methyl-1,2,4-oxadiazol-5-yl)phenyl]-6-(2-methylpropyl)-2,4,5,6,7,8-hexahydropyrazolo[3,4-d]azepine;
1-[4-(6-Cyclohexyl-5,6,7,8-tetrahydropyrazolo[3,4-d]azepin-2(4H)-yl)phenyl]-2-pyrrolidinone;
4-(6-Cyclopentyl-5,6,7,8-tetrahydropyrazolo[3,4-d]azepin-2(4H)-yl)benzamide;
1-[4-(6-Cyclopentyl-5,6,7,8-tetrahydropyrazolo[3,4-d]azepin-2(4H)-yl)phenyl]-2-pyrrolidinone;
6-Cyclobutyl-2-[4-(3-methyl-1,2,4-oxadiazol-5-yl)phenyl]-2,4,5,6,7,8-hexahydropyrazolo azepine;
4-(6-Cyclobutyl-5,6,7,8-tetrahydropyrazolo[3,4-d]azepin-2(4H)-yl)benzamide;
6-Cyclopentyl-2-[4-(3-methyl-1,2,4-oxadiazol-5-yl)phenyl]-2,4,5,6,7,8-hexahydropyrazolo[3,4-d]azepine;

6-Cyclobutyl-2-[4-(methylsulfonyl)phenyl]-2,4,5,6,7,8-hexahydropyrazolo[3,4-d]azepine;
N-[4-(6-Cyclobutyl-5,6,7,8-tetrahydropyrazolo[3,4-d]azepin-2(4H)-yl)phenyl]methanesulfonamide;
3-[4-(6-Cyclopentyl-5,6,7,8-tetrahydropyrazolo[3,4-d]azepin-2(4H)-yl)phenyl]-1,3-oxazolidin-2-one ;
1-[4-(6-Cyclopentyl-5,6,7,8-tetrahydropyrazolo[3,4-d]azepin-2(4H)-yl)phenyl]-3-methyl-2-imidazolidinone;
4-(6-Cyclobutyl-5,6,7,8-tetrahydropyrazolo[3,4-d]azepin-2(4H)-yl)benzonitrile;
4-[6-(2-Methylpropyl)-5,6,7,8-tetrahydropyrazolo[3,4-d]azepin-2(4H)-yl]benzonitrile;
4-[6-(1-Methylethyl)-5,6,7,8-tetrahydropyrazolo[3,4-d]azepin-2(4H)-yl]benzonitrile;
2-(4-Bromophenyl)-6-cyclobutyl-2,4,5,6,7,8-hexahydropyrazolo[3,4-d]azepine;
1-[4-(6-Cyclobutyl-5,6,7,8-tetrahydropyrazolo[3,4-d]azepin-2(4H)-yl)phenyl]-3-methyl-2-imidazolidinone;
3-[4-(6-Cyclobutyl-5,6,7,8-tetrahydropyrazolo[3,4-d]azepin-2(4H)-yl)phenyl]-1,3-oxazolidin-2-one;
3-[4-(6-Cyclobutyl-5,6,7,8-tetrahydropyrazolo[3,4-d]azepin-2(4H)-yl)phenyl]-1-methyl-2,4-imidazolidinedione;
6-Cyclobutyl-2-[4-(4-morpholinyl)phenyl]-2,4,5,6,7,8-hexahydropyrazolo[3,4-d]azepine;
6-Cyclobutyl-2-[4-(1-piperidinyl)phenyl]-2,4,5,6,7,8-hexahydropyrazolo[3,4-d]azepine;
6-Cyclobutyl-2-[4-(1-pyrrolidinyl)phenyl]-2,4,5,6,7,8-hexahydropyrazolo[3,4-d]azepine;
3-{4-[6-(2-Methylpropyl)-5,6,7,8-tetrahydropyrazolo[3,4-d]azepin-2(4H)-yl]phenyl}-1,3-oxazolidin-2-one;
1-{5-[6-(1-Methylethyl)-5,6,7,8-tetrahydropyrazolo[3,4-d]azepin-2(4H)-yl]-2-pyridinyl}-2-pyrrolidinone;
6-Cyclobutyl-2-[1-(6-methyl-3-pyridinyl)-4-piperidinyl]-2,4,5,6,7,8-hexahydropyrazolo[3,4-d]azepine;
6-Cyclobutyl-2-phenyl-2,4,5,6,7,8-hexahydropyrazolo[3,4-d]azepine; or
4-[(6-Cyclobutyl-5,6,7,8-tetrahydropyrazolo[3,4-d]azepin-2(4H)-yl)methyl]benzonitrile;
or a pharmaceutically acceptable salt thereof.

8. A pharmaceutical composition which comprises the compound or salt as defined in claim 1 and a pharmaceutically acceptable carrier or excipient.

9. A method of treatment of cognitive impairments in Alzheimer's disease, mild cognitive impairment, age-related memory dysfunction, epilepsy, neuropathic pain, Parkinson's disease, cognitive deficit of schizophrenia, attention deficit hyperactivity disorder, or depression which comprises administering to a human in need thereof an effective amount of the compound or salt as defined in claim 1 or a pharmaceutically acceptable salt thereof.

10. A compound which is N-Methyl-4-[6-(2-methylpropyl)-5,6,7,8-tetrahydropyrazolo[3,4-d]azepin-2(4H)-yl]benzamide, having the following structure:

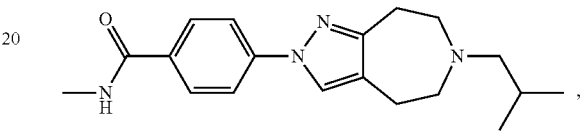

or a pharmaceutically acceptable salt thereof.

11. A compound which is N-Methyl-4-[6-(1-methylethyl)-5,6,7,8-tetrahydropyrazolo[3,4-d]azepin-2(4H)-yl]benzamide, having the following structure:

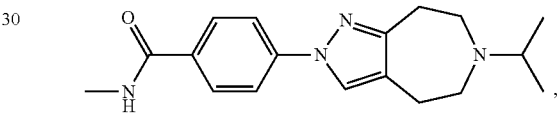

or a pharmaceutically acceptable salt thereof.

* * * * *